United States Patent
Yamasaki et al.

(10) Patent No.: US 9,150,639 B2
(45) Date of Patent: Oct. 6, 2015

(54) ANTIBODY AND ANTIBODY FRAGMENT INTRODUCED NEW MODIFICATION SITES

(75) Inventors: Motoo Yamasaki, Shizuoka (JP); Yasuhisa Shiraishi, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 0 days.

(21) Appl. No.: 13/072,924

(22) Filed: Mar. 28, 2011

(65) Prior Publication Data

US 2012/0009621 A1    Jan. 12, 2012

Related U.S. Application Data

(60) Provisional application No. 61/389,887, filed on Oct. 5, 2010, provisional application No. 61/317,935, filed on Mar. 26, 2010.

(51) Int. Cl.

| C07K 16/28 | (2006.01) |
|---|---|
| C07K 16/32 | (2006.01) |
| A61K 47/48 | (2006.01) |
| C07K 16/00 | (2006.01) |
| C12P 21/08 | (2006.01) |

(52) U.S. Cl.
CPC ........... *C07K 16/00* (2013.01); *A61K 47/48561* (2013.01); *C07K 16/2863* (2013.01); *C07K 16/32* (2013.01); *A61K 47/48* (2013.01); *A61K 47/4823* (2013.01); *A61K 47/48092* (2013.01); *A61K 47/48215* (2013.01); *A61K 47/48369* (2013.01); *A61K 47/48384* (2013.01); *C07K 2317/24* (2013.01); *C07K 2317/522* (2013.01)

(58) Field of Classification Search
CPC .... C07K 16/00; C07K 16/2863; C07K 16/32; C07K 2317/24; C07K 2317/522; C07K 16/2809; C07K 16/2878; C07K 16/2896; C07K 2317/15; C07K 2317/31; C07K 2317/34; C07K 2317/54; A61K 47/48215; A61K 47/48384; A61K 47/48369; A61K 47/48092
See application file for complete search history.

(56) References Cited

U.S. PATENT DOCUMENTS

| 7,521,541 | B2 * | 4/2009 | Eigenbrot et al. ......... 530/387.1 |
|---|---|---|---|
| 2003/0049203 | A1 * | 3/2003 | Elmaleh et al. .............. 424/1.73 |
| 2009/0028856 | A1 * | 1/2009 | Chen et al. ................. 424/133.1 |
| 2009/0258420 | A1 * | 10/2009 | Van Vlijmen et al. ........ 435/358 |
| 2011/0301334 | A1 | 12/2011 | Bhakta et al. |
| 2012/0148580 | A1 | 6/2012 | Chennamsetty et al. |

FOREIGN PATENT DOCUMENTS

| JP | 2008516896 A | | 5/2008 |
|---|---|---|---|
| WO | 2006034488 A2 | | 3/2006 |
| WO | WO 2006/034488 | * | 3/2006 |
| WO | 2007/010231 A1 | | 1/2007 |
| WO | WO 2007/140371 | * | 12/2007 |
| WO | WO 2008/020827 | * | 2/2008 |
| WO | WO 2008/141044 | * | 11/2008 |
| WO | WO 2009/052249 | * | 4/2009 |
| WO | 2009/092011 A1 | | 7/2009 |
| WO | 2010141902 A2 | | 12/2010 |
| WO | 2011156328 A1 | | 12/2011 |

OTHER PUBLICATIONS

Hornick et al, J Nucl Med 41: 355-362, 2000.*
Stimmel et al, J Biol Chemistry 275 (39: 30445-30450, 2000.*
International Searching Authority, International Search Report dated May 31, 2011 issued in counterpart International Application No. PCT/JP2011/057257.
Lyons A et al: "Site-Specific Attachment to Recombinant Antibodies Via Introduced Surface Cysteine Residues", Protein Engineering, Oxford University Press, Surrey, GB, vol. 3, No. 8, pp. 703-708, 1990, XP001000052.
Shopes B. "A genetically engineered human IgG with limited flexibility fully initiates cytolysis via complement", Molecular Immunology, Pergamon, GB, vol. 30, No. 6, pp. 603-609, 1993.
Junutula et al: "Rapid identification of reactive cysteine residues for site-specific labeling of antibody-Fabs", Journal of Immunological Methods, Elsevier Science Publishers B.V.,Amsterdam, NL, vol. 332 (2008), pp. 41-52, (available online Jan. 14, 2008).
Chris Chumsae et al: "Identification and Localization of Unpaired Cysteine Residues in Monoclonal Antibodies by Fluorescence Labeling and Mass Spectrometry", Analytical Chemistry, vol. 81, No. 15, Aug. 1, 2009, pp. 6449-6457.
European Patent Office, Communication issued Oct. 31, 2013 in a counterpart European Application No. 11759544.7.

* cited by examiner

*Primary Examiner* — Phuong Huynh
(74) *Attorney, Agent, or Firm* — Sughrue Mion, PLLC

(57) ABSTRACT

The present invention relates to an antibody or antibody fragment comprising novel Cys residue, to which a hydrophilic macromolecular group or amphipathic macromolecular group can be bound at a high efficiency. In addition, the present invention relates to a monoclonal antibody modified product or an antibody fragment modified product in which cysteine residue is chemically modified.

14 Claims, 6 Drawing Sheets

ANTIBODY AND ANTIBODY FRAGMENT INTRODUCED NEW MODIFICATION SITES

BACKGROUND OF THE INVENTION

1. Field of the Invention

The present invention relates to a novel antibody or antibody fragment comprising a cysteine residue (hereinafter referred to as Cys residue), to which a hydrophilic macromolecular group or amphipathic macromolecular group can be bound at a high efficiency. In addition, the present invention also relates to a novel antibody modified product or antibody fragment modified product in which the Cys residue is chemically modified.

2. Brief Description of the Background Art

Since antibodies have high binding affinity, binding specificity and high stability in blood, application of the antibodies as diagnostic agents or therapeutic agents for human are progressed (Non-patent Reference 1). As the background of advance in the application of therapeutic antibodies, preparation of human chimeric antibodies and humanized antibodies making use of genetic engineering is considered (Non-patent References 2 to 5). A human chimeric antibody comprises an antibody variable region derived from an antibody of an animal other than human, and a constant region derived from a human antibody.

A humanized antibody comprises complementarity-determining regions (CDR) derived from an antibody of an animal other than human in variable region of the antibody, and the remainder of framework regions (FR) and the constant region derived from a human antibody. Due to this, problems relating to the non-human animal antibodies such as high immunogenicity and low effector activity would be solved.

However, since such antibodies are giant molecules having a molecular weight of exceeding 100,000, their transition from blood into tissues is considerably slow. Accordingly, studies are carrying out on an antibody fragment having an increased transitional activity in the living body and a lower molecular weight. The high specificity and affinity in an antibody therapy can be depending on CDRs of antibody variable region.

As the antibody fragment having an antibody variable region, for example, various shapes such as Fv, Fab, Fab', F(ab')$_2$, single chain antibody (scFv), dimerized V region (diabody), and disulfide stabilized V region (dsFv) are known, but the short blood half life accompanied by lowering of the molecular weight comes to be a serious problem.

As a method for solving this problem, there is an antibody fragment modified product modified by a hydrophilic macromolecule group or amphipathic macromolecule group such as polyethylene glycol (PEG). It is possible to adjust a blood half life from several minutes to several hours by increasing the average molecular weight of PEG, and in the case of Fab, it became possible to obtain a blood half life equivalent to the corresponding antibody by binding Fab to PEG having a molecular weight of 40 kDa (Non-patent Reference 6).

The exiting method for modifying Fab fragment with PEG is a method in which a Cys residue contributing to a disulfide bond at the C-terminal site is used as a binding region or a method in which a Cys residue contributing to a disulfide bond at the hinge region is used as a binding region by further elongating the C-terminal site of Fab fragment by the hinge region. However, in each case of the fragments, it is difficult to obtain the Cys residue under free form in the expression and purification steps. Thus, a reduction step is necessary as a pretreatment of the PEG modification (Non-patent Reference 6).

On the other hand, an antibody-drug conjugate (ADC) has been drawing attention as a new antibody derivative making use of the high binding specificity of antibody (Non-patent References 7 and 8). ADC is possible to deliver a drug as one of the functional molecules loaded on the antibody derivative, specifically into a target cell by endocytosis of a target antigen upon binding the antibody.

Although effector function of the antibody has a mechanism of action outside of a cell mediated by an immune system, since ADC has an intracellular mechanism of action, it is possible to use it depending on biological characteristics of a target antigen. For example, in the United States, Mylotarg (registered trademark) (Gemtuzumab Ozogamicin) has been approved as an ADC for the first time in the world. In addition, in the Phase II trial of Tratsuzumab-DM1 on Her2-positive progressive breast cancer patients, reduction of the cancer has been found in 25% of the patients. Accordingly, progress in the developing state of ADC is remarkable, and it is expected to be a new form of pharmaceuticals in the future.

According to a result of study using a cell line, drug efficacy of ADC is related to both the potency of the drug and the number of bond of the loaded drugs. However, in the case of a hydrophobic drug, a problem of considerably lowering its stability in blood has been found in a drug efficacy test using animal individual, due to increase in drug-dependent hydrophobic property (Non-patent Reference 9).

Since PEG has high hydration property, it is possible to improve hydrophobic property by adjusting the molecular weight depending on the drug to be used. As a method for solving this problem, development of a drug comprising a hydrophilic macromolecule or amphipathic macromolecule such as PEG has also been started, it is expected that the development of a hydrophilic or amphipathic molecule for the purpose of enhancement of drug efficacy of ADC will be progressed greatly (Patent References 1 and 2)).

In the existing ADC, a drug is covalently bound to an α-amino group of the N-terminal, an ε-amino group of a lysine (Lys) residue or a thiol group of a Cys residue in the antibody molecule or antibody fragment molecule. However, when two or more drugs are introduced into one antibody molecule, since generally it is necessary to bind them to amino acid residues having different reactivity, a heterogeneous mixture having different numbers of drugs is formed depending on the reaction conditions such as the reaction scale, the number of equivalences and the like. Thus, it also accompanies a difficulty in constructing a production process.

The thiol group comprised in the Cys residue among natural amino acids is an ideal functional group in order to carry out the reaction under mild conditions because it has high reactivity even at a neutral pH range. In general, since it shows its higher reactivity for an electrophilic reaction reagent than that of α-amino group of the amino-terminal or the ε-amino group of a Lys residue inside the protein, or the hydroxyl group derived from a serine (Ser) residue or a threonine (Thr) residue, it is possible to control the reaction site easily.

Accordingly, when an antibody or antibody fragment is chemically modified with a hydrophilic macromolecule or amphipathic macromolecule such as PEG or with a functional molecule such as a drug, by introducing one or more of a stable free Cys residue into a specified site of the antibody or antibody fragment, particularly into the constant region, further efficient chemical modification, reduction of the number of steps and avoidance of structural instabilization accompanied by the disulfide bond destruction due to the reduction operation can be expected.

Conventionally, when a protein is expressed in the periplasmic space of *Escherichia coli* or in the culture supernatant of a eukaryotic cell, since the protein-derived Cys residue or the Cys residue introduced by artificially substituting an amino acid residue is affected by the formation of intermolecular disulfide bond, S-glutathione formation and the like, it was difficult to be substituted with the free Cys residue having reactivity (Non-patent References 10 and 11).

In addition, regarding the substitution for a Cys residue in an antibody molecule, it has been reported that the ratio of the free Cys residue of inside the antibody molecule is higher than that of the surface of the antibody molecule, but the ratio of free Cys residue to all of the substituted Cys residues is approximately 50% at the maximum (Non-patent Reference 12 and Patent Reference 3).

On the other hand, it has also been reported a method for substituting a free Cys residue for a structural region having a high ratio of solvent accessible surface area or a residue having a structure close to the Cys residue, such as a Ser residue or a Thr residue, based on the structural information (Patent References 4 to 6), but it is necessary to carry out a reduction treatment in order to obtain a free Cys residue.

In addition, a substitution site to a free Cys residue in which a low molecular maleimide-biotin complex is modified at a high efficiency of 60 to 100%, by the PHESELECTOR assay, using a phage system (Non-patent Reference 13 and Patent Reference 7) has been found, but there is no description on the modification efficiency with a hydrophilic macromolecular group or amphipathic macromolecular group such as PEG.

CITATION LIST

Patent Literature

Patent Literature 1: U.S. Pat. No. 6,638,509
Patent Literature 2: WO2009/134952
Patent Literature 3: U.S. Pat. No. 5,219,996
Patent Literature 4: WO2008/020827
Patent Literature 5: WO2008/038024
Patent Literature 6: WO2009/092011
Patent Literature 7: WO2006/034488

Non-Patent Literature

Non-patent Literature 1: *Monoclonal Antibodies*: Principles and Applications, Wiley-Liss, Inc., (1995)
Non-patent Literature 2: *Nature*, 312, 643-646 (1984)
Non-patent Literature 3: *Proc. Natl. Acad. Sci. USA*, 81, 6851-6855 (1984)
Non-patent Literature 4: *Nature*, 321, 522-525 (1986)
Non-patent Literature 5: *Nature*, 332, 323-327 (1988)
Non-patent Literature 6: *Protein Eng. Des. Sel.*, 20, 227-234 (2007)
Non-patent Literature 7: *Cancer J.*, 14, 154-169 (2008)
Non-patent Literature 8: *Acc Chem. Res.*, 41, 98-107 (2008)
Non-patent Literature 9: *Clin. Cancer Res.*, 10, 7063-7070 (2004)
Non-patent Literature 10: *Eur. J. Biochem.*, 267, 4928-4944 (2000)
Non-patent Literature 11: *Biochem. Biophy. Res. Commun.*, 242, 1-9 (1998)
Non-patent Literature 12: *Protein Eng.*, 3, 703-708 (1990)
Non-patent Literature 13: *J. Immunol. Methods*, 332, 41-52 (2008)

SUMMARY OF THE INVENTION

Accordingly, an object of the present invention is to provide an antibody substituted with a stable free Cys residue or an antibody fragment thereof, which is hardly affected by the formation of intramolecular disulfide bond between molecules, S-glutathione formation and the like and can be modified with a hydrophilic macromolecular group or amphipathic macromolecular group such as PEG or a functional molecule such as a drug at a high efficiency.

More specifically, the present invention provides a monoclonal antibody in which at least one amino acid in the constant region is substituted with cysteine residue or an antibody fragment thereof, a hybridoma which produces the monoclonal antibody or the antibody fragment thereof, a DNA encoding the monoclonal antibody or the antibody fragment thereof, a vector which comprises the DNA, a transformant which is obtainable by introducing the vector into a host cell, a method for producing a monoclonal antibody or an antibody fragment thereof by using the hybridoma or the transformant, and a monoclonal antibody in which at least one substituted cysteine residue is chemically modified or the antibody fragment thereof.

Since the monoclonal antibody or the antibody fragment thereof of the present invention comprises a constant region in which one or more amino acid residues in a wild type constant region are substituted with cysteine residues, as a suitable embodiment, comprises a constant region in which specific amino acid residues in a wild type constant region are substituted with cysteine residues, it can be modified by a hydrophilic macromolecular group or amphipathic macromolecular group such as PEG in a high efficiency without depending on the amino acid sequence of variable region of an antibody, and can prevent decrease in blood half life when its molecular weight is lowered. By binding it to a functional molecule typified by a drug and the like, high functioning of the monoclonal antibody or the antibody fragment can be provided. In addition, the monoclonal antibody or the antibody fragment thereof of the present invention is markedly useful because the substituted Cys residue is stabyfree and a reduction treatment as a pretreatment before modification by PEG and the like is not necessary.

DETAILED DESCRIPTION OF THE INVENTION

Figure 1:
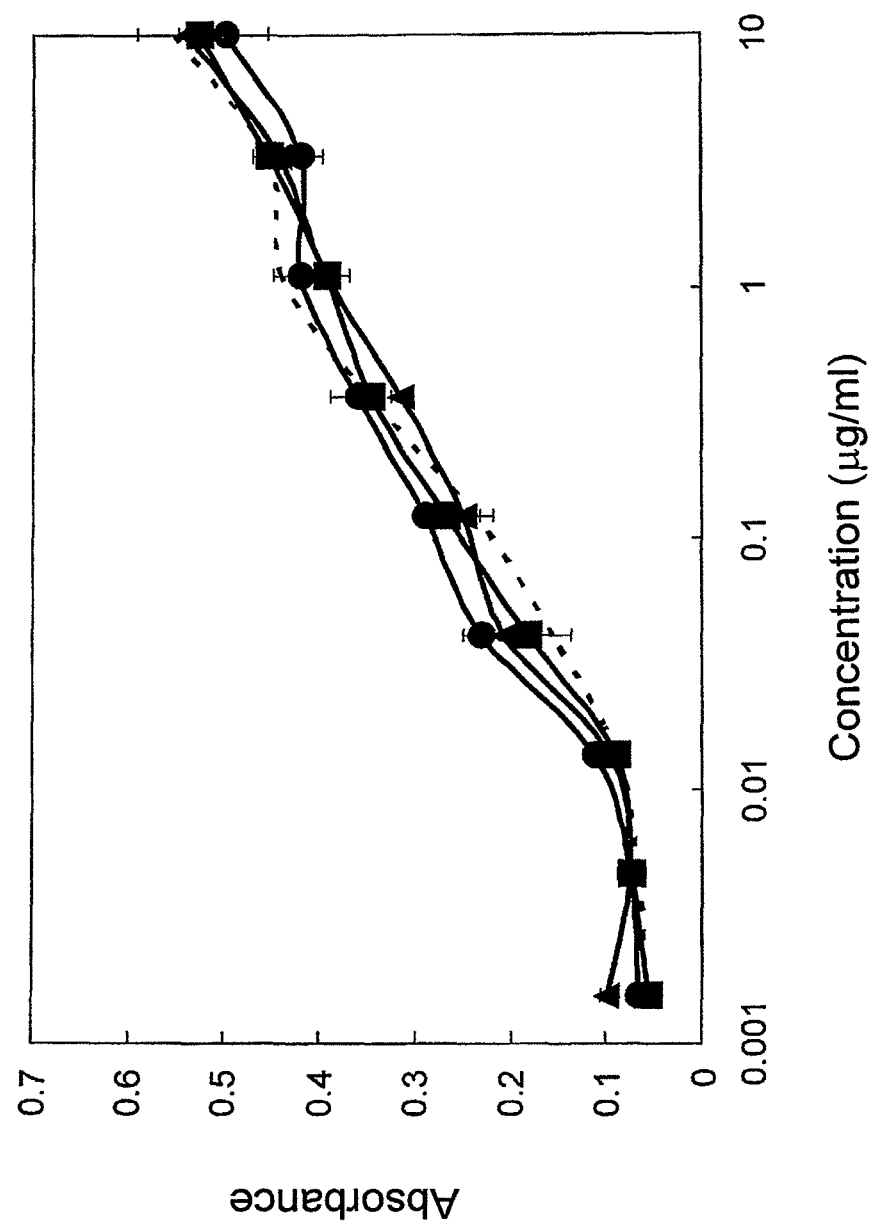
FIG. 1 is a graph showing binding activity of a Cys residue-substituted anti-Her2 Fab to Her2. The ordinate represents the absorbance at 450 nm, and the abscissa concentration of Fab (μg/ml), respectively. The wild type is represented by a dotted line, and the light chain Q124C is represented by ▲, and the light chain H198C is represented by ■ and the light chain L201C is represented by ●.

The gist of the present invention is as follows.

1. A monoclonal antibody or an antibody fragment thereof comprising a constant region, wherein one or more amino acids in the constant region are substituted with a cysteine residue.

2. The monoclonal antibody or the antibody fragment thereof described in the above item 1, wherein one or more amino acids existing in a light chain constant region are substituted with a cysteine residue.

3. The monoclonal antibody or the antibody fragment thereof described in the above item 1, wherein one or more amino acids existing in a heavy chain constant region are substituted with a cysteine residue.

4. The monoclonal antibody or the antibody fragment thereof described in the above item 3, wherein one or more amino acids existing in CH1 region are substituted with a cysteine residue.

5. The monoclonal antibody or the antibody fragment thereof described in any one of the above items 1 to 4, wherein the ratio of solvent accessible surface area of the amino acids to be substituted with a cysteine residue is 30% or less.

6. The monoclonal antibody or the antibody fragment thereof described in any one of the above items 1 to 5, wherein the antibody belongs to a class of immunoglobulin G (IgG).

7. The monoclonal antibody or the antibody fragment thereof described in any one of the above items 1 to 6, wherein the constant region is a constant region derived from a human antibody.

8. The monoclonal antibody or the antibody fragment thereof described in any one of the above items 1 to 7, wherein the monoclonal antibody belongs to a class of human IgG and one or more of amino acids selected from the following (1) to (6) are substituted with a cysteine residue:
(1) the amino acid at position 124 of human IgG light chain region in Kabat numbering
(2) the amino acid at position 198 of human IgG light chain region in Kabat numbering
(3) the amino acid at position 201 of human IgG light chain region in Kabat numbering
(4) the amino acid at position 140 of human IgG heavy chain region in EU numbering (the amino acid at position 138 of human IgG heavy chain region in Kabat numbering)
(5) the amino acid at position 147 of human IgG heavy chain region in EU numbering (the amino acid at position 145 of human IgG heavy chain region in Kabat numbering)
(6) the amino acid at position 183 of human IgG heavy chain region in EU numbering (the amino acid at position 188 of human IgG heavy chain region in Kabat numbering).

9. The monoclonal antibody or the antibody fragment thereof described in any one of the above items 1 to 8, wherein at least one of said substituted cysteine residues is chemically modified.

10. The monoclonal antibody or the antibody fragment thereof described in any one of the above items 1 to 9, wherein the substituted cysteine residue is chemically modified by a chemical modification reaction under non-reducing conditions.

11. The monoclonal antibody or the antibody fragment thereof described in any one of the above items 1 to 10, wherein 40% or more of said substituted cysteine residues are chemically modified.

12. The monoclonal antibody or the antibody fragment thereof described in any one of the above items 9 to 11, wherein the chemical modification is binding of a thiol group of the cysteine residue with a modification group comprising a hydrophilic macromolecule or amphipathic macromolecule.

13. The monoclonal antibody or the antibody fragment thereof described in the above item 12, wherein the hydrophilic macromolecule or amphipathic macromolecule is polyoxyalkylene, polyol or polysaccharide.

14. The monoclonal antibody or the antibody fragment thereof described in any one of the above items 9 to 13, wherein said chemical modification is binding of a thiol group of the cysteine residue with a modification group comprising a functional molecule.

15. The monoclonal antibody or the antibody fragment thereof described in the above item 14, wherein the functional molecule is a drug, a biologically active peptide, a biologically active protein, a nucleic acid, a radiolabeled compound, a sugar chain, a lipid or a fluorescent compound.

16. The monoclonal antibody or the antibody fragment thereof described in the above item 15, wherein the functional molecule is a nucleic acid.

17. The monoclonal antibody or the antibody fragment thereof described in the above item 15, wherein the drug is an antitumor agent, an antibiotic or an antiviral agent.

18. The monoclonal antibody or the antibody fragment thereof described in any one of the above items 12 to 17, which has a molecular weight per one modification group of 500 Da or more.

19. The monoclonal antibody or the antibody fragment described in any one of the above items 1 to 18, which has a cytotoxicity.

20. The monoclonal antibody or the antibody fragment thereof described in the above item 19, wherein the cytotoxicity is an antibody-dependent cellular cytotoxicity or a complement-dependent cytotoxicity.

21. The antibody fragment thereof described in any one of the above items 1 to 20, wherein the antibody fragment is an antibody fragment thereof selected from Fab, Fab' and F(ab')$_2$.

22. The monoclonal antibody or the antibody fragment thereof described in any one of the above items 1 to 21, wherein the monoclonal antibody is a recombinant antibody.

23. The monoclonal antibody or the antibody fragment thereof described in the above item 22, wherein the recombinant antibody is a chimeric antibody, a humanized antibody or a human antibody.

24. A DNA encoding the monoclonal antibody or the antibody fragment thereof described in any one of the above items 1 to 8 and 19 to 23.

25. A recombinant vector comprising the DNA described in the above item 24.

26. A transformant, which is obtainable by introducing the recombinant vector described in the above item 25 into a host cell.

27. A method for producing the monoclonal antibody or the antibody fragment thereof described in any one of the above items 1 to 23, comprising culturing the transformant described in the above item 26 in a medium and recovered the antibody or the antibody fragment thereof from the culture.

28. A method for producing the monoclonal antibody or the antibody fragment thereof described in any one of the above items 9 to 23, comprising chemically modifying a cysteine residue of the antibody or the antibody fragment thereof recovering from the above culture by a chemical modification reaction.

The present invention relates to a monoclonal antibody or an antibody fragment thereof comprising a constant region, which is a monoclonal antibody or an antibody fragment thereof wherein one or more amino acid residues in the constant region are substituted with a Cys residue (hereinafter referred also to as a monoclonal antibody substituted with a Cys residue or an antibody fragment thereof).

An antibody is a heterodimer consisting of about 150 kDa and comprises a polypeptide of a heavy chain (hereinafter referred also to as H chain) and light chain (hereinafter referred also to as L chain). Also, the H chain comprises a variable region (hereinafter VH) and a constant region (CH) from the N-terminal side, and the L chain comprises a variable region (hereinafter referred also to as VL) and constant region (CL) from the N-terminal side. The CH further comprises each domains of CH1, hinge, CH2 and CH3 from the N-terminal side. In addition, the region comprising the CH2 and CH3 is called Fc region.

Examples of the class of the antibody include immunoglobulin G (IgG), immunoglobulin A (hereinafter referred also to as IgA), immunoglobulin E (hereinafter referred also to as IgE) and immunoglobulin M (hereinafter referred also to as IgM). As the monoclonal antibody or the antibody fragment of the present invention, IgG is preferable. In addition, examples of the subclass of IgG include IgG1, IgG2, IgG3 and IgG4.

Though the origin of the constant region of the monoclonal antibody of the present invention is not particularly limited, a mammal origin is preferable. Regarding the mammal, for example, an antibody and the like derived from human, mouse, rat, hamster or rabbit can be mentioned. The origin of the constant region of the monoclonal antibody or the antibody fragment thereof of the present invention is preferably human.

The constant region of antibody can be specified by the number of amino acid residues from the N-terminal based on the numbering by Kabat et al. (Kabat numbering) [*Sequences of Proteins of Immunological Interest*, Fifth Edition. NIH Publication No. 91, 3242 (1991)].

For example, the CL of human IgG1 is specified as an amino acid sequence from positions 108 to 211 in the Kabat numbering, and the CH1 is specified as an amino acid sequence from positions 118 to 215 in the EU numbering, the hinge domain is specified as an amino acid sequence from positions 216 to 230 in the EU numbering [*Sequences of Proteins of Immunological Interest*, Fifth Edition. NIH Publication No. 91, 3242 (1991)], the CH2 is specified as an amino acid sequence from positions 231 to 340 in the EU numbering and the CH3 is specified as an amino acid sequence from positions 341 to 447 in the EU numbering, respectively.

[Substitution to Cys Residues]

The monoclonal antibody or the antibody fragment of the present invention is a product in which one or more amino acid residues in a constant region of a naturally existing antibody (hereinafter referred also to as WT) are substituted with a Cys residue.

The substitution of one or more amino acid residues in a constant region into a Cys residue can be carried out using a conventionally known site-directed mutagenesis (*Molecular Cloning*, A Laboratory Manual, Second Edition, Cold Spring Harbor Laboratory Press (1989); *Current Protocols in Molecular Biology*, John Wiley & Sons (1987-1997); *Nucleic Acids Research*, 10, 6487 (1982); *Proc. Natl. Acad. Sci. USA,* 79, 6409 (1982); *Gene,* 34, 315 (1985); *Nucleic Acids Research,* 13, 4431 (1985); *Proc. Natl. Acad. Sci. USA,* 82, 488 (1985)).

For example, it is possible to prepare the monoclonal antibody or the antibody fragment thereof of the present invention by directly substituting one or more amino acids in a constant region of WT with a Cys residue, in the shape of a plasmid using QuickChange II Site-Directed Mutagenesis Kit (manufactured by Stratagene) and the like.

As another preparation method, it is also possible to prepare the monoclonal antibody or the antibody fragment of the present invention in which one or more amino acid residues in a constant region are substituted with a Cys residue, by designing a synthetic DNA sequence in which one or more amino acids in the constant region of WT were substituted with a Cys residue in advance, and digesting it with an appropriate restriction enzyme and inserting the product into an expression plasmid of the antibody or the antibody fragment thereof.

The amino acid residues to be substituted with a Cys residue in the present invention are amino acid residues located at a constant region of the antibody, preferably amino acid residues located at least at one of the CL and CH, and more preferably amino acid residues located at CH1.

Though the number of amino acid residues to be substituted with Cys residues according to the present invention is not particularly limited, it is preferably from one to scores, and more preferably from 1 to 20. In addition, it is preferably from one to several, for example, further preferably from 1 to 6 amino acids.

From another point of view, the amino acid residues in a constant region of WT to be substituted with a Cys residue have a solvent accessible surface area ratio of preferably 30% or less, more preferably 25% or less, and further preferably 20% or less. When amino acid residues having a solvent accessible surface area ratio of 30% or less are substituted with a Cys residue, it is expected that disulfide bond formation between the introduced Cys residue and other oxidation reactions hardly occur because the degree of structural exposure of the Cys residue is low.

The solvent accessible surface area can be easily calculated based on the DSSP program [*Biopolymers*, 22, 2577-2637 (1983)], using a crystalline structure analyzing data file of antibodies or antibody fragments registered in Protein data bank (PDB) (hereinafter referred also to as PDB file).

The ratio of the solvent accessible surface area of the amino acid residues of interest can be calculated by dividing the antibody structural solvent accessible surface area calculated in the above by the solvent accessible surface area of alanine-X-alanine (X represents the amino acid residues of interest). In this connection, there is a case in which two or more PDB files are present on one species of protein, and any one of them can be used in the present invention.

According to the present invention, when the class of the monoclonal antibody is human IgG, the monoclonal antibody or the antibody fragment of the present invention is specifically a monoclonal antibody or the antibody fragment which comprises a constant region in which at least one or more of amino acids selected from the following (1) to (6), in a constant region of WT, are substituted with a cysteine residue is preferable.

(1) the amino acid at position 124 of human IgG light chain region in Kabat numbering,
(2) the amino acid at position 198 of human IgG light chain region in Kabat numbering,
(3) the amino acid at position 201 of human IgG light chain region in Kabat numbering,
(4) the amino acid at position 140 of human IgG heavy chain region in EU numbering (the amino acid at position 138 of human IgG heavy chain region in Kabat numbering),
(5) the amino acid at position 147 of human IgG heavy chain region in EU numbering (the amino acid at position 145 of human IgG heavy chain region in Kabat numbering),
(6) the amino acid at position 183 of human IgG heavy chain region in EU numbering (the amino acid at position 188 of human IgG heavy chain region in Kabat numbering).

When the human IgG comprises a constant region in which at least one or more of amino acids, selected from the above (1) to (6) in the constant region of WT, are substituted with a cysteine residue, it can be modified by a chemical modification reaction with a high efficiency without depending on the amino acid sequence of variable regions and, furthermore, an antigen binding activity of same or higher than that of WT can be maintained.

That is, when it comprises a constant region in which at least one or more of amino acids, selected from the above (1) to (6) in the constant region of WT, are substituted with a cysteine residue, even if an antibody or antibody fragment is obtained by combining variable regions of any amino acid sequences, the thus obtained antibody or antibody fragment can be modified by a chemical modification reaction with a high efficiency.

In addition, since the substituted Cys residue is stably free and a pretreatment before the modification with PEG and the like is not necessary, these characters are very useful. Further, since the substituted Cys residue is stably free, there is an advantage that it is not easily affected by the formation of intermolecular disulfide bond, S-glutathione formation and the like.

It is preferable that the monoclonal antibody or the antibody fragment of the present invention maintains an antigen binding activity of same to or higher than that of the WT before substitution with Cys residues. The antigen binding activity can be measured by a method such as a binding assay, a fluorescent antibody technique [*Cancer Immunol. Immunother.*, 36, 373 (1993)], a surface plasmon resonance method which uses the Biacore system, and the like.

Examples of the monoclonal antibody or the antibody fragment of the present invention include a monoclonal antibody or the antibody fragment which recognizes a tumor-related antigen, a monoclonal antibody or the antibody fragment which recognizes an antigen related to an allergy or inflammation, a monoclonal antibody or the antibody fragment which recognizes an antigen related to a circulatory organ disease, a monoclonal antibody or the antibody fragment which recognizes an antigen related to an autoimmune disease, a monoclonal antibody or the antibody fragment which recognizes an antigen related to a viral or bacterial infection, and the like.

Examples of the tumor-related antigens include CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD56, CD59, CD63, CD64, CD66b, CD69, CD70, CD74, CD80, CD89, CD95, CD98, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, carbonic anhydrase 9 (CA9), cadherin, α-chemokine receptor (CCR)4, CCR7, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth facter receptor (EGFR), EGFRvIII, EGFR2 (HER2), EGFR3 (HER3), EGFR4 (HER4), endoglin, epithelial cell adhesion molecule (Ep-CAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR)3, FGFR4, FLT1, FLT3, folate receptor, Frizzled homologue 10 (FZD10), frizzled receptor 4 (FZD-4), G250, G-CSF receptor, ganglioside (such as GD2, GD3, GM2 and GM3), globo H, gp75, gp88, GPR-9-6, heparanase I, hepatocyte growth factor (HGF), HGF receptor, HLA antigen (such as HLA-DR), HM1.24, human milk fat globule (HMFG), hRS7, heat shock protein 90 (hsp90), idiotype epitope, insulin-like growth factor (IGF), IGF receptor (IGFR), interleukin (such as IL-6 and IL-15), interleukin receptor (such as IL-6R and IL-15R), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance type II receptor (MISIIR), mucin, neural cell adhesion molecule (NCAM), Necl-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (such as DR4 and DR5), system ASC amino acid transporter 2 (ASCT2), trkC, TROP-2, TWEAK receptor Fn14, type IV collagenase, urokinase receptor, vascular endothelial growth factor (VEGF), VEGF receptor (such as VEGFR1, VEGFR2 and VEGFR3), vimentin, VLA-4 and the like.

Examples of the antibody which recognizes a tumor-related antigen include anti-GD2 antibody [*Anticancer Res.*, 13, 331 (1993)], anti-GD3 antibody [*Cancer Immunol. Immunother.*, 36, 260 (1993)], anti-GM2 antibody [*Cancer Res.*, 54, 1511 (1994)], anti-HER2 antibody [*Proc. Natl. Acad. Sci. USA*, 89, 4285 (1992), U.S. Pat. No. 5,725,856], anti-CD52 antibody [*Proc. Natl. Acad. Sci. USA*, 89, 4285

(1992)], anti-MAGE antibody [*British J. Cancer*, 83, 493 (2000)], anti-HM1.24 antibody [*Molecular Immunol.*, 36, 387 (1999)], anti-parathyroid hormone-related protein (PTHrP) antibody [Cancer, 88, 2909 (2000)], anti-bFGF antibody, anti-FGF-8 antibody [*Proc. Natl. Acad. Sci. USA*, 86, 9911 (1989)], anti-bFGFR antibody, anti-FGF-8R antibody [*J. Biol. Chem.*, 265, 16455 (1990)], anti-IGF antibody [*J. Neurosci. Res.*, 40, 647 (1995)], anti-IGF-IR antibody [*J. Neurosci. Res.*, 40, 647 (1995)], anti-PSMA antibody [J. Urology, 160, 2396 (1998)], anti-VEGF antibody [*Cancer Res.*, 57, 4593 (1997)], anti-VEGFR antibody [*Oncogene*, 19, 2138 (2000), WO96/30046], anti-CD20 antibody [*Curr. Opin. Oncol.*, 10, 548 (1998), U.S. Pat. No. 5,736,137], anti-CD10 antibody, anti-EGFR antibody (WO96/402010), anti-Apo-2R antibody (WO98/51793), anti-ASCT2 antibody (WO2010/008075), anti-CEA antibody [*Cancer Res.*, 55(23 suppl): 5935s-5945s, (1995)], anti-CD38 antibody, anti-CD33 antibody, anti-CD22 antibody, anti-EpCAM antibody, anti-A33 antibody and the like.

Examples of the antibody which recognizes an allergy- or inflammation-related antigen include anti-interleukin 6 antibody [*Immunol. Rev.*, 127, 5 (1992)], anti-interleukin 6 receptor antibody [*Molecular Immunol.*, 31, 371 (1994)], anti-interleukin 5 antibody [*Immunol. Rev.*, 127, 5 (1992)], anti-interleukin 5 receptor antibody, anti-interleukin 4 antibody [*Cytokine*, 3, 562 (1991)], anti-interleukin 4 receptor antibody [*J. Immunol. Methods*, 217, 41 (1998)], anti-tumor necrosis factor antibody [*Hybridoma*, 13, 183 (1994)], anti-tumor necrosis factor receptor antibody [*Molecular Pharmacol.*, 58, 237 (2000)], anti-CCR4 antibody [*Nature*, 400, 776, (1999)], anti-chemokine antibody (Peri et al., *J. Immunol. Meth.*, 174, 249, 1994), anti-chemokine receptor antibody [*J. Exp. Med.*, 186, 1373 (1997)] and the like.

Examples of the antibody which recognizes a cardiovascular disease-related antigen includes anti-GpIIb/IIIa antibody [*J. Immunol.*, 152, 2968 (1994)], anti-platelet-derived growth factor antibody [*Science*, 253, 1129 (1991)], anti-platelet-derived growth factor receptor antibody [*J. Biol. Chem.*, 272, 17400 (1997)], anti-blood coagulation factor antibody [*Circulation*, 101, 1158 (2000)], anti-IgE antibody, anti-$\alpha_V\beta_3$ antibody, $\alpha_4\beta_7$ antibody and the like.

Examples of the antibody which recognizes virus- or bacterial infection-related antigen includes anti-gp120 antibody [*Structure*, 8, 385 (2000)], anti-CD4 antibody [*J. Rheumatology*, 25, 2065 (1998)], anti-CCR5 antibody, anti-verotoxin antibody [*J. Clin. Microbiol.*, 37, 396 (1999)], and the like.

Examples of the monoclonal antibody of the present invention include a recombinant antibody produced by a transformant into which an expression vector comprising an antibody gene, wherein one or more amino acid residues in a constant region of WT are substituted with Cys residues and the like. Examples of the recombinant antibody include an antibody produced using recombinant technology. Specific examples include a human chimeric antibody, a humanized antibody, a human antibody and the like.

A human chimeric antibody is an antibody which comprises VL and VH of an antibody derived from an animal other than a human, and CL and CH of a human antibody. As the animal other than a human, any kind of animal such as a mouse, a rat, a hamster or a rabbit can be used.

The human chimeric antibody can be produced by obtaining cDNAs encoding VL and VH from a monoclonal antibody-producing hybridoma derived from a non-human animal, inserting them into an expression vector for animal cell comprising DNAs encoding CL and CH of a human antibody in which one or more amino acid residue is substituted with Cys residue in a constant region of WT by optionally using the above method to thereby construct a human chimeric antibody expression vector, and then introducing the vector into an animal cell to express the antibody.

The human chimeric antibody can be produced by obtaining cDNAs encoding VL and VH from a monoclonal antibody-producing hybridoma, inserting them into an expression vector for animal cell comprising DNAs encoding CL and CH of a human antibody, substituting one or more amino acid residue with Cys residue in a constant region of WT by optionally using the above method to thereby construct a human chimeric antibody expression vector, and then introducing the vector into an animal cell to express the antibody.

As the CH of WT used for the human chimeric antibody, any CH can be used, so long as it belongs to human immunoglobulin (hereinafter referred to as hIg), and those belonging to the hIgG class are preferred, and any one of the subclasses belonging to the hIgG class, such as hIgG1, hIgG2, hIgG3 and hIgG4, can be used. In addition, as the CL of the human chimeric antibody, any CL can be used, so long as it belongs to the hIg class, and those belonging to the κ class or λ class can be used.

A humanized antibody is an antibody in which amino acid sequences of CDRs of VL and VH of a non-human animal antibody are grafted into appropriate positions of VL and VH of a human antibody and also called such as a human CDR-grafted antibody, a reshaped-antibody and the like.

The humanized antibody can be produced by constructing cDNAs encoding variable region (V region) in which the amino acid sequences of CDRs of VL and VH derived from a non-human animal antibody produced by a hybridoma which produces a non-human animal monoclonal antibody are grafted into framework (FR) of VL and VH of any human antibody, inserting each of them into a vector for expression of animal cell comprising genes encoding CL and CH of a human antibody in which one or more amino acid residues are substituted with Cys residues in a constant region of WT by optionally using the above method to thereby construct a vector for expression of humanized antibody, and introducing it into an animal cell to thereby express and produce the humanized antibody.

In addition, the humanized antibody can be produced by constructing cDNAs encoding V region in which the amino acid sequences of CDRs of VL and VH of an antibody derived from a non-human animal antibody produced by a hybridoma which produces a non-human animal monoclonal antibody are grafted into FR of VL and VH of any human antibody, inserting each of them into a vector for expression of animal cell comprising genes encoding CL and CH of a human antibody, further substituting one or more amino acid residues in a constant region of WT with Cys residues by optionally using the above method to thereby construct a vector for expression of humanized antibody, and introducing it into an animal cell to thereby express and produce the humanized antibody.

As the amino acid sequences of FRs of VL and VH of a human antibody, any amino acid sequences can be used, so long as they are amino acid sequences of VL and VH, respectively, derived from a human antibody. Examples include amino acid sequences of VL and VH of human antibodies registered in database such as Protein Data Bank, common amino acid sequences of each sub group of FRs of VL and VH of human antibodies described in, for example, *Sequences of Proteins of Immunological Interest*, US Dept. Health and Human Services (1991), and the like.

As the CH of WT used for the humanized antibody, any CH can be used, so long as it belongs to the hIg class, and those of the hIgG class are preferred and any one of the subclasses belonging to the hIgG class, such as hIgG1, hIgG2, hIgG3 and hIgG4 can be used.

As the CL of the human CDR-grafted antibody, any CL can be used, so long as it belongs to the hIg class, and those belonging to the κ class or λ class can be used.

A human antibody is an antibody in which one or more amino acid residues are substituted with Cys residues in a constant region of a WT antibody which naturally exists in the human body or an antibody obtained from a human antibody phage library or a human antibody-producing transgenic animal, which is prepared based on the recent advance in genetic engineering, cell engineering and developmental engineering techniques.

The antibody existing in the human body can be prepared, for example by isolating a human peripheral blood lymphocyte, immortalizing it by infecting with EB virus or the like, cloning it to culture lymphocytes capable of producing the antibody, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, by using its activity to bind to an antigen-immobilized substrate as the index. The antibody fragment can be converted into a human antibody molecule comprising two full H chains and two full L chains.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it [*Proc. Natl. Acad. Sci. USA*, 97, 722 (2000)].

A method for producing a human antibody from the human antibody-producing transgenic non-human animal comprises obtaining a human antibody-producing hybridoma by a hybridoma preparation method usually carried out in non-human mammals, culturing the obtained hybridoma and forming and accumulating the human antibody in the culture.

Furthermore, a human antibody can be produced by obtaining cDNAs encoding VL and VH from a human antibody-producing hybridoma, inserting them into an expression vector for animal cell comprising DNAs encoding CL and CH of the human antibody in which one or more amino acid residues in a constant region of WT are substituted with Cys residues by optionally using the above method to thereby construct a human antibody expression vector, and then introducing the vector into an animal cell to express the antibody.

Moreover, a human antibody can be produced by obtaining cDNAs encoding VL and VH from a human antibody-producing hybridoma, inserting them into an expression vector for animal cell comprising DNAs encoding CL and CH of the human antibody, substituting one or more amino acid residues in a constant region of WT are substituted with Cys residues by optionally using the above method to thereby construct a human antibody expression vector, and then introducing the vector into an animal cell to express the antibody.

As the CH of WT used for the human antibody, any CH can be used, so long as it belongs to hIg, and those belonging to the hIgG class are preferred, and any one of the subclasses belonging to the hIgG class, such as hIgG1, hIgG2, hIgG3 and hIgG4, can be used.

In addition, as the CL used for the human antibody, any CL can be used, so long as it belongs to the hIg class, and those belonging to the κ class or λ class can be used.

An antibody fragment is composed of a part of antibody. Examples of the antibody fragment of the present invention include an antibody fragment comprising a constant region, such as Fab, Fab', F(ab')$_2$, and the like.

In addition, the antibody fragment of the present invention includes an antibody fragment comprising a constant region, such as an antibody which lacks light chain derived from animals belonging to camelid species such as camel, dromedary, guanaco, alpaca and the like, a multispecific antibody fragment prepared by binding antibody fragments which recognize plural epitopes, a single chain peptide comprising an antigen binding region and a constant region, an antibody fragment comprising a constant region such as a heterodimmer and a homodimmer [*Trends Biotechnol.*, 21, 484 (2003), WO2004/058820] and the like.

A Fab is an antibody fragment having a molecular weight of about 50,000 and having antigen binding activity, in which the portion from the N-terminal side of H chain to CH1 and the entire L chain, among fragments obtained by treatment of an antibody with papain, are bound together through a disulfide bond.

In addition, as another embodiment, the Fab of the present invention can be produced by obtaining cDNA encoding a region consisting of the entire L region and the region comprising VH and CH1 derived from an antibody molecule, inserting them into an expression vector for a prokaryotic cell or an eukaryotic cell to thereby construct a Fab expression vector, and then introducing the vector into a procaryotic cell or an eukaryotic cell to express the antibody.

A F(ab')$_2$ is an antibody fragment having antigen binding activity and having a molecular weight of about 100,000 in which two Fab are bound in hinge region, among fragments obtained by treating the bottom parts of two disulfide bonds in hinge region of IgG with a protease, pepsin.

A F(ab')$_2$ of the present invention can be obtained by treating an monoclonal antibody with pepsin. In addition, it can be produced by forming a thioether bond or a disulfide bond between after-mentioned Fab's. Moreover, a F(ab')$_2$ can be produced by oxidizing Fab' of the present invention under an appropriate condition.

A Fab' is an antibody fragment having a molecular weight of about 50,000 and having antigen binding activity, which is obtained by cleaving a disulfide bond in the hinge region of the F(ab')$_2$. The Fab' of the present invention can be obtained by treating the F(ab')$_2$ of the present invention with a reducing agent such as dithiothreitol.

In addition, as another embodiment, the Fab' of the present invention can be produced by obtaining cDNA encoding a region consisting of the entire L region and a region comprising VH, CH1 and hinge region derived from an antibody molecule, inserting them into an expression vector for a procaryotic cell or an eukaryotic cell to thereby construct a Fab' expression vector, and then introducing the vector into a prokaryotic cell or an eukaryotic cell to express the antibody.

[Chemical Modification]

It is preferable that the monoclonal antibody or the antibody fragment of the present invention is a derivative in which one or more amino acids in a constant region are substituted with a Cys residue and at least one of the substituted Cys residues is chemically modified (hereinafter referred also to as a monoclonal antibody modified product or a antibody fragment modified product).

It is preferable that the above chemical modification is a chemical modification by a chemical modification reaction under non-reducing conditions. In addition, it is preferable that 40% or more of the above substituted Cys residues are chemically modified; and it is preferable that more preferably 60% or more, further preferably 70% or more, particularly preferably 80% or more, most preferably 85% or more of the above substituted Cys residues are chemically modified.

The aforementioned chemical modification by a chemical modification reaction under non-reducing conditions may be any chemical modification as long as it is a binding to a molecule having reactivity with the thiol group of Cys residue of the monoclonal antibody or the antibody fragment of the present invention.

The aforementioned molecule having reactivity with the thiol group of Cys residue may be any molecule as long as it has reactivity with the thiol group of Cys residue of the monoclonal antibody or the antibody fragment of the present invention. It is preferable that the aforementioned molecule having reactivity with the thiol group of Cys residue has a thiol reactive functional group having reactivity with the thiol group of Cys residue of the monoclonal antibody or the antibody fragment of the present invention.

Regarding the aforementioned thiol reactive functional group, it may be any molecule as long as it has reactivity with the thiol group of Cys residue of the antibody molecule. Examples of the thiol reactive functional group include maleimide, haloacetyl, iodoacetamide succinimidyl ester, isothiocyanate, sulfonyl chloride, 2,6-dichlorotriazinyl and the like.

[Hydrophilic Macromolecule or Amphipathic Macromolecule]

A molecule comprising a hydrophilic macromolecule or amphipathic macromolecule is preferable as the molecule having reactivity with the thiol group of Cys residue of the monoclonal antibody or the antibody fragment. Examples of the hydrophilic macromolecule or amphipathic macromolecule include polyoxy alkylene, polyol, a molecule containing polysaccharide, and the like.

Examples of the polyoxy alkylene include straight or branched chain PEG, polypropylene glycol, polypropylene ethylene glycol and the like.

Examples of the polyol include straight or branched chain polyglycerol and the like. Examples of the molecule containing a polysaccharide include homo- or heteropolysaccharides such as straight or branched chain amylose, dextran, pullulan, glycogen and the like, and the like.

Further, examples of the hydrophilic macromolecule or amphipathic macromolecule include macromolecules, for example, polyglutamic acid, polyaspartic acid, methyl cellulose, ethyl cellulose, propyl cellulose, ethyl methyl cellulose, hydroxy cellulose, hydroxy alkyl cellulose, hydroxy propyl methyl cellulose, hydroxy propyl starch, carboxy methyl starch, alkali metal carboxy methyl cellulose, alkali metal cellulose sulfate, a cellulose graft polymer, crosslinked gelatin, cellulose acetate phthalate, a starch-acrylic acid graft polymer, phthalic anhydride modified gelatin, succinic acid modified gelatin, polyvinyl alcohol, polyvinyl pyrrolidone, polyvinyl methyl ether, methyl vinyl ester, a salt of poly (meth)acrylic acid [e.g., sodium poly(meth)acrylate], a carboxyvinyl polymer, a vinyl pyrrolidone-ethyl (meth)acrylate copolymer, a vinyl pyrrolidone-styrene copolymer, a vinyl pyrrolidone-vinyl acetate copolymer, a polyvinyl acetate-(meth)acrylic acid (salt) copolymer, a polyvinyl acetate-crotonic acid copolymer, a vinyl acetate-(meth)acrylic acid copolymer, a vinyl acetate-crotonic acid copolymer, polyvinyl sulfonate, polyitaconic acid, polyhydroxyethyl (meth) acrylate, poly(meth)acrylamide, a styrene-maleic anhydride copolymer, a (meth)acrylamide-(meth)acrylic acid copolymer, poly(meth)acrylic acid (acrylate) copolymer such as potassium poly(meth)acrylate and sodium poly(meth)acrylate, saponification product of poly(meth)acrylonitrile, a (meth)acrylic acid (acrylate)/vinyl alcohol copolymer, starch/(meth)acrylic acid (acrylate) graft copolymer, a saponification product of starch/(meth)acrylonitrile graft copolymer, a cellulose/(meth)acrylic acid (acrylate) graft copolymer, poly(meth)acrylamide and its partially hydrolyzed product, polyvinyl alcohol, a neutralized product of starch-(meth)acrylic acid (acrylate) graft copolymer, sodium salt of vinyl acetate-methyl (meth)acrylate copolymer saponification product, an isobutylene-maleic anhydride copolymer, a polyvinyl alcohol-maleic acid ester system copolymer, a (meth)acrylamide-(meth)acrylic acid (acrylate) copolymer, a starch-poly(meth)acrylonitrile graft copolymer, polyalkylene oxide, vinyl ester-ethylene system unsaturated carboxylic acid copolymer, a poly(meth)acrylic acid, polyvinyl alcohol/anhydrous sodium maleate copolymer and the like.

Though the molecular weight of the molecule containing a hydrophilic macromolecule or amphipathic macromolecule is not particularly limited, it is preferably 500 Da or more, and more preferably from 500 Da to 100 kDa.

According to the present invention, reactivity in the chemical modification reaction can be obtained in accordance with the calculation method described in, for example, *J. Biochem.*, 115, 814 (1994). Examples of the calculation method of the reactivity include a method in which samples before and after the reaction with a hydrophilic macromolecule or amphipathic macromolecule are developed by non-reductive SDS-PAGE and the reactivity is calculated by GS-800 Calibrated Densitometer (manufactured by Bio-Rad), a method in which a samples after the reaction is subjected to gel filtration chromatography and the reactivity is calculated using the peak areas of the monoclonal antibody or the antibody fragment in which the substituted Cys residues are chemically modified and those are not reacted, and the like.

It is preferable that the aforementioned molecule containing a hydrophilic macromolecule or amphipathic macromolecule is a modification group which contains the aforementioned hydrophilic macromolecule or amphipathic macromolecule. It is more preferable that the modification group is a modification group containing a hydrophilic macromolecule or amphipathic macromolecule or a functional molecule. In addition, the modification group may be a modification group containing both of the hydrophilic macromolecule or amphipathic macromolecule and the functional molecule as described below.

(Functional Molecule)

As the molecule having the reactivity with the thiol group of Cys residue of the monoclonal antibody or the antibody fragment, a modification group containing a functional molecule is preferable. Examples of the functional molecule include a drug, a biologically active peptide, a biologically active protein, a nucleic acid, a radiolabeled compound, a sugar chain, a lipid, a fluorescent compound and the like.

Examples of the drug include an antitumor agent, an antibiotic, an antiviral agent and the like.

Examples of the antitumor agent include those which have cytotoxicity and cell growth inhibitory action based on a mechanism including kinase inhibition, cell cycle inhibition, DNA binding, DNA digestion, alkylation of DNA, tubulin binding inhibition, mitosis inhibition and the like, and the like.

Examples of the antitumor agent include antitumor agents calicheamicin, dolastatin, maytansinoid and duocarmycin and derivatives thereof, which are used in ADC [*Bioconjugate Chem.*, 21, 5 (2010)]; amifotine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), liposomal doxorubicin (doxil), gemcitabine (gemzal), daunorubicin, liposomal daunorubicin (daunoxome), procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, camptothecine, CPT-11, 10-hydroxy-7-ethyl-camptothecine (SN38), floxuridine, fludarabine, hydroxyurea, ifosfamide, idarubicin, mesna, irinoracan, mitoxantrone, topotecan, leuprolide, megestrol, melphalan, mercaptopurine, plicamycin, mitotane, pegaspargase, pentostatin, pipobroman, streptozocin, tamoxifen, teniposide, testolactone, thioguanine, thiotepa, uracil mustard, vinorelbine, chlorambucil, prednisolone, vindesine, nimustine, semustine, capecitabine, tomudex, azacitidine, UFT, oxazoloplatin, gefitinib (iressa), imatinib (STI571), amsacrine, all-trans retinoic acid, thalidomide, bexarotene (targretin), dexamethasone, anastorozole (arimidex) and leuplin and derivatives thereof and the like.

Examples of the antibiotic include compounds of penicillin system, cephem system, macrolide system, tetracycline system and the like and derivatives thereof, and the like. More specifically, examples include ampicillin, cefalexin, cefaclor, gentamicin, streptomycin, kanamycin, amphotericin, penicillin and cefazolin and derivatives thereof, and the like.

Examples of the antiviral agent include ganciclovir, acyclovir and the like and derivatives thereof and the like.

Examples of the aforementioned derivatives include a modified product in which an optional functional group is deleted, substituted, inserted or added, a modified product by a radioisotope, a drug, a sugar and the like, and the like, and it is preferable that these also have the similar activity to the unmodified low molecular compound.

Examples of the biologically active peptide or biologically active protein include a proteolytic enzyme; an amino acid degrading enzyme: enzyme such as hydrase, lyase, and isomerase; a toxin such as a bacterial toxin, and a plant toxin; an antibacterial peptide having cytotoxicity; a peptide having cell membrane binding property or cell membrane permeability; derivatives thereof and the like.

Specific examples include asparaginase, glutaminase, arginase, uricase, superoxide dismutase, lactoferrin, streptokinase, plasmin, adenosine deaminase, interleukin-1 to 24, interferon-α, interferon-β, interferon-γ, interferon-ω, interferon-τ, granulocyte colony-stimulating factor, erythropoietin, tumor necrosis factor, platelet increasing factor, klotho protein, leptin, fibroblast growth factor 1 to 19, midkine, calcitonin, epidermal growth factor, glucagon, insulin, insulin-like growth factor 1, osteogenic protein 1, stem cell growth factor, amylin, parathyroid hormone, plasminogen activators, vascular endothelial growth factor, transformation growth factors, glucagon-like peptides, growth hormone, natriuresis peptides, plasminogen, angiopoietin, angiostatin, endostatin, neocarzinostatin, hepatocyte growth factor, lysine, aflatoxin, *Pseudomonas* exotoxin, diphtheria toxin and cholera toxin and soluble receptors thereof and the like.

Examples of the peptide having cell membrane permeability include a basic peptide, an amphipathic peptide and a hydrophobic peptide. In addition, as another embodiment, a peptide having a transmembrane sequence is also included. Examples of the cell membrane permeable peptide are shown in Table 1.

TABLE 1

| Peptide | Amino Acid Sequence | Reference |
|---|---|---|
| Penetratin | RQIKIWFQNRRMKWKK (SEQ ID NO: 31) | J. Neurosci., 24, 10040, (2004) |
| Tat-derived peptide | GRKKRRQRRRPPQC (SEQ ID NO: 32) | J. Biol. Chem., 272, 16010, (1997) |
| Transportan | GWTLNSAGYLLKIN (SEQ ID NO: 33) | FASEB. J., 12, 67 (1998) |
| Arg9 | RRRRRRRRR (SEQ ID NO: 34) | J. Pep. Res., 56, 318 (2000) |
| Rev-derived peptide | TRQARRNRRRRWRERQR (SEQ ID NO: 35) | J. Biol. Chem., 276, 5836, (2001) |
| C105Y | CSIPPEVKFNKPFVYLI (SEQ ID NO: 36) | J. Biol. Chem., 281, 1233, (2006) |
| MTS peptide | KGEGAAVLLPVLLAAPG (SEQ ID NO: 37) | Cell, 50, 729 (1987) |

As another embodiment of the peptide, examples include a peptide having an endosome escaping function. The peptide relating to the endosome escape has been found in large numbers from viruses and bacteria, and it enables escape from endosome membrane based on a mechanism such as membrane fusion, collapse of membrane structure, formation of membranous pore by association, and the like [*Trends Biotech.*, 26, 267 (2008)]. Examples of the endosome escape peptide are shown in Table 2.

TABLE 2

| Peptide | Amino Acid Sequence | Reference |
|---|---|---|
| GALA | AALEALAEALEALAEALEALA EAAAAGGC (SEQ ID NO: 38) | Biochemistry, 26, 2964, (1987) |
| HA-2 | GLFGAIAGFIENGWEGMIDGW YG (SEQ ID NO: 39) | J. Biol. Chem., 269, 12918, (1994) |
| KALA | WEAKLAKALAKALAKHLAKAL AKALKACEA (SEQ ID NO: 40) | Biochemistry 36, 3008 (1997) |
| JTS-1 | GLFEALLELLESLWELLLLEA (SEQ ID NO: 41) | Gene Ther., 3, 448 (1996) |
| Histidine-rich | CHK$_6$HC (SEQ ID NO: 42) | Bioconjugate Chem., 11, 901, (2000) |

The nucleic acid may be any molecule as long as it is a nucleotide or a molecule in which a molecule having a function equivalent to the nucleotide is polymerized.

Examples of the nucleotide include naturally derived DNA and RNA. Also, examples of the molecule in which a molecule having a function equivalent to the nucleotide is polymerized include naturally derived or artificially synthesized various nucleotide derivatives. Examples of the nucleotide derivatives include an RNAi molecule (e.g., siRNA, microRNA and shRNA), an aptamer, a peptide nucleic acid, a nucleotide polymer in which at least one nucleotide is substituted with a molecule having a function equivalent to the nucleotide, and the like.

Examples of the molecule having a function equivalent to nucleotide include a nucleotide derivative and the like. As the nucleotide derivative, it may be any molecule as long as it is a molecule in which a modification is applied to the nucleotide. For example, a molecule in which a modification is applied to a ribonucleotide or deoxyribonucleotide for the purpose of improving nuclease resistance, stabilizing, increasing affinity with complementary chain nucleic acid, increasing cell permeability, or effecting visualization in comparison with RNA or DNA is preferred.

Examples of the nucleotide derivative include a sugar moiety modified nucleotide, a phosphodiester bond modified nucleotide, a base modified nucleotide, a nucleotide in which at least one of the sugar moiety, phosphodiester bond and base is modified, and the like.

As the sugar moiety modified nucleotide, it may be any substance in which a part or all of chemical structure of the sugar of nucleotide is modified or substituted with an arbitrary substituent or substituted with an arbitrary atom, but a 2'-modified nucleotide is preferable.

Examples of the 2'-modified nucleotide include a 2'-modified nucleotide in which the 2'-OH group of ribose is substituted with a substituent selected from the group of H, $OR^3$, $R^3$, $R^{3'}OR^3$, SH, $SR^3$, $NH_2$, $NHR^3$, $NR^3_2$, $N^3$, CN, F, Cl, Br and I ($R^3$ represents alkyl or aryl, preferably alkyl having from 1 to 6 carbon atoms, and $R^{3'}$ represents alkylene, preferably alkylene having from 1 to 6 carbon atoms), and among them, it is preferable that the 2'-OH group is F or a methoxy group.

Also examples of the 2'-modified nucleotide include a 2'-modified nucleotide substituted with a substituent selected from the group consisting of a 2-(methoxy)ethoxy group, a 3-aminopropoxy group, a 2-[(N,N-dimethylamino)oxy]ethoxy group, a 3-(N,N-dimethylamino)propooxy group, a 2-[2-(N,N-dimethylamino)ethoxy]ethoxy group, a 2-(methylamino)-2-oxoethoxy group, a 2-(N-methylcarbamoyl)ethoxy group and a 2-cyano ethoxy group.

In addition, examples of the sugar moiety modified nucleotide include bridged nucleic acid (BNA) having two ring structures prepared by introducing a bridge structure into a sugar moiety.

Specific examples of the sugar moiety modified nucleotide include locked nucleic acid (LNA) in which the oxygen atom at 2' position and the carbon atom at 4' position are bridged via methylene, ethylene bridged nucleic acid (ENA) [*Nucleic Acid Research*, 32, e175 (2004)] and the like. In addition, examples also include peptide nucleic acid (PNA) [*Acc. Chem. Res.*, 32, 624 (1999)], oxypeptide nucleic acid (OPNA) [*J. Am. Chem. Soc.*, 123, 4653 (2001)], peptide ribonucleic acid (PRNA) [*J. Am. Chem. Soc*, 122, 6900 (2000)] and the like.

The phosphodiester bond modified nucleotide may be any substance in which a part or all of chemical structure of the phosphodiester bond of nucleotide is modified or substituted with an arbitrary substituent or substituted with an arbitrary atom.

Examples of the phosphodiester bond modified nucleotide include a nucleotide in which the phosphodiester bond is substituted with a phosphorothioate bond, a nucleotide in which the phosphodiester bond is substituted with a phosphorodithioate bond, a nucleotide in which the phosphodiester bond is substituted with an alkylphosphonate bond, a nucleotide in which the phosphodiester bond is substituted with a phosphoroamidate bond, and the like.

The base modified nucleotide may be any substance in which a part or all of chemical structure of the base of nucleotide is modified or substituted with an arbitrary substituent or substituted with an arbitrary atom.

Examples of the aforementioned base modified nucleotide include those in which an oxygen atom in a base is substituted with a sulfur atom, in which a hydrogen atom is substituted with an alkyl group having from 1 to 6 carbon atoms, in which a methyl group is substituted with hydrogen or an alkyl group having from 2 to 6 carbon atoms, and in which an amino group is protected with a protecting group such as an alkyl group having from 1 to 6 carbon atoms or an alkanoyl group having from 1 to 6 carbon atoms.

Further, examples of the nucleotide derivatives include those in which other chemical substances such as lipid, phospholipid, phenazine, folate, phenanthridine, anthraquinone, acridine, fluorescein, Rhodamine, cumarin or a pigment are added to a nucleotide or nucleotide derivatives in which at least one of its sugar moiety, a phosphodiester bond and a base is modified.

Specific examples of the nucleotide derivatives include 5'-polyamine added nucleotide derivatives, cholesterol added nucleotide derivatives, steroid added nucleotide derivatives, bile acid added nucleotide derivatives, vitamin added nucleotide derivatives, Cy5 added nucleotide derivatives, Cy3 added nucleotide derivatives, 6-FAM added nucleotide derivatives, Alexa Fluor added nucleotide derivatives, biotin added nucleotide derivatives and the like.

In addition, the nucleotide derivatives may form, with other nucleotides or nucleotide derivatives in a nucleic acid, a bridged structure such as an alkylene structure, a peptide structure, a nucleotide structure, an ether structure or an ester structure or a structure which is combined with at least one of these.

The nucleic acid to be used in the present invention may have any length as long as a nucleic acid comprising a partial nucleotide sequence of the target gene can form a double strand with another nucleic acid consisting of a nucleotide sequence complementary to the nucleotide sequence of the nucleic acid, but in general, the length of sequences that can form the double strand is preferably 15 to 27 bases, more preferably 15 to 25 bases, further preferably 15 to 23 bases, particularly preferably 15 to 21 bases, most preferably 15 to 19 bases.

As the nucleic acid to be used in the present invention, a nucleic acid consisting of a partial nucleotide sequence of the target gene is used, and among the nucleic acid, those in which preferably 1 to 3 bases, more preferably 1 or 2 bases, further preferably one base, is deleted, substituted or added may be used.

As the nucleic acid which inhibits expression of the target protein, any nucleic acid of a single-stranded nucleic acid, a double-stranded nucleic acid and the like can be used, as long as it comprises a partial nucleotide sequence of the target gene and another nucleic acid consisting of a nucleotide sequence complementary to the nucleotide sequence of the nucleic acid and is a nucleic acid which inhibits expression of the target protein, but a double-stranded nucleic acid is preferable.

According to the present invention, the double-stranded nucleic acid means a nucleic acid which has a double-strand forming moiety in which two chains form a pair. The double-strand forming moiety is a moiety in which nucleotides constituting a double-stranded nucleic acid or derivatives thereof are form a double strand by constituting base pairs. In general, the double strand forming moiety is constituted with preferably 15 to 27 base pairs, more preferably 15 to 25 base pairs, further preferably 15 to 23 base pairs, particularly preferably 15 to 21 base pairs, most preferably 15 to 19 base pairs.

In general, the single-stranded nucleic acid which constitutes the double-stranded nucleic acid consists of preferably 15 to 30 bases, more preferably 15 to 29 bases, further preferably 15 to 27 bases, more further preferably 15 to 25 bases, particularly preferably 17 to 23 bases, most preferably 19 to 21 bases.

When the double-stranded nucleic acid of the present invention has an additional nucleotide or nucleotide derivatives which do not form a double strand, on the 3'-side or 5'-side next to the double strand forming moiety, it is called a protruding part (overhang). When the double-stranded nucleic acid has a protruding part, the nucleotide which constitutes the protruding part may be a ribonucleotide, a deoxyribonucleotide or derivatives thereof.

As the double-stranded nucleic acid having a protruding part, those which have a protruding part consisting of preferably from 1 base to 4 bases, more preferably 1 to 3 bases, further preferably 2 bases, on the 3' end or the 5' end of at least one of the chains, are preferably used. As the protruding part consisting of 2 bases, a protruding part consisting of dTdT or UU is preferable.

According to the double-stranded nucleic acid, the antisense chain alone and both of the antisense chain and sense chain can have the protruding part, but it is preferable that both of the antisense chain and sense chain have the protruding part.

In addition, it is possible to use a sequence which partly or entirely coincides with the target sequence, next to the double strand forming moiety, or a sequence that coincides with the nucleotide sequence of complementary chain of the target sequence, next to the double strand forming moiety.

Further, as the double-stranded nucleic acid of the present invention, for example, the nucleic acid molecule which forms the above-mentioned double-stranded nucleic acid by the action of ribonuclease such as Dicer (International Publication No. 2005/089287), a double-stranded nucleic acid which does not have the 3' end or the 5' end protruding part, and the like can also be used.

As the double-stranded nucleic acid according to the present invention, a nucleic acid consisting of the nucleotide sequence of the target gene or of the same sequence of the nucleotide sequence of its complementary chain may be used, but a double-stranded nucleic acid consisting of a nucleic acid, in which 1 to 4 bases of the 5' end or 3' end of at least one chain of the nucleic acid are eliminated and a nucleic acid consisting of a nucleotide sequence complementary to the nucleotide sequence of the nucleic acid, may also be used. As the double-stranded nucleic acid, for example, a double-stranded nucleic acid in which the double bond forming moiety consists of 15 to 19 base pairs can be mentioned.

In addition, a single-stranded nucleic acid can also be used as the nucleic acid of the present invention.

As the nucleic acid of the present invention, it may be a single-stranded nucleic acid prepared by connecting the sense chain and antisense chain of the above-mentioned double-stranded nucleic acid via a spacer sequence. It is preferable that the single-stranded nucleic acid is a single-stranded nucleic acid such as shRNA which has a double strand forming moiety formed by a stem loop structure. It is preferable that the single-stranded nucleic acid having a stem loop structure generally has a length of 50 to 70 bases.

As the nucleic acid of the present invention, it may be a nucleic acid having a length of preferably 70 bases or less, more preferably 50 bases or less, still more preferably 30 bases or less, which is designed such that it forms the above-mentioned single-stranded nucleic acid or double-stranded nucleic acid by the activity of ribonuclease and the like.

The method for producing a nucleic acid according to the present invention is not particularly limited, and examples include a method which uses a conventionally known chemical synthesis, an enzymatic transcription method and the like. Examples of the method which uses a conventionally known chemical synthesis include a phosphoamidite method, a phosphorothioate method, a phosphotriester method, a CEM method [*Nucleic Acid Research*, 35, 3287 (2007)] and the like, and it can be synthesized by such as ABI 3900 High Throughput Nucleic Acid Synthesizer (manufactured by Applied Biosystems). After completion of the synthesis, elimination from the solid phase, deprotection of the protecting group, purification of the product of interest and the like are carried out.

It is preferable to obtain a nucleic acid having a purity of preferably 90% or more, more preferably 95% or more by the purification. In the case of a double-stranded nucleic acid, annealing may be carried out after mixing the synthesized and purified sense chain and antisense chain at an appropriate ratio, such as at preferably 0.1 to 10 equivalents, more preferably 0.5 to 2 equivalents, further preferably 0.9 to 1.1 equivalents, particularly preferably equimolar amount, of the sense chain per 1 equivalent of the antisense chain, or the mixture may be directly used by avoiding the step for carry out annealing.

The annealing may be carried out under any conditions as long as they are a conditions under which the double-stranded nucleic acid can be formed, and in general, it is carried out by mixing the sense chain and antisense chain at almost equimolar amounts, heating at about 94° C. for about 5 minutes, and then slowly cooling to room temperature.

Examples of the enzymatic transcription method for producing the nucleic acid of the present invention include a method by transcription with a phage RNA polymerase (e.g., T7, T3 or SP6 RNA polymerase) and by using a plasmid or DNA having the nucleotide sequence in interest as the template.

The RNAi molecule is a single-stranded or double-stranded nucleic acid molecule which contains an antisense chain having a nucleotide sequence complementary to the mRNA encoding the target protein. The RNAi molecule inhibits expression of the target protein (protein synthesis) through specific binding of the antisense chain to the mRNA encoding the target protein. Examples of the RNAi molecule of the present invention include siRNA, microRNA and shRNA.

The siRNA is a low molecular double-stranded RNA prepared by hybridizing an antisense chain having a nucleotide sequence complementary to the mRNA encoding the target protein with a sense chain complementary to the antisense chain.

The microRNA (miRNA) is a low molecular non-coding RNA relating to the posttranscriptional regulation of gene expression by its interaction with a homologous mRNA, and regulates expression of a gene by binding to the complementary region of the target mRNA derived from the protein coding gene.

The shRNA is a single-stranded RNA in which the above-mentioned antisense chain and sense chain are connected via a linker moiety and forms a double-stranded chain moiety since the linker moiety forms a loop to fold and thereby hybridize the antisense chain and the sense chain.

In a specific embodiment, the siRNA and the microRNA can be formed by processing of a further longer double-stranded RNA, such as processing in the presence of enzyme Dicer or Drosha. The Dicer and Drosha are an RNAseIII-like nuclease which specifically digests dsRNA. A method for using the Dicer and other RNAi enzymes and the composition are described in US Patent Publication No. 2004/0086884.

The RNAi molecule of the present invention can be designed by a conventionally known technique such as siRNA Design Support System (manufactured by Takara Bio Inc.) based on the nucleotide sequence of the target protein.

The aptamer is a nucleic acid ligand of RNA or DNA which binds to a specific molecule of a protein.

The aptamer can be prepared by producing a library containing various nucleic acid chains and selecting a nucleic acid chain which can bind to a target protein from them. Examples of a suitable method for identifying the aptamer include Systematic Evolution of Ligands by Exponential Enrichment (SELEX™) method (U.S. Pat. No. 5,270,163).

As another embodiment of nucleic acid, the 3' end and the 5' end of an oligonucleotide can be modified for the purpose of applying it to conjugate preparation. Such a modification may be introduced at the 3' end or the 5' end of the molecule or both of them. The modification can include modification or substitution of the whole terminal phosphoric acid or one or more atoms of the phosphate group.

For example, the 3' end and the 5' end of an oligonucleotide can be bound to other functional molecule substance such as a fluorophore (e.g., pyrene, TAMRA, fluorescein, Alexa Fluor, Cy3 or Cy5 dye) or a protecting group (e.g., based on a sulfur group, a silicon group, a boron group or an ester group). The functional molecule substance can be linked to a sugar via a phosphoric group and/or a spacer.

A terminal atom of the spacer can be linked to the coupling atom of a phosphate group or C-3' or C-5'O, N, S or C group of the sugar, or these can be substituted. Alternatively, the spacer can be linked to the terminal atom of a substitute nucleotide (e.g., PNA), or this can be substituted.

Examples of the aforementioned spacer or linker include —$(CH_2)_n$—, —$(CH_2)_nN$—, —$(CH_2)_nO$—, —$(CH_2)_nS$—, $O(CH_2CH_2O)_nCH_2CH_2OH$ (e.g., n=3 or 6), non-base sugar, amido, carboxy, amine, oxyamine, oxyimine, thioether, disulfide, thiourea, sulfonamide or morpholino, or a biotin reagent and a fluorescein reagent.

In addition, as another embodiment of the nucleic acid, a Cys residue-substituted antibody modified product or the antibody fragment modified product can be converted into a complex via a non-covalent bond.

The radioactive labeling compound may be any nuclear species to be used in the diagnostic or therapeutic applications, and its examples include $^3H$, $^{14}C$, $^{32}P$, $^{33}P$, $^{35}S$, $^{51}Cr$, $^{57}CO$, $^{18}F$, $^{153}Gd$, $^{159}Gd$, $^{68}Ge$, $^{166}Ho$, $^{115}In$, $^{113}In$, $^{112}In$, $^{111}In$, $^{131}I$, $^{125}I$, $^{123}I$, $^{121}I$, $^{140}La$, $^{177}Lu$, $^{54}Mn$, $^{99}Mo$, $^{103}Pd$, $^{142}Pr$, $^{149}Pm$, $^{186}Re$, $^{188}Re$, $^{105}Rh$, $^{97}Ru$, $^{153}Sm$, $^{47}Sc$, $^{75}Se$, $^{85}Sr$, $^{99}Tc$, $^{201}Ti$, $^{113}Sn$, $^{117}Sn$, $^{133}Xe$, $^{169}Yb$, $^{175}Yb$, $^{90}Y$, $^{65}Zn$ and the like and compounds containing the above-mentioned nuclear species. In addition, molecules chelated with the above-mentioned nuclear species, such as POTA, PA-DOTA, TRITA, or DTPA, are also included in the radioactive labeling compound of the present invention.

Examples of the sugar chain include monosaccharides, disaccharides, oligosaccharides and the like including fucose, mannose, glucose, allose, altrose, gulose, idose, galactose, talose, ribose, arabinose, xylose, lyxose, erythose, erythrose, threose, cellobiose, maltose, isomaltose, lactose, lipoarabinomannan, a Lewis X-type trisaccharide, a sialyl Lewis X-type tetrasaccharide and the like.

Examples of the lipid include esters of fatty acids with various alcohols and simple lipids (neutral lipids) as their analogous substances. Examples include oil and fat (e.g., triacylglycerol), wax (fatty acid ester of higher alcohol); fatty acid ester such as a sterol ester, a cholesterol ester, a vitamin fatty acid and the like, a complex lipid having a polar group such as phosphoric acid, sugar, sulfuric acid, or amine in addition to the fatty acids and alcohols, such as phospholipid (glycerophospholipid, sphingophospholipid and the like) and glycolipid (glyceroglycolipid, sphingoglycolipid and the like), and, among compounds formed by hydrolysis of simple lipids or complex lipids, derived lipids which show fat-solubility, such as a fatty acid, a higher alcohol, a fat-soluble vitamin, a steroid, a carbohydrate and the like.

Examples of the fluorescence compound include fluorescence dyes such as of fluorescein series, Rhodamine series, Cy3, Cy5, eosin series, Alexa Fluor series, NBD series and the like, and fluorescent protein such as green fluorescence protein (GFP) and the like, and the like.

The hydrophilic macromolecule or amphipathic macromolecule and functional molecule may be linked directly or via an appropriate linker, and examples of the linker include ester, disulfide, hydrazone, dipeptide and the like. Examples of the modification group containing dipeptide include the modification groups described in WO96/35451.

Examples of the modified product when the modification group is a functional group include a monoclonal antibody represented by a formula 1: X-L-Y (1) [in the formula, X represents the monoclonal antibody substituted with a Cys residue or the antibody fragment thereof of the present invention, Y represents a functional molecule and L represents a linker which forms a covalent bond of the thiol group of substituted Cys residue of X and the functional molecule Y], wherein a formula 2: -L-Y (2) [in the formula, all symbols represent the same meanings as the above] is bound with the monoclonal antibody substituted with a Cys residue or the antibody fragment thereof of the present invention as the modification group.

The hydrophilic macromolecule or amphipathic macromolecule may be linked to the functional molecule as the linker in formula 1.

The linker L means a moiety derived as a bifunctional molecule from formula 3: R'-L'-R" [in the formula, R' and R" are the same or different and each represents —$NH_2$, —$CO_2H$, —OH, $OR^1$ (in the group, $R^1$ is a hydroxy protecting group), —$CO_2R^2$ (in the group, $R^2$ represents a functional group such as 2-hydroxypyridine, N-hydroxysuccinimide, p-nitrophenyl, pentafluorophenyl (Pfp) or Me) or other active ester, acylimidazole, maleimide, trifluoro acetate, diketone, imido ester, sulfonate ester, imine, —CHO, 1,2-cyclohexanedione, glyoxal, sulfonyl halide, α-halogenated ketone, azide and the like, and L' represents alkyl or a substituted alkyl group].

The alkyl chain L' can be substituted with a general substituent group such as halogen (e.g., I, Br, Cl or F), hydroxy, cyano, phenyl, amino, carboxy, alkyl, or alkoxy. In addition, the alkylene chain of linker L' can be blocked with one or two or more divalent groups such as —O—, —S—, —NH—, —CH=CH—, —C≡C—, phenyl, or —$SO_2$—.

The linker L' can have a branch type structure and can be linked in parallel with two or more functional molecules. However, the functional group R' has to form a covalent bond with the substituted Cys residue of the Cys residue-substituted monoclonal antibody or the antibody fragment of the present invention under appropriate conditions, and R" has to form a covalent bond with a functional molecule under appropriate conditions.

Also, as another embodiment of the linker L', those which have a binding mode which is digested inside the cells are also included. In a preferable embodiment, it is digested 10-fold or more faster, preferably 100-fold or more faster, in comparison with the case in blood. The structural mode of the linker which is easy to be digested is characterized by its high sensitivity to pH, oxidation reduction potential or a degrading enzyme as typified by a phosphatase, an esterase, a peptidase or a protease.

It is preferable that the pH-sensitive digestive linker has a binding mode which is digested under acidic conditions, preferably at pH 6.5 or lower, more preferably at pH 6.0 or lower, further preferably at pH 5.5 or lower. While pH in blood is 7.4, it is preferable that it is within a slightly lower range of from 7.1 to 7.3 in the cell. Further, it is preferable that pH is from 5.5 to 6.0 in endosome and it is preferable that it shifts to more acidic conditions to be about 5.0 in lysosome. As the pH-sensitive binding mode, a hydrazone bond is known.

The oxidation reduction potential-sensitive digestive linker has a binding mode of being digested under intracellular reduction environment. In the cells, since a reduction type tripeptide (glutathione) is present at a high concentration of from 1 mmol/l to 10 mmol/l, a reduction environment is formed. As the binding mode having a sensitivity under the reduction environment, a disulfide bond is known.

As the binding mode having sensitivity to a phosphatase, a phosphoester is known. As the binding mode having sensitivity to esterase, an ester bond is known.

As the binding mode having sensitivity to a peptidase or a protease, such an intracellular peptidase, or such as a lysosomal protease or an endosomal protease, there is known an oligopeptide or polypeptide constituted from an amino acid sequence which is recognized by a specific enzyme. As the enzyme, cathepsin B, C and D are known, and two or more species of dipeptide digesting sequence are present, though not limited thereto.

In a specific embodiment, the linker can be a dipeptide linker such as valine-citrulline (val-cit) or phenylalanine-lysine (phe-lys) linker.

As another embodiment, it is possible that two or more of the functional molecule Y are connected in series or in parallel via the linker L, which may be a combination of different functional molecules, and further, it is possible to change their order optionally. In addition, as still another embodiment, it is possible to connect it directly with a functional molecule without a linker.

In addition, by connecting the thiol group of the substituted Cys residue of the monoclonal antibody substituted with a Cys residue or the antibody fragment thereof to an appropriate functional group of the aforementioned functional molecule, the Cys residue can be chemically modified.

That is, according to the aforementioned method, the Cys residue can be chemically modified by connecting a connecting group to either one of the monoclonal antibody substituted with a Cys residue or the antibody fragment thereof prepared in advance or the functional molecule prepared in advance, and subsequently connecting the remaining one to the connecting group.

In another embodiment, an appropriate connecting group precursor may be connecting to the monoclonal antibody substituted with a Cys residue or the antibody fragment thereof prepared in advance and the functional molecule prepared in advance. Subsequently, the Cys residue can be chemically modified by allowing the two precursors to react.

The molecular weight of one modification group in the antibody modified product substituted with a Cys residue or the antibody fragment modified product is not particularly limited, and is preferably 500 Da or more, such as from 500 Da to 100 kDa.

Examples of the above-mentioned modification group include maleimide-polyethylene glycol-valine-citrulline-adriamycin (Maleimide-PEG-Val-Cit-ADM) and the like.

(Cytotoxicity)

It is preferable that the monoclonal antibody substituted with a Cys residue and the antibody fragment thereof are a monoclonal antibody having a cytotoxicity and the antibody fragment. In this case, examples of the cytotoxicity include antibody-dependent cellular cytotoxicity (ADCC activity), complement-dependent cytotoxicity (CDC) and the like.

Examples of the monoclonal antibody having ADCC activity and the antibody fragment thereof include a monoclonal antibody which comprises a complex-type N-glycoside-linked sugar chain in Fc region, wherein the ratio of sugar chains in which fucose is not bound to N-acetylglucosamine in the reducing terminal of the sugar chains among the total complex-type N-glycoside-linked sugar chains which bind to the Fc region contained in the composition is 20% or more (WO00/61739, WO02/31140), and comprises a constant region in which one or more amino acids in a constant region of WT are substituted with a Cys residue; and the antibody fragment thereof.

Examples of the monoclonal antibody having CDC activity and the antibody fragment thereof include a monoclonal antibody in which a polypeptide comprising a CH2 domain in the Fc region of a human IgG1 antibody is replaced by a polypeptide comprising an amino acid sequence which corresponds to the same position of a human IgG3 antibody based on the EU numbering in Kabat, et al. (WO2008/090958) and comprises a constant region in which one or more amino acids in a constant region of WT are substituted with a Cys residue; and the antibody fragment thereof.

Examples of the monoclonal antibody having CDC activity and the antibody fragment thereof include a monoclonal antibody which is a human IgG1 antibody, comprises a CH2 domain in which amino acids at positions 276 and 339 based on the EU numbering as in Kabat, et al. are replaced by other amino acids and has more improved complement-dependent cytotoxic activity (WO2008/090959) and comprises a constant region in which one or more amino acids in a constant region of WT are substituted with a Cys residue; and the antibody fragment thereof.

The CDC activity, ADCC activity of the monoclonal antibody substituted with a Cys residue or the antibody fragment thereof to cultured cell line which is antigen-positive can be evaluated using a known method [*Cancer Immunol. Immunother.*, 36, 373 (1993)].

(Producing Method)

The monoclonal antibody substituted with a Cys residue or the antibody fragment thereof of the present invention can be obtained by, for example, expressing them in a host cell as described below using a method described in *Molecular Cloning*, Second Edition; *Current Protocols in Molecular Biology; Antibodies*, A Laboratory manual, Cold Spring Harbor Laboratory (1988); *Monoclonal Antibodies*: principles and practice, Third Edition, Acad. Press (1993); *Antibody Engineering*, A Practical Approach, IRL Press at Oxford University Press (1996) and the like.

An monoclonal antibody modified product or an antibody fragment modified product can be obtained by preparing the monoclonal antibody substituted with a Cys residue or the antibody fragment thereof of the present invention and then chemically modifying the Cys residue of the monoclonal antibody or the antibody fragment.

1. Construction of Expression Vector of Monoclonal Antibody Substituted with Cys Residue or the Antibody Fragment Thereof (1) Construction of Expression Vector of Monoclonal Antibody Substituted with Cys Residue or the Antibody Fragment Thereof As the host cell for producing the monoclonal antibody substituted with a Cys residue or the antibody fragment thereof of the present invention, it includes any host cell which is generally used in the recombinant protein production.

The expression vector to be used in the expression of the substituted monoclonal antibody substituted with a Cys residue or the antibody fragment thereof of the present invention can be used depending on the purpose or by optionally selecting a substance suited for the host cell into which the expression vector is introduced.

When the expression vector is a recombinant vector, the recombinant vector contains DNAs encoding CL and CH connected to an appropriate promoter, preferably contains a transcription termination signal, namely a terminator region, in downstream of the polynucleotide of the present invention.

In addition, the recombinant vector can further contain a selectable marker gene for selecting a transformant (e.g., a drug resistance gene, a gene for complementing auxotrophic mutation, and the like). Also, it may contain a sequence which encodes a tag sequence useful for separating and purifying the expressed protein, and the like.

An expression cassette containing light chain and heavy chain of the antibody gene can be integrated into both of an antibody expression vector for prokaryotic cells and an antibody expression vector for eukaryotic cells, by inserting an appropriate restriction enzyme recognition sequence into both terminals of it.

In another embodiment, it may be an expression vector designed for such a manner that a variable region alone can be introduced later by an appropriate restriction enzyme, in order to construct an expression vector which can apply for various antibody variable regions.

When a prokaryotic cell such as *Escherichia coli* is used as the host cell, any expression vector can be used as long as it can integrate and express a gene encoding the above-mentioned antibody. Examples include pFLAG-CTS [manufactured by SIGMA, *Journal of Molecular Recognition*, 5, 15 (2002)], pET26b [manufactured by Novagen, *Molecular Immunology*, 8, 44 (2007)], pFab1, pFab2 and pFab3 [*Protein Expression and Purification*, 2, 34 (2004)] and the like.

Examples of the promoter to be used in the expression vector for prokaryotic cells include Tac promoter [*Journal of Molecular Recognition*, 5, 15 (2002)], rhamnose promoter [*Journal of Molecular Biology*, 234 (1993)] and the like.

In addition, the aforementioned vector may contain a signal sequence for polypeptide secretion. An example of the signal sequence for instructing secretion of a polypeptide into periplasm in *Escherichia coli* is PelB signal sequence [*J. Bacteriol.*, 169, 4379 (1987)].

For example, when *Escherichia coli* is the host cell and a vector is amplified and produced in a large amount in *Escherichia coli* (e.g., JM109, DH5α, HB101 or XL1Blue), it is necessary that the vector has an "ori" for amplifying in *Escherichia coli* and a marker gene for selecting a transformed *Escherichia coli* (e.g., a drug resistance gene selected by a drug such as ampicillin, tetracycline, kanamycin, chloramphenicol and the like). Examples of the marker gene include a vector of M13 series, a vector of pUC series, pBR322, pBluescript and the like.

When an animal cell is used as a host cell among eukaryotic cells, the expression vector for animal cell may be any vector, so long as the gene encoding the above monoclonal antibody substituted with a Cys residue or the antibody fragment thereof can be introduced and expressed.

Examples of the expression vector include pKANTEX93 [*Mol. Immunol.*, 37, 1035 (2000)], pAGE107 [Japanese Published Unexamined Patent Application 22979/91, Cytotechnology, 3, 133-140 (1990)], pAGE103 [*J. Biochem.*, 101, 1307 (1987)], pHSG274 [Gene, 27, 223 (1984)], pKCR [*Proc. Natl. Acad. Sci. U.S.A.*, 78, 1527 (1981)], N5KG1-Val Lark vector [*IDEC Pharmaceuticals*, a modified vector of N5KG1 (U.S. Pat. No. 6,001,358)], pSG1βd2-4 [*Cytotechnology*, 4, 173 (1990)] and the like.

The promoter and enhancer used for the expression vector for animal cell include, for example, SV40 early promoter and enhancer [*J. Biochem.*, 101, 1307 (1987)], LTR of Moloney mouse leukemia virus [*Biochem. Biophys. Res. Commun.*, 149, 960 (1987)], immunoglobulin H chain promoter [*Cell*, 41, 479 (1985)] and enhancer [*Cell*, 33, 717 (1983)] and the like.

When yeast is used as the host cell, for example, YEP13 (ATCC 37115), YEp24 (ATCC 37051), YCp50 (ATCC 37419), and the like can be used as the expression vector.

As the promoter, any promoters capable of expressing in yeast strains can be used. For example, the suitable promoters include promoters of genes of the glycolytic pathway such as hexosekinase, PHO5 promoter, PGK promoter, GAP promoter, ADH promoter, gal 1 promoter, gal 10 promoter, heat shock protein promoter, MFα1 promoter and CUP 1 promoter, and the like.

When an insect cell is used as the host cell, for example, pVL1392, pVL1393, pBlueBacIII (all manufactured by Invitrogen Corp.) and the like can be used as the expression vector.

When a plant cell is used as the host cell, examples of the expression vector include Ti plasmid, tobacco mosaic virus vector and the like.

As the promoter to be used in the expression vector for plant cells, any promoter capable of expressing in pant cells can be used, and its examples include the 35S promoter of cauliflower mosaic virus (CaMV), rice actin 1 promoter and the like.

The expression vector of the monoclonal antibody substituted with a Cys residue or the antibody fragment thereof of the present invention can be used as a type in which a light chain and a heavy chain of the antibody are present in separate vectors or as a tandem type in which these are presenting the same vector [*J. Immunol. Methods*, 167, 271 (1994)].

As the construction method of a tandem type expression vector, examples include a method in which DNA molecules encoding the light chain and heavy chain linked to promoter sequences are connected by using an appropriate restriction enzyme site. For example, regarding the tandem type expression vector, there may be mentioned as pKANTEX (WO97/10354), pEE18 [*Hybridoma*, 559 (1998)], N5KG1-Val Lark vector [*IDEC Pharmaceuticals*, a modified vector of N5KG1 (U.S. Pat. No. 6,001,358) and the like.

Examples of the method for introducing an expression vector into a host cell include a transformation method, an electroporation method [Japanese Published Unexamined Patent Application No. 257891/90, *Cytotechnology*, 3, 133 (1990)], a lipofection method [*Proc. Natl. Acad. Sci. U.S.A.*, 84, 7413 (1987)] and the like.

The substitution for Cys residue in the present invention can be carried out by site-directed mutagenesis on the vector prepared in the above. For example, the site-directed mutagenesis can be carried out by using QuickChange II Site-Directed Mutagenesis Kit (manufactured by Stratagene) and designing a primer in which the codon corresponding to the substitution site for the Cys residue of interest is replaced by TGC in accordance with the instructions attached thereto.

The presence or absence of mutation introduction into the TGC codon can be determined by a generally used nucleotide sequence analyzing method, for example, by carrying out the dideoxy method of Sanger et al. [*Proc. Natl. Acad. Sci. U.S.A.*, 74, 5463 (1977)] and the like and analyzing the results using a nucleotide sequence automatic analyzer such as a nucleotide sequence analyzer ABI PRISM377 DNA Sequencer (manufactured by Applied Biosystems) and the like.

The constructed vector for expression of the monoclonal antibody substituted with a Cys residue and the antibody fragment thereof of the present invention can be used for expression of a human chimeric antibody, a humanized antibody or the antibody fragment thereof in a procaryotic cell or a eukaryotic cell as described below.

(2) Obtaining of cDNA Encoding V Region of Antibody Derived from Non-Human Animal cDNAs encoding VL and VH of non-human animal antibody such as mouse antibody are obtained as follows.

mRNA is extracted from hybridoma cells producing an antibody and cDNA is synthesized by using is as a template. The synthesized cDNA is cloned into a vector such as a phage or a plasmid, to prepare a cDNA library.

Each of a recombinant phage or recombinant plasmid containing cDNA encoding heavy chain V region or light chain V region is isolated from the library by using DNA encoding a part of the C region or V region of a mouse antibody as the probe.

The full length of the nucleotide sequences of VL and VH of a mouse antibody of interest on the recombinant phage or recombinant plasmid are determined, and the full length of the amino acid sequences of VL and VH are deduced from the nucleotide sequences, respectively.

Hybridoma cells producing any non-human animal-derived antibody can be obtained by immunizing a non-human animal with an antigen bound to the antibody, preparing hybridomas from antibody-producing cells of the immunized animal and myeloma cells according to a known method [*Molecular Cloning*, Second Edition; *Current Protocols in Molecular Biology; Antibodies; Monoclonal Antibodies; Antibody Engineering*]. Then, cloned hybridomas are selected, cultured, and purified from the culture supernatant.

Examples of the non-human animal for preparing a hybridoma cell which produces a non-human antibody include mouse, rat, hamster, rabbit, or the like. Any animals can be used so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)] and the like.

In addition, examples of the method for preparing mRNA from total RNA include an oligo (dT) immobilized cellulose column method [*Molecular Cloning, A Laboratory Manual*, Cold Spring Harbor Laboratory Press (1989)] and the like.

Furthermore, examples of a kit for preparing mRNA from a hybridoma cell include Fast Track mRNA Isolation Kit (manufactured by Invitrogen), Quick Prep mRNA Purification Kit (manufactured by Pharmacia) and the like.

The methods for synthesizing the cDNA and preparing the cDNA library include conventional methods [*Cloning, A Laboratory Manual*, Cold Spring Harbor Lab. Press (1989), *Current Protocols in Molecular Biology*, Supplement 1-34], methods using commercially available kits, and the like. Examples of the commercially available kits include Super-Script™ Plasmid System for cDNA Synthesis and Plasmid Cloning (manufactured by GIBCO BRL), ZAP-cDNA Synthesis Kit (manufactured by Stratagene) and the like.

In preparing the cDNA library, the vector for integrating the cDNA synthesized by using the mRNA extracted from a hybridoma cell as a template may be any vector so long as the cDNA can be integrated.

Examples of suitable vectors include ZAP Express [*Strategies*, 5, 58 (1992)], pBluescript II SK(+) [*Nucleic Acids Research*, 17, 9494 (1989)], λZAP II (manufactured by STRATAGENE), λgt10, λgt11 [*DNA Cloning: A Practical Approach*, I, 49 (1985)], Lambda BlueMid (manufactured by Clontech), λExCell, pT7T3 18U (manufactured by Pharmacia), pcD2 [*Mol. Cell. Biol.*, 3, 280 (1983)], pUC18 [*Gene*, 33, 103 (1985)] and the like.

As *Escherichia coli* for introducing the cDNA library constructed with a phage or plasmid vector, any *Escherichia coli* can be used so long as the cDNA library can be introduced, expressed and maintained.

Examples of suitable *Escherichia coli* include XL1-Blue MRF' [*Strategies*, 5, 81 (1992)], C600 [*Genetics*, 39, 440 (1954)], Y1088, Y1090 [*Science*, 222, 778 (1983)], NM522 [*J. Mol. Biol.*, 166, 1 (1983)], K802 [*J. Mol. Biol.*, 16, 118 (1966)], JM105 [*Gene*, 38, 275 (1985)] and the like.

The methods for selecting the cDNA clones encoding VL and VH of a non-human animal-derived antibody from the cDNA library include colony hybridization or plaque hybridization [*Molecular Cloning, A Laboratory Manual*, Cold Spring Harbor Laboratory Press New York (1989)] using an isotope- or fluorescence-labeled probe.

It is also possible to prepare the cDNAs encoding VL and VH by preparing primers and carrying out PCR [*Molecular Cloning, A Laboratory Manual*, Cold Spring Harbor Laboratory Press New York (1989), *Current Protocols in Molecular Biology*, Supplement 1-34] by using the cDNA or cDNA library as a template.

The nucleotide sequences of the cDNAs selected by the above methods can be determined by cleaving the cDNAs with appropriate restriction enzymes, cloning the fragments into a plasmid such as pBluescript SK(−) (manufactured by STRATAGENE), and then analyzing the sequences by nucleotide sequence analyzing methods described in 1-(1).

The full length of amino acid sequences of VL and VH are deduced from the determined nucleotide sequences and compared with the full length of amino acid sequences of VL and VH of a known antibody [*Sequences of Proteins of Immunological Interest*, US Dept. Health and Human Services (1991)], whereby it can be confirmed that the obtained cDNAs encode amino acid sequences which completely comprise VL and VH of the antibody including secretory signal sequences.

Further, when the amino acid sequence of an antibody variable region or the nucleotide sequence of DNA encoding the variable region is already known, the DNA can be obtained by the following methods.

When the amino acid sequence is known, the DNA can be obtained by designing a DNA sequence encoding the variable region taking into consideration the frequency of codon usage [*Sequences of Proteins of Immunological Interest*, US Dept. Health and Human Services (1991)], synthesizing several synthetic DNAs constituting approximately 100-nucleotides based on the designed DNA sequence, and carrying out PCR using the synthetic DNAs. When the nucleotide sequence is known, the DNA can be obtained by synthesizing several synthetic DNAs constituting approximately 100-nucleotides based on the nucleotide sequence information and carrying out PCR using the synthetic DNAs.

(3) Analysis of the Amino Acid Sequence of the V Region of an Antibody from a Non-Human Animal By comparing the full length of amino acid sequences of VL and VH of the antibody including secretory signal sequences with the amino acid sequences of VL and VH of a known antibody [*Sequences of Proteins of Immunological Interest*, US Dept. Health and Human Services (1991)], it is possible to deduce the length of the secretory signal sequences and the N-terminal amino acid sequences and further to know the subgroup to which the antibody belongs. In addition, the amino acid sequences of CDRs of VL and VH can be deduced in a similar manner.

(4) Construction of an Expression Vector of Human Chimeric Antibody Substituted with a Cys Residue or an Antibody Fragment Thereof An expression vector of a human chimeric antibody substituted with a Cys residue or the antibody fragment thereof can be constructed by inserting the cDNAs encoding VL and VH of an antibody of a non-human animal into sites upstream of the genes encoding CL and CH of the human chimeric antibody substituted with Cys residues or the antibody fragment thereof in the vector for expression of the human chimeric antibody substituted a Cys residue or the antibody fragment thereof described in 1-(1).

For example, an expression vector of the human chimeric antibody substituted with a Cys residue or the antibody fragment thereof can be constructed by ligating the cDNAs encoding VL and VH of an antibody of a non-human animal respectively to synthetic DNAs comprising the 3'-terminal nucleotide sequences of VL and VH of an antibody of a non-human animal and the 5'-terminal nucleotide sequences of CL and CH of a human antibody and also having recognition sequences for appropriate restriction enzymes at both ends, and inserting them into sites upstream of the genes encoding CL and CH of a human antibody in the vector for expression of the monoclonal antibody substituted with a Cys residue or the antibody fragment thereof described in 1-(1) so as to express them in an appropriate form.

(5) Construction of cDNA Encoding V Region of a Humanized Antibody cDNAs encoding VL and VH of a humanized antibody can be constructed in the following manner. First, amino acid sequences of FRs of VL and VH of a human antibody for grafting CDRs of VL and VH of a non-human animal-derived antibody are selected.

The amino acid sequences of FRs of VL and VH of a human antibody may be any of those from human antibodies. Suitable sequences include the amino acid sequences of FRs of VL and VH of human antibodies registered at databases such as Protein Data Bank, the amino acid sequences common to subgroups of FRs of VLs and VHs of human antibodies [*Sequences of Proteins of Immunological Interest*, US Dept. Health and Human Services (1991)], and the like. In order to prepare a humanized antibody having a sufficient activity, it is preferred to select amino acid sequences having a homology of as high as possible (at least 60% or more) with the amino acid sequences of FRs of VL and VH of the desired non-human animal-derived antibody.

Next, the amino acid sequences of CDRs of VL and VH of the desired non-human animal-derived antibody are grafted to the selected amino acid sequences of FRs of VL and VH of a human antibody to design amino acid sequences of VL and VH of a humanized antibody. The designed amino acid sequences are converted into DNA sequences taking into consideration the frequency of codon usage in the nucleotide sequences of antibody genes [*Sequences of Proteins of Immunological Interest*, US Dept. Health and Human Services (1991)], and DNA sequences encoding the amino acid sequences of VL and VH of the humanized antibody are designed.

Several synthetic DNAs constituting approximately 100-nucleotides are synthesized based on the designed DNA sequences, and PCR is carried out using the synthetic DNAs. It is preferred to design 4 to 6 synthetic DNAs for each of the H chain and the L chain in view of the reaction efficiency of PCR and the lengths of DNAs that can be synthesized.

Cloning into the expression vector for the monoclonal antibody substituted with Cys residues and the antibody fragment thereof of the present invention constructed in 1-(1) can be easily carried out by introducing recognition sequences for appropriate restriction enzymes to the 5'-terminals of synthetic DNAs present on both ends.

After the PCR, the amplification products are cloned into a plasmid such as pBluescript SK(−) (manufactured by STRATAGENE) and the nucleotide sequences are determined by nucleotide sequence analyzing methods described in 1-(1) to obtain a plasmid carrying DNA sequences encoding the amino acid sequences of VL and VH of the desired humanized antibody.

(6) Modification of the Amino Acid Sequence of V Region of a Humanized Antibody

It is known that a humanized antibody prepared merely by grafting CDRs of VL and VH of a non-human animal-derived antibody to FRs of VL and VH of a human antibody has a lower antigen-binding activity compared with the original non-human animal-derived antibody [*BIO/TECHNOLOGY*, 9, 266 (1991)].

This is probably because in VL and VH of the original non-human animal-derived antibody, not only CDRs but also some of the amino acid residues in FRs are involved directly or indirectly in the antigen-binding activity, and such amino acid residues are replaced by amino acid residues of FRs of VL and VH of the human antibody by CDR grafting.

In order to solve this problem, attempts have been made in the preparation of a humanized antibody to raise the lowered antigen-binding activity by identifying the amino acid residues in the amino acid sequences of FRs of VL and VH of a human antibody which are directly relating to the binding to an antigen or which are indirectly relating to it through interaction with amino acid residues in CDRs or maintenance of the three-dimensional structure of antibody, and modifying such amino acid residues to those derived from the original non-human animal-derived antibody [*BIO/TECHNOLOGY*, 9, 266 (1991)].

In the preparation of a humanized antibody, it is most important to efficiently identify the amino acid residues in FR which are relating to the antigen-binding activity. For the efficient identification, construction and analyses of the three-dimensional structures of antibodies have been carried out by X ray crystallography [J. Mol. Biol., 112, 535 (1977)], computer modeling [Protein Engineering, 7, 1501 (1994)], and the like.

Although these studies on the three-dimensional structures of antibodies have provided much information useful for the preparation of humanized antibodies, there is no established method for preparing a humanized antibody that is adaptable to any-type of antibody. That is, at present, it is still necessary to make trial-and-error approaches, e.g., preparation of several modifications for each antibody and examination of each modification for the correlation with the antigen-binding activity.

Modification of the amino acid residues in FRs of VL and VH of a human antibody can be achieved by PCR as described in 1 (5) of this section by using synthetic DNAs for modification. The nucleotide sequence of the PCR amplification product is determined by the method described in 1 (1) of this section to confirm that the desired modification has been achieved.

(7) Construction of an Expression Vector of Humanized Antibody Substituted with Cys Residues and the Antibody Fragment Thereof An expression vector of a humanized antibody substituted with a Cys residue or the antibody fragment thereof can be constructed by inserting the cDNAs encoding VL and VH of the humanized antibody constructed in 1-(5) and 1-(6) into sites upstream of the genes encoding CL and CH of a human antibody in the vector for expression of the huminized antibody substituted with a Cys residue or the antibody fragment thereof of the present invention described in 1-(1).

For example, a expression vector of a humanized antibody substituted with a Cys residue or the antibody fragment thereof can be constructed by introducing recognition sequences for appropriate restriction enzymes to the 5'-terminals of synthetic DNAs present on both ends among the synthetic DNAs used for constructing VL and VH of the humanized antibody used in 1-(5) and 1-(6), and inserting them into sites upstream of the genes encoding CL and CH of a human antibody in the vector for expression of the monoclonal antibody substituted with Cys residues and the antibody fragment thereof of the present invention described in 1-(1) so as to express them in an appropriate form.

2. Construction of Expression Vector of the Monoclonal Antibody Substituted with a Cys Residue or the Antibody Fragment Thereof Using a Prokaryotic Cell The stable expression of the monoclonal antibody substituted with a Cys residue or the antibody fragment thereof can be achieved by introducing an expression vector of a human chimeric antibody or humanized antibody substituted with a Cys residue, or the antibody fragment thereof described in 1-(4) or 1-(7) into a prokaryotic cell to obtain a transformant which stably expresses a human chimeric antibody or humanized antibody substituted with a Cys residue, or the antibody fragment thereof.

As the prokaryotic cell to be introduced with an expression vector of the monoclonal antibody substituted with a Cys residue or the antibody fragment, any cell can be used as long as it is a prokaryotic cell which can produce a recombinant antibody. Examples of the prokaryotic cell include *Escherichia coli*, *Bacillus subtilis*, *Salmonella* strain, genus *Serratia*, genus *Pseudomonas* and the like. Among them, *Escherichia coli* is particularly preferable.

As the method for introducing an expression vector, any method can be used as long as it is a method for introducing DNA into the above-mentioned host cells. Examples include a method which uses calcium ion [the method described in *Proc. Natl. Acad. Sci. U.S.A.*, 69, 2110 (1972), *Gene*, 17, 107 (1982) and *Molecular & General Genetics*, 168, 111 (1979)], an electroporation method [Japanese Published Unexamined Patent Application No. 257891/90, *Cytotechnology*, 3, 133 (1990)] and the like.

After introduction of the expression vector, a transformant capable of stably producing the Cys residue-substituted monoclonal antibody or the antibody fragment can be selected by a medium for prokaryotic cell culture containing a drug such as ampicillin and the like.

Examples of the medium for prokaryotic cell culture include LB medium (manufactured by Becton, Dickinson and Company), NZYM GIT medium (manufactured by Nihon Pharmaceutical Co., Ltd.), Terrific Broth medium (manufactured by Applichem), SOB medium (manufactured by Applichem), SOC medium (manufactured by Ampliqon) or media in which various antibiotics such as ampicillin and the like are added, and the like.

By culturing the thus obtained transformant in the medium, the monoclonal antibody substituted with a Cys residue or the antibody fragment thereof can be produced and accumulated in the culture supernatant. In addition, in the case of a transformant transformed with a recombinant vector using an inducible promoter as the promoter, an inducer may be added to the medium in response to the necessity.

Examples of the aforementioned inducer include isopropyl-β-D-thiogalactopyranoside and the like when a microorganism transformed with a recombinant vector using trp promoter is cultured, and indole acrylate and the like when a microorganism transformed with a recombinant vector using trp promoter is cultured.

Produced amount and antigen binding activity of the Cys residue-substituted monoclonal antibody or the antibody fragment in the cells of a transformant of prokaryotic cell or the culture supernatant can be measured by an enzyme-linked immunosorbent assay [hereinafter referred to as ELISA method, *Antibodies*: A Laboratory Manual, Cold Spring Harbor Laboratory, Chapter 14 (1998), *Monoclonal Antibodies*: Principles and Practice, Academic Press Limited (1996)] and the like.

The cells of a transformant of prokaryotic cell or the monoclonal antibody substituted with a Cys residue or the antibody fragment thereof in cells of a transformant of prokaryotic cell or the culture supernatant can be purified from an *Escherichia coli* extract or a periplasm extraction fraction by an affinity purification which uses protein G or by an affinity purification which uses a tag linked to the C-terminal of constant region such as a histidine tag sequence (a tag sequence consisting of 6 continued His, hereinafter referred to as His tag).

In addition, purification methods generally employed for the purification of proteins can also be used. For example, the purification can be carried out by combinations of gel filtration, ion exchange chromatography, ultrafiltration and the like.

The molecular weight of the light chain, the heavy chain or whole antibody molecule of the purified the monoclonal antibody substituted with a Cys residue and the antibody fragment thereof can be measured by SDS-denatured polyacrylamide gel electrophoresis [hereinafter referred to as SDS-PAGE; *Nature*, 227, 680 (1970)], Western blotting [*Antibodies*: A Laboratory Manual, Cold Spring Harbor Laboratory, Chapter 12 (1988); *Monoclonal Antibodies*: Principles and Practice, Academic Press Limited (1996)], and the like.

3. Production of the Monoclonal Antibody Substituted with Cys Residue or the Antibody Fragment Thereof Using a Eukaryotic Cell The stable expression of the monoclonal antibody substituted with a Cys residue or the antibody fragment thereof can be achieved by introducing the expression vector of the human chimeric antibody or humanized antibody substituted with a Cys residue, or the antibody fragment thereof described in 1-(4) or 1-(7) into an appropriate eukaryotic cell to obtain a transformant which stably expresses a human chimeric antibody or humanized antibody substituted with a Cys residue, or the antibody fragment thereof.

When an animal cell among eukaryotic cells is used as a host cell, any animal cells may be used as long as it can express a recombinant antibody. Examples of the animal cell include mouse myeloma cell such as NS0 cell and SP2/0 cell;

Chinese hamster ovary cell such as CHO/dhfr(−) cell, CHO/DG44 cell and CHO-K1 cell, rat myeloma cell such as YB2/0 cell and IR983F cell, BHK cell derived from Syrian hamster kidney, HEK293 cell derived from Human kidney, human myeloma cell such as Namalwa cell and the like.

Among them, animal cells such as CHO/DG44 cell and CHO-K1 cell of Chinese hamster ovary cell, HEK293 cell derived from Human kidney, YB2/0 cell of rat myeloma cell and the like are preferable. In addition, the cell which can express a recombinant antibody having higher ADCC activity disclosed in WO00/61739 and WO02/31140 may be used as a host cell.

A method for introducing the expression vector may be any of method as long as it is a method for introducing DNA into the above host cell. Examples of the method include the method using calcium phosphate [*Proc. Natl. Acad. Sci. USA*, 69, 2110 (1972)], Gene, 17, 107 (1982) and Molecular&General Genetics, 168, 111 (1979)], electroporation method [Japanese Published Unexamined Patent Application No. 257891/90, Cytotechnology, 3, 133 (1990)], lipofection method [*Proc. Natl. Acad. Sci. USA*, 84, 7413 (1987)] and the like.

After the introduction of the expression vector, the transformant capable of stably producing the monoclonal antibody substituted with a Cys residue or the antibody fragment thereof can be selected using a medium for animal cell culture containing an agent such as G418 sulfate (hereinafter referred to as G418; manufactured by SIGMA) according to the method described in Japanese Published Unexamined Patent Application No. 257891/90.

Examples of the media for animal cell culture include RPMI1640 medium (manufactured by Nissui Pharmaceutical Co., Ltd.), GIT medium (manufactured by Nihon Pharmaceutical Co., Ltd.), EX-CELL 302 medium (manufactured by JRH), IMDM medium (manufactured by GIBCO BRL), Hybridoma-SFM medium (manufactured by GIBCO BRL), FreeStyle™ 293 Expression Medium (manufactured by Invitrogen), FreeStyle™ CHO Expression Medium (manufactured by Invitrogen) and media prepared by adding various additives such as fetal calf serum (hereinafter referred to as FCS) to these media.

In addition, the amount of the monoclonal antibody substituted with a Cys residue or the antibody fragment thereof produced by the transformant can be increased by utilizing a DHFR gene amplification system or the like according to the method described in Japanese Published Unexamined Patent Application No. 257891/90.

By culturing the obtained transformant in the medium, the monoclonal antibody substituted with a Cys residue or the antibody fragment thereof can be produced and accumulated in the culture supernatant.

For the culturing of the transformant obtained by using an animal cell as the host, generally employed media such as RPMI1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 medium [*Proceeding of the Society for the Biological Medicine*, 73, 1 (1950)], Whitten's medium [*Developmental Engineering Experimentation Manual—Preparation of Transgenic Mice* (Kodansha), edited by Motoya Katsuki (1987)], FreeStyle™ 293 Expression Medium (manufactured by Invitrogen) and FreeStyle™ CHO Expression Medium (manufactured by Invitrogen), media prepared by adding fetal calf serum or the like to these media, and the like can be used as the medium.

Culturing is usually carried out under conditions of pH 6.0 to 8.0 at 30 to 40° C. for 1 to 7 days in the presence of 5% $CO_2$.

If necessary, antibiotics such as kanamycin and penicillin may be added to the medium during the culturing.

The amount and the antigen-binding activity of the monoclonal antibody substituted with a Cys residue or the antibody fragment thereof produced in the culture supernatant can be measured by ELISA [*Antibodies*: A Laboratory Manual, Cold Spring Harbor Laboratory, Chapter 14 (1998); *Monoclonal Antibodies*: Principles and Practice, Academic Press Limited (1996)] or the like.

The monoclonal antibody substituted with a Cys residue or the antibody fragment thereof can be purified from the culture supernatant of the transformant using a protein A column [*Antibodies*: A Laboratory Manual, Cold Spring Harbor Laboratory, Chapter 8 (1988); *Monoclonal Antibodies*: Principles and Practice, Academic Press Limited (1996)].

In addition, purification methods generally employed for the purification of proteins can also be used. For example, the purification can be carried out by combinations of gel filtration, ion exchange chromatography, hydrophobic chromatography, ultrafiltration and the like.

The molecular weight of the light chain, the heavy chain or the whole antibody molecule of the purified monoclonal antibody substituted with a Cys residue or the antibody fragment thereof can be measured by SDS-denatured polyacrylamide gel electrophoresis [hereinafter referred to as SDS-PAGE; *Nature*, 227, 680 (1970)], Western blotting [*Antibodies: A Laboratory Manual*, Cold Spring Harbor Laboratory, Chapter 12 (1988); *Monoclonal Antibodies: Principles and Practice*, Academic Press Limited (1996)], and the like.

The monoclonal antibody substituted with a Cys residue or the antibody fragment thereof can also be produced by using yeast, an insect cell, a plant cell, or other eukaryotic cells by similar methods applied to the above animal cell.

When a yeast is used as a host cell, examples of host cells are microorganisms belonging to the genera *Saccharomyces, Schizosaccharomyces, Kluyveromyces, Trichosporon, Schwanniomyces*, and the like. Specific examples include *Saccharomyces cerevisiae, Schizosaccharomyces pombe, Kluyveromyces lactis, Trichosporon pullulans, Schwanniomyces alluvius* and the like.

A method for introducing an expression vector may be any of the methods as long as a method for introducing DNA into yeast. Examples include electroporation [*Methods Enzymol.*, 194, 182 (1990)], the spheroplast method [*Proc. Natl. Acad. Sci. USA*, 84, 1929 (1978)], the lithium acetate method [*J. Bacteriology*, 153, 163 (1983), *Proc. Natl. Acad. Sci. USA*, 75, 1929 (1978)] and the like.

The monoclonal antibody substituted with a Cys residue or the antibody fragment thereof can be produced by culturing the obtained transformant in a medium to produce and accumulate the antibody molecule in the culture and then recovering it from the resulting culture. The method for culturing the transformant in a medium can be carried out in accordance with a general method which is used for the culturing of yeast.

As the medium for culturing a transformant obtained by using yeast as the host cell, the medium may be either a natural medium or a synthetic medium, so long as it comprises materials such as a carbon source, a nitrogen source and an inorganic salt which can be assimilated by the organism and culturing of the transformant can be efficiently carried out.

As the carbon source, those which can be assimilated by the organism can be used. Examples include carbohydrates such as glucose, fructose, sucrose, molasses thereof, starch and starch hydrolysate; organic acids such as acetic acid and propionic acid; alcohols such as ethanol and propanol; and the like.

The nitrogen source includes ammonia; ammonium salts of inorganic acid or organic acid such as ammonium chloride, ammonium sulfate, ammonium acetate and ammonium phosphate; other nitrogen-containing compounds; peptone; meat extract; yeast extract; corn steep liquor; casein hydrolysate; soybean meal; soybean meal hydrolysate; various fermented cells and hydrolysates thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is usually carried out under aerobic conditions for example, by shaking culture or submerged-aeration stirring culture. The culturing temperature is preferably at 15 to 40° C., and the culturing time is generally 16 hours to 7 days. During the culturing, the pH is maintained at 3.0 to 9.0. The pH is adjusted using an inorganic or organic acid, an alkali solution, urea, calcium carbonate, ammonia or the like.

Furthermore, if necessary, an antibiotic such as ampicillin or tetracycline can be added to the medium during the culturing.

In this case, the monoclonal antibody substituted with a Cys residue or the antibody fragment thereof can be recovered in culture supernatant. Namely, the purified sample of the monoclonal antibody substituted with a Cys residue or the antibody fragment thereof can be obtained by treating the culture using a method such as centrifugation similar to the above to recover the supernatant of culture, and then using a method such as isolated purification similar to the above.

When an insect cell is used as the host, the monoclonal antibody substituted with a Cys residue or the antibody fragment thereof can be expressed by the method described in *Current Protocols in Molecular Biology, Baculovirus Expression Vectors, A Laboratory Manual*, W.H. Freeman and Company, New York (1992), *Bio/Technology*, 6, 47 (1988) or the like.

That is, the monoclonal antibody substituted with a Cys residue or the antibody fragment thereof can be expressed by co-introducing a recombinant gene-introducing vector and a baculovirus into an insect cell to obtain a recombinant virus in an insect cell culture supernatant and then infecting the insect cell with the recombinant virus.

The baculovirus includes *Autographa californica* nuclear polyhedrosis virus which is infected by an insect of the family Barathra and the like.

The insect cell includes *Spodoptera frugiperda* oocytes such as Sf9 and Sf21 [*Current Protocols in Molecular Biology, Supplement* 1-34, *Baculovirus Expression Vectors, A Laboratory Manual*, W.H. Freeman and Company, New York (1992)], a *Trichoplusiani* oocyte cellHigh 5 (manufactured by Invitrogen) and the like.

The method for co-introducing the expression vector and the baculovirus for preparing the recombinant virus includes the calcium phosphate method (Japanese Published Unexamined Patent Application No. 227075/90), the lipofection method [*Proc. Natl. Acad. Sci. USA*, 84, 7413 (1987)] and the like.

The monoclonal antibody substituted with a Cys residue or the antibody fragment thereof can be produced by culturing the transformant obtained using an insect cell as a host cell in a medium to produce and accumulate the antibody molecule in the culture and then recovering it from the resulting culture. The method for culturing the transformant in a medium can be carried out in accordance with a general method in which an insect cell is used as a host cell.

For the culturing of the transformant obtained by using an insect cell as the host, generally employed media such as TNM-FH medium (manufactured by Pharmingen, Inc.), Sf-900 II SFM medium (manufactured by Life Technologies, Inc.), ExCell 400 and ExCell 405 (manufactured by JRH Biosciences, Inc.), Grace's Insect Medium [*Nature*, 195, 788 (1962)], and the like can be used as the medium.

Culturing is usually carried out under conditions of pH 6.0 to 7.0 at 25 to 30° C. for 1 to 5 days.

If necessary, antibiotics such as gentamicin may be added to the medium during the culturing.

In this case, the monoclonal antibody substituted with a Cys residue or the antibody fragment thereof can be recovered in culture supernatant. Namely, the purified sample of the monoclonal antibody substituted with a Cys residue or the antibody fragment thereof can be obtained by treating the culture using a method such as centrifugation similar to the above to recover the supernatant of culture, and then using a method such as isolated purification similar to the above.

Examples of suitable host cells are cells of plants such as tobacco, potato, tomato, carrot, soybean, rape, alfalfa, rice, wheat and barley.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

Introduction of the recombinant vector can be carried out by any of the methods for introducing DNA into plant cells, for example, electroporation [*Cytotechnology*, 3, 133 (1990)], the calcium phosphate method (Japanese Published Unexamined Patent Application No. 227075/90), lipofection [*Proc. Natl. Acad. Sci. USA*, 84, 7413 (1987)], the injection method (*Manipulating the Mouse Embryo, A Laboratory Manual, Second Edition*, Cold Spring Harbor Laboratory Press (1994)), the method using particle gun (gene gun) (Japanese Patent Nos. 2606856 and 2517813), the DEAE-dextran method [*Biomanual Series 4—Methods of Gene Transfer, Expression and Analysis* (Yodosha), edited by Takashi Yokota and Kenichi Arai (1994)] and the virus vector method (*Manipulating the Mouse Embryo, A Laboratory Manual, Second Edition, Cold Spring Harbor Laboratory Press* (1994)).

The monoclonal antibody substituted with a Cys residue and the antibody fragment thereof can be produced by culturing the transformant obtained as above in a medium, allowing the monoclonal antibody substituted with a Cys residue or the antibody fragment thereof to produce and accumulate in the culture, and recovering them from the culture. Culturing of the transformant in a medium can be carried out by conventional methods for culturing the plant cell.

The transformant obtained by using a plant cell as the host may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, and the like can be used as the medium.

Culturing is usually carried out under conditions of pH 5.0 to 9.0 at 20 to 40° C. for 3 to 60 days. If necessary, antibiotics such as kanamycin and hygromycin may be added to the medium during the culturing.

In this case, the monoclonal antibody substituted with a Cys residue or the antibody fragment thereof can be recovered in culture supernatant. Namely, the purified sample of the monoclonal antibody substituted with a Cys residue or the antibody fragment thereof can be obtained by treating the culture using a method such as centrifugation similar to the above to recover the supernatant of culture, and then using a method such as isolated purification similar to the above.

4. Preparation of Antibody Modified Product or the Antibody Fragment Modified Product The antibody modified product substituted with a Cys residue or the antibody fragment modified product of the present invention can be obtained by modifying the monoclonal antibody substituted with a Cys residue or the antibody fragment thereof obtained in the above-mentioned 2 or 3 with a modification group having a reactivity with the thiol group of the Cys residue.

The aforementioned modification group having a reactivity with the thiol group of Cys residue (hereinafter referred also to as modification group) can be prepared by conventionally known methods (International Publication No. 96/35451, International Publication No. 01/48052).

By chemically modifying the monoclonal antibody substituted with a Cys residue or the antibody fragment thereof with the aforementioned modification group, a monoclonal antibody modified product or the antibody fragment modified product in which at least one substituted Cys residue is modified with a compound is obtained as a derivative.

It is preferable to carry out chemical modification of the monoclonal antibody substituted with a Cys residue or the antibody fragment thereof by using preferably 1 to 1,000 mol, more preferably 1 to 50 mol, of the aforementioned modification group, per mol of the antibody or the antibody fragment thereof.

Degree of modification of the monoclonal antibody or the antibody fragment thereof with the aforementioned modification group can be optionally selected by adjusting the molar ratio of the modification group per the antibody or the antibody fragment thereof, reaction temperature, pH, reaction time and the like.

In addition, the solvent to be used in the reaction may be any substance as long as it does not obstruct the reaction. For example, it is selected from phosphate buffer, borate buffer, Tris-HCl buffer, sodium hydrogencarbonate aqueous solution, sodium acetate buffer, citrate buffer, water, N,N-dimethylformamide, dimethyl sulfoxide, methanol, acetonitrile, dioxane and tetrahydrofuran and a mixed solvent thereof [see *Zoku Tanpakushitsu Hybrid* (Second Series: Protein Hybrid) edited by Yuji Inada and Hiroshi Maeda, published by Kyoritsu Shuppan (1988)].

The reaction temperature, pH and time may be any conditions so long as they do not impair activities of the monoclonal antibody substituted with a Cys residue or the antibody fragment thereof and the molecule to be used in the chemical modification. For example, temperature between 0° C. and 50° C., from 10 minutes to 100 hours and pH from 4 to 10 are preferable.

The monoclonal antibody modified product substituted with a Cys residue or the antibody fragment modified product of the present invention obtained by the above-mentioned chemical modification reaction can be purified by gel filtration, ion exchange chromatography, reverse phase high performance liquid chromatography, affinity chromatography, hydrophobic chromatography, ultrafiltration and the like, alone or in combination in accordance with the usual way. In addition, the antibody modified product substituted with a Cys residue or the antibody fragment modified product having an optional chemical modification ratio can also be purified by fractionating it using these purification methods.

The structure of the purified antibody modified product substituted with a Cys residue or structure of the antibody fragment modified product can be confirmed by, such as mass spectrometry, nuclear magnetic resonance (NMR) and amino acid composition analysis by an amino acid analyzer. In addition, the structure can also be confirmed, for example, by such as an amino acid sequence analysis which is carried out by analyzing the phenylthiohydantoin (PTH) amino acid obtained by Edman degradation by using a gas phase protein sequencer and reverse phase high performance liquid chromatography (HPLC).

5. Activity Evaluation of Monoclonal Antibody Substituted with Cys Residues or Antibody Fragment and Antibody Modified Product Substituted with Cys Residue or Antibody Fragment Derivative Thereof The activity of the purified monoclonal antibody substituted with a Cys residue or the antibody fragment thereof and the antibody modified product substituted with a Cys residue or the antibody fragment modified product of the present invention can be evaluated in the following manner.

The binding activity to the antigen is evaluated by the binding assay, fluorescent antibody technique [*Cancer Immunol. Immunother.*, 36, 373 (1993)], a surface plasmon resonance method using such as BIAcore system or the like.

As the antigen, a gene-introduced cell or a recombinant protein obtained by introducing an expression vector containing a cDNA encoding an antigen into *Escherichia coli*, yeast, an insect cell, an animal cell or the like, or a purified polypeptide or partial peptide obtained from a human tissue is used.

When the antigen is a partial peptide, a conjugate is prepared with a carrier protein such as BSA or KLH and is used.

After making these antigens into a solid layer by dispensing in a 96-well plate, a substance to be tested such as serum, a culture supernatant of a hybridoma or a purified monoclonal antibody is dispensed therein as the primary antibody and allowed to react. After thoroughly washing with PBS, PBS-Tween, and the like, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction is carried out in response to the label of the secondary antibody to select a monoclonal antibody which specifically reacts with the antigen.

In addition, CDC activity or ADCC activity against an antigen positive cell line is evaluated by a known method [*Cancer Immunol. Immunother.*, 36, 373 (1993)].

6. Use for Pharmaceutical Using the Monoclonal Antibody Substituted with Cys Residue or the Antibody Fragment Thereof; and the Antibody Modified Product Substituted with Cys Residues or the Antibody Fragment Thereof of the Present Invention The monoclonal antibody substituted with a Cys residue or antibody fragment thereof and the antibody modified product substituted with a Cys residue or the antibody fragment modified product thereof of the present invention can be used for a pharmaceutical such as a diagnostic agent and a therapeutic agent and the like.

The therapeutic agent comprising the monoclonal antibody substituted with a Cys residue or the antibody fragment thereof or the antibody modified product substituted with a Cys residue or the antibody fragment modified product thereof may be only the antibody or antibody fragment or derivatives thereof as an active ingredient, and is preferably supplied as a pharmaceutical preparation produced by an appropriate method well known in the technical field of pharmaceutics, by mixing it with one or more pharmaceutically acceptable carriers.

As a route of administration, the most effective one for therapy is pregerably used. Examples of a route of administration include oral administration and parenteral administration, such as buccal, tracheal, rectal, subcutaneous, intramuscular or intravenous administration. In case of an antibody preparation, parenteral administration is preferable.

Examples of the dosage form includes sprays, capsules, tablets, powder, granules, syrups, emulsions, suppositories, injections, ointments, tapes and the like.

The pharmaceutical preparation suitable for oral administration includes emulsions, syrups, capsules, tablets, powders, granules and the like.

Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like.

Injections can be prepared using a carrier such as a salt solution, a glucose solution or a mixture of both thereof. Or, a powder injection can be prepared by freeze-drying the monoclonal antibody substituted with a Cys residue or antibody fragment thereof or the antibody modified product substituted with a Cys residue or the antibody fragment modified product thereof according to a known method and adding sodium chloride to it.

Suppositories can be prepared using a carrier such as cacao butter, hydrogenated fat, carboxylic acid or the like.

Sprays can be prepared using the monoclonal antibody substituted with a Cys residue or the antibody fragment thereof, or the antibody modified product or the antibody fragment modified product substituted with a Cys residue as such or using it together with a carrier which does not stimulate the buccal or airway mucous membrane of the patient and can facilitate absorption of the compound by dispersing it as fine particles.

The carrier includes lactose, glycerol and the like. Depending on the properties of the monoclonal antibody substituted with a Cys residue or the antibody fragment thereof, or the antibody modified product substituted with a Cys residue or the antibody fragment modified product and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration method, treating period, age, body weight and the like, it is usually 10 µg/kg to 20 mg/kg per day and per adult.

For example, the monoclonal antibody substituted with a Cys residue or antibody fragment thereof, or the antibody modified product or the antibody fragment modified product substituted with a Cys residue is used as an anti-tumor agent, a method by using in vitro experiments or in vivo experiments can be used as a method for evaluating an anti-tumor effect of the monoclonal antibody substituted with a Cys residue or the antibody fragment thereof, or the antibody modified product or the antibody fragment modified product substituted with a Cys residue on various tumor cells.

Examples of the in vitro experiments include a method for measuring cytotoxity, a method for measuring CDC activity, a method for measuring ADCC activity and the like. In addition, examples of in vivo experiments include antitumor study using tumor system of a laboratory animal such as mouse, and the like.

According to the present invention, a monoclonal antibody in which at least one amino acid in the constant region is substituted with a cysteine residue or an antibody fragment thereof, a hybridoma which produces the monoclonal antibody or the antibody fragment thereof, a DNA encoding the monoclonal antibody or the antibody fragment thereof, a vector which comprises the DNA, a transformant which is obtainable by introducing the vector into a host cell, a method for producing a monoclonal antibody or an antibody fragment thereof using the hybridoma or the transformant, and a monoclonal antibody in which at least one substituted cysteine residue is chemically modified or the antibody fragment thereof can be provided.

EXAMPLES

The present invention is described below based on examples, though the present invention is not limited to the following examples.

Example 1

Construction of Anti-her2 Humanized Fab Expression Vector for *Escherichia coli*

1. Construction of Cloning Vector for Cys Residue Substitution

The anti-Her2 humanized Fab expression vector for *Escherichia coli* was constructed by the following procedure. As a basic structure of the expression vector for *Escherichia coli*, a commercially available vector pFLG-CTS (manufactured by SIGMA) was used. In nucleotide sequence designing of the anti-Her2 humanized antibody, the design was carried out based on the amino acid sequence of the Fab light chain region (SEQ ID NO:1) and the amino acid sequence of the Fab heavy chain region (SEQ ID NO:2) of Trastuzumab (Herceptin®) [*Proc Natl. Acad. Sci. U.S.A.*, 89, 4285 (1992)].

Under control of the nucleotide sequence (SEQ ID NO:3) containing of Tac promoter and Shine-Dalgarno sequence, the design was carried out in such a manner that the nucleotide sequences encoding the light chain and heavy chain of Fab connected with the PelB secretion signal (SEQ ID NO:4), respectively, were integrated and they were connected in tandem.

Regarding the light chain, the nucleotide sequence (SEQ ID NO:5) in which the NdeI restriction recognition sequence was added to the 5' end, and the HindIII restriction recognition sequence to the 3' end, was designed. Regarding the heavy chain, the nucleotide sequence (SEQ ID NO:6) in which the nucleotide sequence containing Tac promoter and Shine-Dalgarno sequence was added to the 5' end in addition to the EcoRI restriction enzyme recognition sequence, and His tag and the SalI restriction recognition sequence to the 3' end, was designed.

The sequences of the light chain and heavy chain were prepared by designing synthetic DNA sequences in such a manner that nucleotide sequences of 20 to 30 bp are overlapped and are connected by PCR. Regarding the light chain, its introduction into pFLAG-CTS was carried out by making use of NdeI and HindIII sites to thereby obtain pFLAG-HerFabL. Regarding the heavy chain, its introduction into pFLAG-CTS was carried out by making use of EcoRI and SalI sites and used as pFLAG-HerFabH. Using both vectors as cloning vectors for introducing Cys residue into the light chain and heavy chain, introduction of Cys point mutation was carried out.

2. Cys Point Mutation

Primers were designed based on the instructions attached to QuickChange II XL Site-Directed Mutagenesis Kit (manufactured by Stratagene). Q124C01 (SEQ ID NO:7) and Q124C02 (SEQ ID NO:8) were designed and used for the introduction of light chain Q124C; and H198C01 (SEQ ID NO:9) and H198C02 (SEQ ID NO:10) were designed and used for the introduction of light chain H198C; L201C01 (SEQ ID NO:11) and L201C02 (SEQ ID NO:12) were designed and used for the introduction of light chain L201C; A140C01 (SEQ ID NO:13) and A140C02 (SEQ ID NO:14) were designed and used for the introduction of heavy chain A140C; K147C01 (SEQ ID NO:15) and K147C02 (SEQ ID NO:16) were designed and used for the introduction of heavy chain K147C; and S183C01 (SEQ ID NO:17) and S183C02 (SEQ ID NO:18) were designed and used for the introduction of heavy chain S183C, respectively.

The reaction liquid for introducing point mutation was prepared by adding 1 µl of dNTPmix, 3 µl of QuickSolution reagent, 5 µl of 10× reaction buffer and 1 µl of PfuUltra HF DNA polymerase, attached to the kit, to 10 ng of the cloning vector prepared in the above and 125 ng of each primer, and adjusting to 50 µl with sterile water; and was used.

After heating at 95° C. for 1 minute, the amplification was carried out under conditions of 18 cycles, each cycle consisting of reactions at 95° C. for 50 seconds, 60° C. for 50 seconds and 68° C. for 7 minutes, and an elongation reaction was finally carried out at 68° C. for 7 minutes. By adding 1 µl of DpnI to the thus obtained reaction liquid, the digestion was carried out at 37° C. for 1 hour.

By subjecting the thus obtained reaction liquid to agarose gel electrophoresis, amplification of about 7 kbp of the fragment of interest was confirmed, and XL10-Gold attached to the kit was transformed by using a 2 µl portion of it.

Each plasmid DNA was prepared by cloning the thus obtained transformant, followed by reaction using Big Dye Terminator Cycle Sequencing Kit v 3.1 (manufactured by Applied Biosystems) in accordance with the instructions attached to the kit, and then Cys point mutation introduction was confirmed by a DNA sequencer ABI PRISM 3700 DNA Analyzer (manufactured by Applied Biosystems). The thus obtained Cys point mutation-introduced vectors were named as pFLAG-HerFabL-Q124C, pFLAG-HerFabL-H198C, pFLAG-HerFabL-L201C, pFLAG-HerFabH-A140C, pFLAG-HerFabH-K147C and pFLAG-HerFabH-S183C, respectively.

3. Construction of Anti-Her2 Humanized Fab Expression Vectors

Regarding the anti-Her2 humanized Fab expression vectors introduced with respective point mutations, using the light chain and heavy chain into which the point mutation of interest was introduced, a light chain fragment was obtained by treating a vector encoding the light chain with NdeI and HindIII, and a heavy chain fragment by treating a vector encoding the heavy chain with EcoRI and SalI. The light chain fragment and heavy chain fragment were connected to the pFLAG-CTS vector one by one using the Ligation High solution (manufactured by TOYOBO).

An *Escherichia coli* strain DH5α was transformed using the reaction liquid, and each plasmid DNA was prepared by cloning the thus obtained transformant and subjected to the reaction using Big Dye Terminator Cycle Sequencing Kit v 3.1 (manufactured by Applied Biosystems) in accordance with the instructions attached to the kit, and then insertion of the light fragment and heavy fragment was confirmed by a DNA sequencer ABI PRISM 3700 DNA Analyzer (manufactured by Applied Biosystems).

The thus obtained vectors expressing anti-Her2 humanized Fab of wild type (hereinafter referred to as "WT"), light chain Q124C, light chain H198C, light chain L201C, heavy chain A140C, heavy chain $K_{147}C$ and heavy chain S183C were named as pFLAG-HerFab, pFLAG-HerFab-Q124C, pFLAG-HerFab-H198C, pFLAG-HerFab-L201C, pFLAG-HerFab-A140C, pFLAG-HerFab-K147C and pFLAG-HerFab-S183C, respectively.

Example 2

Preparation of WT and Cys Residue Substitution Products of Anti-Her2 Humanized Fab Gene transformation of the *Escherichia coli* Fab expression vectors constructed in Example 1 was carried out by using an *Escherichia coli* strain W3110 (ATCC: 39936) as a host cell.

Each Fab expression vector was suspended in sterile distilled water to a concentration of 10 ng/µl, and a 3 µl portion thereof was added to 50 µl of competent cells, mildly mixed, dispensed in an Eppendorf tube and kept on ice for 30 minutes. Subsequently, this was kept in a 42° C. water bath for 30 seconds and again kept on ice for 2 minutes.

After adding 500 µl of sterile LB medium (manufactured by DIFCO), shaking culture was carried out for 60 minutes in an incubator set to 37° C. After the culturing, the entire amount was spread on an LB plate [1.5% (w/v) agarose] to which 100 µg/ml of ampicillin (manufactured by Wako Pure Chemical Industries, Ltd.) was added. After culturing in an incubator set to 37° C. overnight, an *Escherichia coli* strain grown on the plate was selected as a gene-transformed strain.

Shaking culture of the thus obtained transformant was carried out at 37° C. using the LB medium. By carrying out overnight culturing at a 10 ml scale, the thus obtained cell suspension was inoculated into 200 ml of Super-Broth medium [2 g of MOPS (manufactured by Nacalai Tesque), 6 g of Tryptone (manufactured by Difco) and 4 g of Yeast Extract (manufactured by Difco)] to which 100 µg/ml of ampicillin (manufactured by Wako Pure Chemical Industries, Ltd.) had been added.

After carrying out shaking culture at 37° C., the culture was once completed when the absorbance at 600 nm (hereinafter referred to as $OD_{600}$) became 2.0, and the medium was allowed to stand still at room temperature for about 15 minutes. By adding 1.0 mmol/l in final concentration of isopropyl-β-thiogalactopyranoside (IPTG) (manufactured by Nacalai Tesque), induction of protein expression was carried out overnight at a rate of 50 rpm in a bio-shaker set to 22° C.

An overnight-cultured *Escherichia coli* culture broth was centrifuged [CR21E (manufactured by Hitachi, Ltd.), 5000 rpm, 4° C., 15 minutes], and the weight of thus obtained precipitate was measured, thoroughly suspended by adding B-PER Bacterial Protein Extraction Reagent (manufactured by Thermo Fisher Scientific) so as to be approximately 10 ml LB-PER/g of *Escherichia coli* weight and mixed at room temperature while rotating for 10 minutes. Thereafter, the mixture was centrifuged [CR21E (manufactured by Hitachi, Ltd.), 7,000 rpm, 4° C., 25 minutes] and the thus obtained supernatant was passed through Sartolab P plus (manufactured by Sartorius Stedium Biotech) to use for purification.

Into Poly-Prep column (manufactured by BIO-RAD), 0.5 ml of TALON Resin (manufactured by Clontech) was packed and washed with 10 ml of mixture of 50 mmol/l of a phosphate buffer (pH 6.7) and 0.3 mol/l of NaCl. The mixture was prepared by the following procedure. By dissolving 31.21 g of sodium dihydrogenphosphate dihydrate (manufactured by Nacalai Tesque) in 1 liter of ultrapure water, 0.2 mol/l of a sodium dihydrogenphosphate solution was prepared.

By dissolving 71.64 g of disodium hydrogenphosphate 12-hydrate (manufactured by Junsei Chemical) in 1 liter of ultrapure water, 0.2 mol/l of a disodium hydrogenphosphate solution was prepared. By dissolving 292.2 g of NaCl (manufactured by Wako Pure Chemical Industries, Ltd.) in 800 ml of ultrapure water, 5.0 mol/l of NaCl solution was prepared. Each of mixture of 50 mmol/l of a sodium dihydrogenphosphate solution and 0.3 mol/l of NaCl and mixture of 50 mmol/l of a disodium hydrogenphosphate solution and 0.3 mol/l of NaCl was prepared, and adjusted by adding the sodium dihydrogenphosphate to the disodium hydrogenphosphate while measuring pH.

The supernatant prepared in the above into which Fab was expressed was applied to a column and washed with 10 ml of mixture of 50 mmol/l of a phosphate buffer (pH 6.7) and 0.3 mol/l of NaCl and then with 10 ml of mixture of 50 mmol/l of a phosphate buffer (pH 6.7), 0.3 mol/l of NaCl, and 5 mmol/l of imidazole (manufactured by Nacalai Tesque). After carrying out elution 3 times with the mixture of 50 mmol/l of a phosphate buffer (pH 6.7), 0.3 mol/l of NaCl, and 150 mmol/l of imidazole (manufactured by Nacalai Tesque), absorption values at 280 nm of all fractions were measured and then the second recovery fractions were used.

Using Amicon Ultra-4 30K (manufactured by Millipore Corp.), buffer exchange to mixture of 20 mmol/l of a citrate buffer (pH 6.0), 150 mmol/l of NaCl and 2 mmol/l of EDTA was carried out. While adding an appropriate amount of the buffer, the buffer exchange was carried out by centrifugation 3 times [CR21E (manufactured by Hitachi, Ltd.), 7000 g, 4° C., 4 minutes]. The final sample was centrifuged [CF15R (manufactured by Hitachi, Ltd.), 15000 rpm, 4° C., 5 minutes], and the supernatant was recovered and used in the following tests.

Regarding the thus obtained Cys residue-substituted anti-Her2 humanized Fab, the monomer content was analyzed by developing it by non-reducing SDS-PAGE (10% PAGEL, manufactured by Atto Corp.).

As a result of the above-mentioned expression and purification, those which showed 90% or more of the monomer content by the non-reducing SDS-PAGE were selected. As a result, two or more substituted sites for Cys residue, including light chain Q124C, light chain H198C, light chain L201C, heavy chain A140C, heavy chain K147C and heavy chain S183C were found. The substituted sites for Cys residue were varied without limitation to the residues structurally similar to the Cys residue, such as Ser residue, Ala residue and Val residue.

Example 3

Preparation of PEGylated Anti-Her2 Humanized Fab and Examination of PEGylation Efficiency Each of the Cys residue-substituted anti-Her2 humanized Fab obtained in Example 2 was adjusted to a concentration of from 0.5 mg/l to 1 mg/l. A maleimide type PEG reagent (average molecular weight 20 kDa, SUNBRIGHT ME-200MAOB, manufactured by NIPPON OIL & FATS CO., LTD.) corresponding to 20 equivalents based on the Cys residue-substituted anti-Her2 humanized Fab was added thereto and allowed to react therewith at room temperature for 2 hours. By developing the samples before and after the reaction by non-reducing SDS-PAGE (10% PAGEL, manufactured by Atto Corp.), the formation ratio of the PEGylated product was analyzed by GS-800 Calibrated Densitometer (manufactured by BIO-RAD).

On the samples from which about 50% or more of the formation ratio was confirmed, analysis and purification of reaction solutions were carried out using gel filtration chromatography. Regarding the gel filtration chromatography, elution of each sample was carried out while monitoring the absorption value at 280 nm using AKTApurifier (manufactured by GE Healthcare) under conditions of column: Superose (registered trademark) 12 10/300GL (manufactured by GE Healthcare), eluent: mixture of 20 mmol/l of a citrate buffer (pH 6.0) and 150 mmol/l of NaCl, flow rate: 0.5 ml/min, temperature: 4° C.

The eluent was prepared by the following procedure. By dissolving 147 g of trisodium citrate dihydrate (manufactured by Wako Pure Chemical Industries, Ltd.) in 500 ml of ultrapure water, 1.0 mol/l of a trisodium citrate solution was prepared. By dissolving 19.2 g of citric acid (manufactured by Wako Pure Chemical Industries, Ltd.) in 100 ml of ultrapure water, 1.0 mol/l of a citric acid solution was prepared.

By adding the citric acid solution to the sodium citrate solution while measuring pH, 1.0 mol/l of a sodium citrate buffer (pH 6.0) was prepared. The eluent was obtained by mixing 20 ml of 1.0 mol/l of a sodium citrate buffer (pH 6.0) with 30 ml of 5.0 mol/l of NaCl solution and adjusting the mixture to 1 liter with ultrapure water. A value of dividing the peak area of the PEGylated product by peak areas of PEGylated product and unreacted monomer was calculated as the PEGylation efficiency.

PEGylation efficiency of each Cys residue-substituted anti-Her2 humanized Fab is shown in Table 3.

TABLE 3

| Cys-introduced Fab | Q124C (light chain) | H198C (light chain) | L201C (light chain) | A140C (heavy chain) | K147C (heavy chain) | S183C (heavy chain) |
|---|---|---|---|---|---|---|
| PEGylation efficiency (%) | 85 | 63 | 80 | 81 | 45 | 60 |

As shown in Table 3, the light chain Q124C (85%), light chain L201C (80%) and heavy chain A140C (81%) showed a PEGylation efficiency of 80% or more even under conditions that reduction treatment of a Cys residue was not done as a pretreatment, and it was found that a PEGylated product could be formed at high efficiency. Particularly, the light chain Q124C formed a PEGylated product at a high efficiency of 85% or more. In addition, it was found that the light chain H198C, heavy chain K147C and heavy chain S183C also could form PEGylated products at an efficiency of round 50%, though inferior to the aforementioned three Cys residue substitution sites.

Example 4

Examination of Reactivity of Cys Residues in Cys Residue-Substituted Anti-Her2 Humanized Fab Reactivity of Cys residues in each Cys residue-substituted anti-Her2 humanized Fab obtained in Example 2 was evaluated in accordance with the descriptions in *Arch. Biochem. Biophys.*, 119, 41 (1967), under weak acidic conditions by using 4,4'-dithiopyridine (4-PDS).

Mixture of 20 mmol/l of a citrate buffer (pH 6.0), 2 mmol/l of ethylenediaminetetraacetic acid (EDTA) and 150 mmol/l of NaCl was used for the dilution of each reagent. The mixture was prepared by adding 400 µl of 0.5 mol/l of EDTA (manufactured by Nacalai Tesque) to 100 ml of the eluent prepared in Example 3.

N-acetyl-L-cysteine (manufactured by Junsei Chemical) was used for the preparation of standard curve, and a standard curve was prepared for each test. After adjusting 4-PDS (manufactured by Nacalai Tesque) to a concentration of 100 mmol/l by dissolving in an appropriate amount of methanol, it was used by diluting to 1 mmol/l with the above-mentioned citrate buffer-based mixed liquid for dilution.

50 µl of diluted solution of N-acetyl-L-cysteine or 50 µl of the Cys residue-substituted anti-Her2 humanized Fab solution obtained in Example 2 which was adjusted to 10 µmol/l was mixed with 50 µl of the 4-PDS dilution solution, and allowed to react at room temperature for 30 minutes, and then the absorbance value at 324 nm at which 4-thiopyridine formed by the reaction shows absorption maximum ($\varepsilon = 1.98 \times 10^4$) was measured by using UV-VISIBLE SPECTROPHOTOMETER UV-1700 (manufactured by Shimadzu Corp.)

After calculating theoretical value of 1 mol/l of Cys residue from the standard curve prepared based on the absorption vale of N-acetyl-L-cysteine, the number of Cys residues having reactivity contained in 1 molecule of Cys residue-substituted anti-Her2 humanized Fab was calculated from the absorption value of each Cys residue-substituted anti-Her2 humanized Fab.

The number of Cys residues having reactivity contained in 1 molecule of each Cys residue-substituted anti-Her2 humanized Fab is shown in Table 4.

TABLE 4

| Cys-introduced Fab | WT | Q124C (light chain) | L201C (light chain) | A140C (heavy chain) | A141C (heavy chain) |
|---|---|---|---|---|---|
| Cys reactivity | 0.36 | 1.34 | 1.19 | 1.17 | 1.30 |

As shown in Table 4, regarding the reactivity of Cys residue to a low molecular compound typified by 4-PDS, the light chain Q124C, light chain L201C and heavy chain A140C which showed high PEGylation efficiency in the above-mentioned Example 3 also showed a high reactivity of one or more. On the other hand, though the heavy chain A141C hardly forms PEGylated product, a high reactivity of 1 or more was found in the reactivity inspection by 4-PDS.

Accordingly, capacity of chemical modification on particularly high polymer modification groups, cannot be predicted precisely only by a low molecular compound typified by 4-PDS. However, it was considered that direct examination by chemical modification with the high molecular linker shown in the above-mentioned Example 3 is an effective method in predicting the possibility of the Cys residue site newly introduced by substitution as the chemical modification site.

Example 5

Examination of Antigen Binding Activity of Cys Residue-Substituted Anti-Her2 Humanized Fab Her2 extracellular domain prepared in accordance with the description of *Protein Eng. Des. Sel.*, 17, 455 (2004) was diluted to 10 µg/ml with Phosphate Buffered Saline (PBS) (manufactured by Nacalai Tesque) and 50 µl of the obtained solution was added to a 96 well plate for ELISA (manufactured by Greiner) to be immobilized at 4° C. overnight. After washing with PBS, PBS containing 1% bovine serum albumin (BSA) (manufactured by SIGMA) was added to the well at 100 µl/well and allowed to stand still at room temperature for 1 hour to effect adsorption.

After washing with PBS, a diluted solution of each Cys residue-substituted anti-Her2 humanized Fab obtained in Example 2 was added to the well at 50 µl/well and allowed to react at room temperature for 1 hour. After the reaction, the well was subsequently washed with PBS containing 0.05% Tween 20 (manufactured by Nacalai Tesque) (PBST), a peroxidase-labeled goat anti-human IgG $(Fab')_2$ antibody solution (manufactured by MP Biomedical) diluted 1,000-fold with PBST was added thereto at 50 µl/well and allowed to react at room temperature for 1 hour.

After the reaction and subsequent washing with PBST, the reaction substrate solution of ELISA POD Substrate TMB Kit (manufactured by Nacalai Tesque) was added at 50 µl/well and allowed to react at room temperature for 15 minutes, and then the reaction terminating liquid was added at 50 µl/well. The measurement was carried out by using EnVision 2102 Multilabel Reader (manufactured by Perkin Elmer), and antigen binding activity of each Cys residue-substituted anti-Her2 humanized Fab was calculated by using the numerical value of subtracting the absorbance at 600 nm from the absorbance at 450 nm of each well as the measured value.

Figure 2:
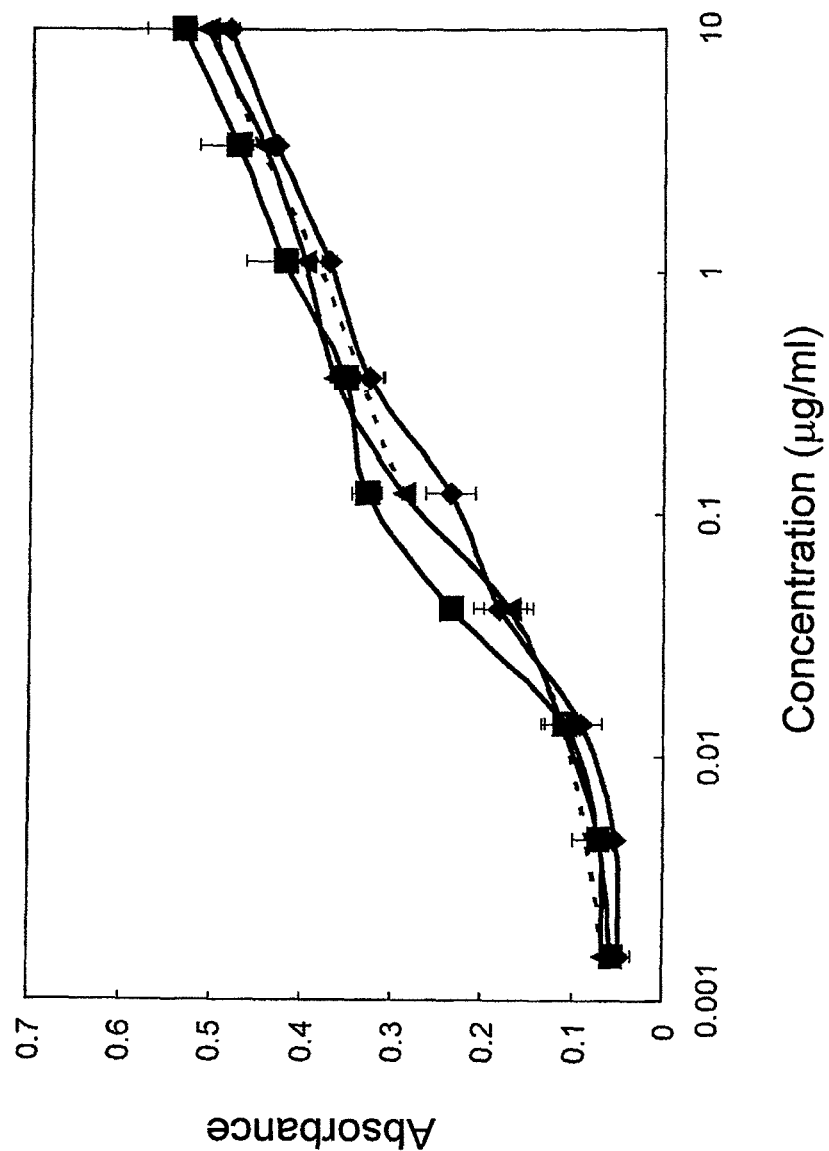
FIG. 2 is a graph showing binding activity of a Cys residue-substituted anti-Her2 Fab to Her2. The ordinate represents the absorbance at 450 nm, and the abscissa concentration of Fab (μg/ml), respectively. The wild type is represented by a dotted line, and the heavy chain A140C is represented by ▲, the heavy chain K147C is represented by ■ and the heavy chain S183C is represented by ●.

Antigen binding activity of each Cys residue-substituted Fab is shown in FIG. 1 and FIG. 2.

As shown in FIG. 1 and FIG. 2, it was found that the light chain Q124C, light chain H198C, light chain L201C, heavy chain A140C, heavy chain K147C and heavy chain S183C which showed high PEGylation efficiency in the above-mentioned Example 3 maintained an antigen binding activity similar to that of the WT.

Example 6

Preparation of Cys Residue-Substituted Anti-Her2 Humanized Fab-PEG-Val-Cit-ADM Modified Product (Fab-ADM)

1. Preparation of Maleimide-PEG-Val-Cit-ADM

In accordance with a peptide synthesis manual, such as *Peputido gousei no Kiso to Jikken* (Basis and Experiments of Peptide Synthesis), published by Maruzen (1985), *Jikken Kagaku Kouza* (Experimental Chemistry Course), 4th edition, Vol. 22, *Yuki Gousei IV* (Organic synthesis IV), Acids, Amino acids and Peptides, published by Maruzen (1999), and the like, H-Val-Cit-OH was obtained by condensing $N^\alpha$-9-fluorenylmethyloxycarbonyl-L-citrulline (Fmoc-Cit-OH, manufactured by Watanabe Chemical) and $N^\alpha$-9-fluorenylmethyloxycarbonyl-L-valine (Fmoc-Val-OH, manufactured by Watanabe Chemical) one by one on a carrier resin (dichlototrityl resin, manufactured by AnaSpec).

The thus obtained H-Val-Cit-OH and NHS-PEG12-Maleimide (manufactured by Thermo Fisher Scientific) were mixed in dimethylformamide and triethylamine and then purified in accordance with the method described in *J. Control. Release*, 69, 27 (2000), to thereby obtain Maleimide-PEG-Val-Cit-OH.

Maleimide-PEG-Val-Cit-ADM was obtained by condensing the thus obtained Maleimide-PEG-Val-Cit-OH with adriamycin (ADM) (manufactured by Wako Pure Chemical Industries, Ltd.) in accordance with the method described in *J. Control. Release*, 79, 229 (2002).

2. Preparation of Cys Residue-Substituted Anti-Her2 Humanized Fab-PEG-Val-Cit-ADM Modified Product (Fab-ADM)

After the thus obtained Maleimide-PEG-Val-Cit-ADM was dissolved in DMSO (manufactured by Wako Pure Chemical Industries, Ltd.), the obtained solution was mixed with the Cys residue-substituted anti-Her2 humanized Fab obtained in Example 2, which was buffer-exchanged with 20 mmol/l citrate buffer (pH 7.0), at 20 equivalents of per each Cys residue-substituted anti-Her2 humanized Fab, and allowed to react at room temperature for 2 hours.

After completion of the reaction, unreacted reagents were removed by carrying out gel filtration chromatography under conditions of column: Superose (registered trademark) 12 10/300GL (manufactured by GE Healthcare), eluent: mixture of 20 mmol/l of a citrate buffer (pH 6.0) and 150 mmol/l of NaCl. The eluent was prepared in the same manner as in Example 3. The fractions containing Cys residue-substituted anti-Her2 humanized Fab-PEG-Val-Cit-ADM modified product (Fab-ADM) were recovered and then concentrated using Amicon Ultra-4 30K (manufactured by Millipore Corp.) to thereby obtain purified Fab-ADM.

Example 7

Cytotoxicity Evaluation of Cys Residue-Substituted Anti-Her2 Humanized Fab-PEG-Val-Cit-ADM Modified Product (Fab-ADM)

As a target cell line, breast cancer cell line SK-BR-3 (ATCC: HTB-30) highly expressing Her2 antigen and breast cancer cell line MCF-7 (ATCC: HTB-22) poorly expressing Her2 antigen were used.

Each of the target cells was dispensed at 100 µl (5×10$^3$ cells/well) into a 96 well white flat bottom plate (manufactured by Greiner) and cultured overnight at 37° C. in a $CO_2$ incubator. After the culturing, the Fab-ADM or WT obtained in Example 2 was diluted to various concentrations in advance, and each of them was added at 50 µl/well to the well, followed by culturing at 37° C. for 5 days. To each well, 50 µl of CellTiter-Glo reagent (manufactured by Promega) was added and incubated at room temperature for 10 minutes, and then the emission was detected by EnVision 2102 Multilabel Reader (manufactured by Perkin Elmer) and cytotoxicity of Fan-ADM and WT was calculated.

Figure 3:
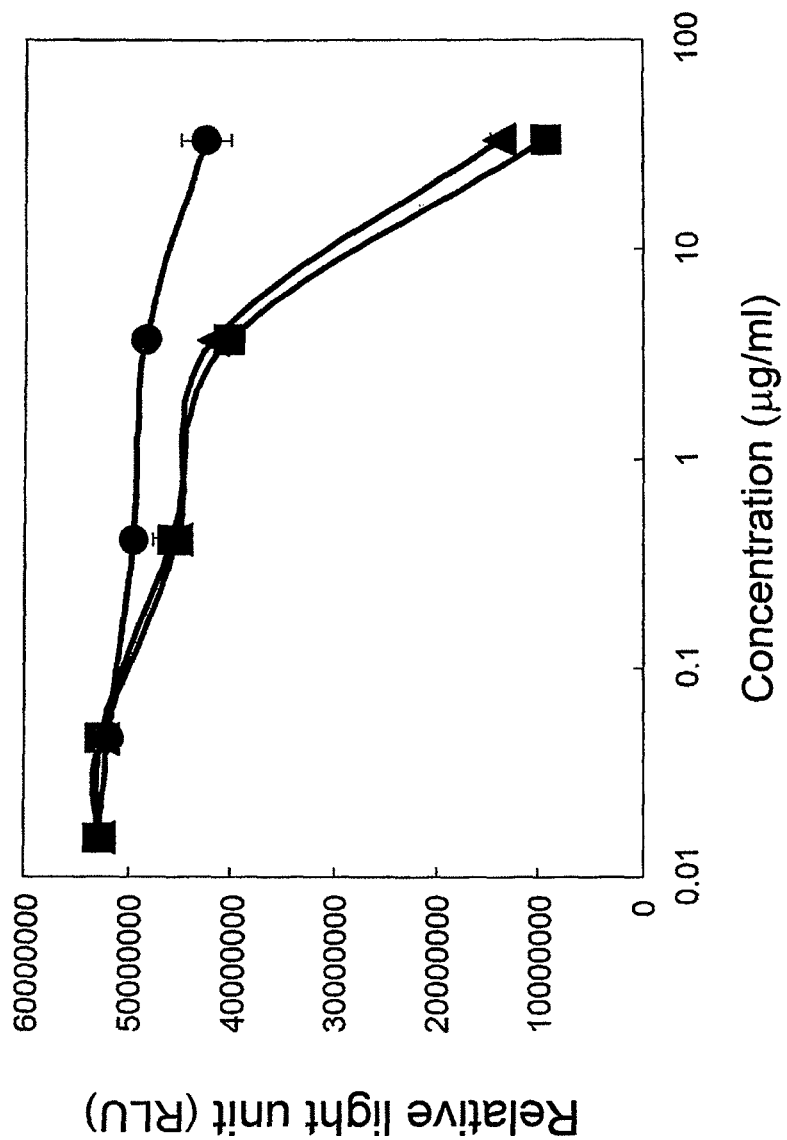
FIG. 3 is a graph showing cytotoxicity of a Cys residue-substituted anti-Her2 Fab-adriamycin linker modified product on SK-BR-3 cell. The ordinate represents relative light unit (RLU), and the abscissa concentration of the Fab-adriamycin linker modified product (μg/ml), respectively. The wild type is represented by ●, the ADM-A140C is represented by ▲ and the ADM-L201C is represented by ■.
Figure 4:
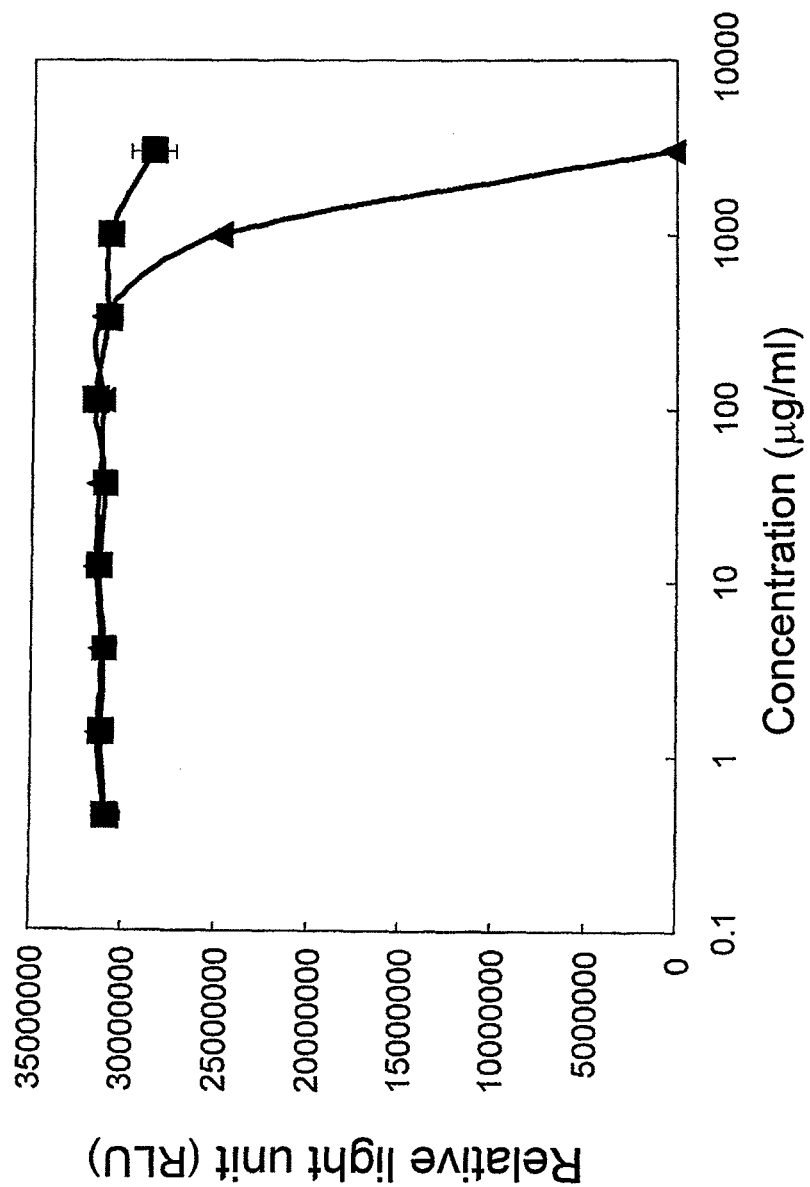
FIG. 4 is a graph showing cytotoxicity of a Cys residue-substituted anti-Her2 Fab-adriamycin linker modified product on MCF-7 cell. The ordinate represents relative light unit (RLU), and the abscissa concentration of the Fab-adriamycin linker modified product (μg/ml), respectively. The wild type is represented by ■, and the ADM-A140C is represented by ▲.

The cytotoxicity of each Fab-ADM is shown in FIG. 3 and FIG. 4.

As shown in FIG. 3 and FIG. 4, it was confirmed that the heavy chain A140C-introduced anti-Her2 humanized Fab-PEG-Val-Cit-ADM modified product (ADM-A140C) shows cytotoxicity upon SK-BR-3 and MCF-7. Further, the light chain L201C-introduced anti-Her2 humanized Fab-PEG-Val-Cit-ADM modified product (ADM-L201C) also showed cytotoxicity upon SK-BR-3. Accordingly, it was shown that the antibody modified product substituted with a Cys residue or the antibody fragment modified product of the present invention could be applied to pharmaceutical preparations as an antibody drug conjugate.

Example 8

Preparation of WT and Cys Residue-Substituted Products of Anti-CD20 Chimeric Fab Gene design of an anti-CD20 chimeric antibody was carried out in the same manner as in Example 1 based on the amino acid sequence of an Fab light chain region (SEQ ID NO:19) and the amino acid sequence of an Fab heavy chain region (SEQ ID NO:20) of Rituximab (Rituxisan) [*Cancer Res.*, 68, 3863 (2008)], and each of the expression vectors of WT and Cys residue substitution products (light chain Q124C, light chain L201C and heavy chain A140C) was prepared.

Using the expression vectors of WT and Cys residue substitution products (light chain Q124C, light chain L201C and heavy chain A140C) obtained in the same manner as in Example 2, each of proteins of the WT and Cys residue substitution products of anti-CD20 chimeric Fab was expressed and purified.

Example 9

Examination of PEGylation Efficiency of Cys Residue-Substituted Anti-CD20 Chimeric Fab Each of the Cys residue-substituted anti-CD20 chimeric Fab obtained in Example 8 was adjusted to a concentration of 0.5 to 1 mg/l. A maleimide type PEG reagent (average molecular weight 20 kDa, SUNBRIGHT ME-200MAOB, manufactured by NIPPON OIL & FATS CO., LTD.) corresponding to 20 equivalents per the Cys residue-substituted anti-CD20 chimeric Fab was added thereto and allowed to react at room temperature for 2 hours.

The thus obtained reaction liquid was analyzed by gel filtration chromatography. The gel filtration chromatography was carried out by using Prominence (manufactured by Shimadzu Corp.) under conditions of column: G3000SWXL (manufactured by Tosoh Corp.), eluent: mixture of 20 mmol/l of a citrate buffer (pH 6.0) and 150 mmol/l of NaCl, flow rate: 0.5 ml/min, and temperature: 25° C., and the absorbance value at 280 nm was monitored. A value of dividing the peak of the PEGylated product by the area of peaks of PEGylated product and unreacted monomer was calculated as the PEGylation efficiency.

PEGylation efficiency of each Cys residue-substituted anti-CD20 chimeric Fab is shown in Table 5.

TABLE 5

| Cys-introduced Fab | Q124C (light chain) | L201C (light chain) | A140C (heavy chain) |
|---|---|---|---|
| PEGylation efficiency (%) | 94 | 84 | 93 |

As shown in Table 5, similar to the case of anti-Her2 humanized Fab of Example 3, it was found that the light chain Q124C (94%), light chain L201C (84%) and heavy chain A140C (93%) showed a PEGylation efficiency of 80% or more and could form PEGylated products with high efficiency. Particularly, the light chain Q124C and heavy chain A140C formed PEGylated products with a high efficiency of exceeding 90%.

From this result, it was shown that the found Cys introduction sites had high reactivity without depending on the amino acid sequence of antibody variable region.

Example 10

Preparation of Double-Stranded DNA Prepared by Carrying Out SH Modification (S Modification) and FITC Modification on Respective 5' Ends (S Modification-FITC-dsDNA)

The 5'-end S modified DNA sequence containing 32 mer (SEQ ID NO:23) and the complementary sequence of SEQ ID NO:23 with FITC-modification at 5'-end (SEQ ID NO:24) were designed and purchased (manufactured by Sigma Aldrich). Both cases of the single-stranded DNA (ssDNA) were adjusted so as to give a concentration of 240 μmol/l using mixture of 10 mmol/l of a Tris buffer (pH 8.0), 150 mmol/l NaCl and 2 mmol/l EDTA (STE solution). After applying thereto a heat denaturation of 90° C. for 10 minutes, spontaneous cooling was carried out, thereby carrying out an annealing reaction.

Formation of a double-stranded DNA (dsDNA) was confirmed through the development by TAE-PAGE and anion exchange chromatography by using each ssDNA as a control. Regarding the TAE, UltraPure DNA Typing Grade 50×TAE buffer (manufactured by GIBCO) was used by diluting 50-fold with ultrapure water.

Regarding the anion exchange chromatography, system controller: SCL-10A and pump: LC-10Ai (manufactured by Shimadzu Corp.) were used, and absorption values at 260 nm and 495 nm were monitored under conditions of column: TSKgel DEAE-5PW (manufactured by Tosoh Corp.), eluent: A; mixture of 10 mmol/l of a Tris buffer (pH 8.0) and 150 mmol/l of NaCl, B; mixture of 10 mmol/l of a Tris buffer (pH 8.0) and 1 mol/l of NaCl, flow rate: 1 ml/min, and temperature: 25° C. As the detector, SPD-M10A (manufactured by Shimadzu Corp.) was used.

After adjusting the dsDNA solution to 500 μl with STE solution, the protecting group of S modification site was reduced by reaction with 0.04 mol/l of dithiothreitol (DTT, manufactured by Nacalai Tesque) at room temperature for 24 hours. After adding 50 μl of 3 mol/l of a sodium acetate buffer (pH 5.2) to the DNA solution and then mixing, the obtained solution was mixed with 1 ml of ethanol (manufactured by Wako Pure Chemical Industries, Ltd.) and allowed to stand still at −80° C. for 20 minutes.

Centrifugation was carried out [CF15R (manufactured by Hitachi, Ltd.), 15,000 rpm, 4° C., 10 minutes] and the supernatant was discarded. To the resulting precipitate, 1 ml of 70% ethanol solution which was cooled to −20° C. in advance was added; centrifugation was carried out [CF15R (manufactured by Hitachi, Ltd.), 15,000 rpm, 4° C., 5 minutes]; and the supernatant was discarded.

After freeze-drying the precipitate, it was dissolved in mixture of 20 mmol/l of a citrate buffer (pH 6.0), 150 mol/l of NaCl and 2 mmol/l of EDTA and subjected to the next example as the S modification-FITC-dsDNA.

Example 11

Preparation of Anti-Her2 Humanized Fab-DNA Conjugate

The Cys residue-substituted anti-Her2 humanized Fab (A140C) obtained in Example 2 was adjusted to a concentration of 0.5 to 1 mg/l. 20 equivalents of a dimaleimide reagent (BM(PEG)3, manufactured by Thermo Fisher Scientific) per the A140C was added thereto and the reaction was carried out overnight at 4° C.

By making use of NAPS (manufactured by GE Healthcare) with the mixture of 20 mmol/l of a citrate buffer (pH 6.0), 150 mmol/l of NaCl and 2 mmol/l of EDTA, unreacted BM(PEG)3 was removed from the reaction liquid. The purified maleimidated A140C (Mal-A140C) was concentrated to 5 mg/ml by carrying out centrifugation [CF15R (manufactured by Hitachi, Ltd.), 7000 rpm, 4° C.] with Ultrafree-0.5 Centrifugal Filter Device (30K NMWL, manufactured by Millipore Corp.). By developing through a non-reductive SDS-PAGE (5 to 20% PAGEL, manufactured by Atto Corp.), it was confirmed that a dimer mediated by the BM(PEG)3 reagent is not formed.

Figure 5:
FIG. 5 is a result of TAE PAGE analysis of a Cys residue-substituted anti-Her2 Fab-DNA modified product. Lane 1 represents S modified FITC labeled dsDNA alone, and lane 2 represents a sample after reaction of the Cys residue-substituted anti-Her2 Fab (A140C) with the S modified FITC labeled dsDNA. The S modified FITC labeled dsDNA is represented by ●, and the A140C-DNA modified product is represented by ▲.

1/10 equivalent of the S modification-FITC-dsDNA obtained in Example 10 per Mal-A140C was added to Mal-A140C and allowed to react overnight at 4° C. The S modification-FITC-dsDNA before the reaction and the S modification-FITC-dsDNA mixed with Mal-A140C were developed by TAE-PAGE (15 to 20% PAGEL, manufactured by Atto Corp.), fluorescence of FITC was detected by LAS4000. The thus obtained image is shown in FIG. 5.

Since the S modification-FITC-dsDNA disappeared and formation of a new band containing FITC was found in a high molecular weight region, it was shown that the Cys residue-substituted Fab of the present invention could also be applied to its conjugate with nucleic acid.

Example 12

Preparation of Anti-Her2 Humanized Fab-Alexa Fluor 488 Conjugate

The Cys residue-substituted anti-Her2 humanized Fab (A140C) obtained in Example 2 was adjusted to a concentration of 0.5 to 1 mg/l. 20 equivalents of Alexa Fluor 488 C5-maleimide (manufactured by Invitrogen) corresponding to per the A140C was added thereto and the reaction was carried out overnight at 4° C. By using NAPS (manufactured by GE Healthcare) with mixture of 20 mmol/l of a citrate buffer (pH 6.0), 150 mmol/l of NaCl and 2 mmol/l of EDTA, unreacted Alexa Fluor 488 C5-maleimide was removed from the reaction liquid using.

Making use of UV-VISIBLE SPECTROPHOTOMETER UV-1700 (manufactured by Shimadzu Corp.), the absorbances at 280 nm and 495 nm of the purified A140C-Alexa Fluor 488 were measured and the modification efficiency was calculated in accordance with the manual provided by Invitrogen. As a result, a high modification efficiency of 96% was calculated, and therefore it was shown that the Cys residue-substituted anti-Her2 humanized Fab of the present invention can be developed into a conjugate with a fluorescent reagent.

Example 13

Preparation of Anti-Her2 Humanized Fab-Biotin Conjugate and Evaluation of Streptoavidin (SA) Binding Activity Maleimide-PEG2-Biotin (manufactured by Thermo Fisher Scientific) was dissolved in DMSO (manufactured by Wako Pure Chemical Industries, Ltd.) and then mixed with each of the Cys residue-substituted anti-Her2 humanized Fab obtained in Example 2, in an amount of 20 equivalents per each Cys residue-substituted anti-Her2 humanized Fab, and allowed to react overnight at 4° C.

After completion of the reaction, the unreacted reagent was removed by carrying out gel filtration chromatography under conditions of column: Superose (registered trademark) 12 10/300GL (manufactured by GE Healthcare) and eluent: mixture of 20 mmol/l of a citrate buffer (pH 6.0) and 150 mmol/l of NaCl. The eluent was prepared in the same manner as in Example 3. The fractions containing Cys residue-substituted anti-Her2 humanized Fab-Biotin modified product (Fab-Biotin) were recovered and then concentrated by using Amicon Ultra-4 30K (manufactured by Millipore Corp.), thereby respectively obtaining each purified Fab-Biotin.

Streptoavidin (manufactured by New England Biolabs, Inc.) was diluted with PBS to 5 µg/ml, added at 50 µl/well to a 96 well plate for ELISA and immobilized overnight at 4° C. After washing with PBS, PBS containing 1% BSA was added at 100 µl/well and adsorbed thereto by standing still at room temperature for 1 hour. After washing with PBS, each of the diluted liquid of Fab-Biotin obtained in this example (0.2 µg/ml) was added to the well at 50 µl/well and allowed to react at room temperature for 1 hour. After the reaction and subsequent washing with PBS, peroxidase labeled goat anti-human IgG(Fab')$_2$ antibody solution (manufactured by MP Biomedical) diluted 1,000-fold with PBST was added to the well at 50 µl as a secondary antibody solution and allowed to react at room temperature for 1 hour.

After the reaction, the well was washed with PBST, the reaction substrate solution of ELISA POD Substrate TMB Kit was added to the well at 50 µl/well and allowed to react at room temperature for 15 minutes, and then the reaction termination liquid was added at 50 µl/well. The measurement was carried out by using EnVision 2102 Multilabel Reader, and SA binding activity of each Fab-Biotin was calculated based on the numerical value of subtracting the absorbance at 600 nm from the absorbance at 450 nm of each well as the measured value. Antigen binding activity of each Cys residue-substituted Fab is shown in FIG. 6.

Figure 6:
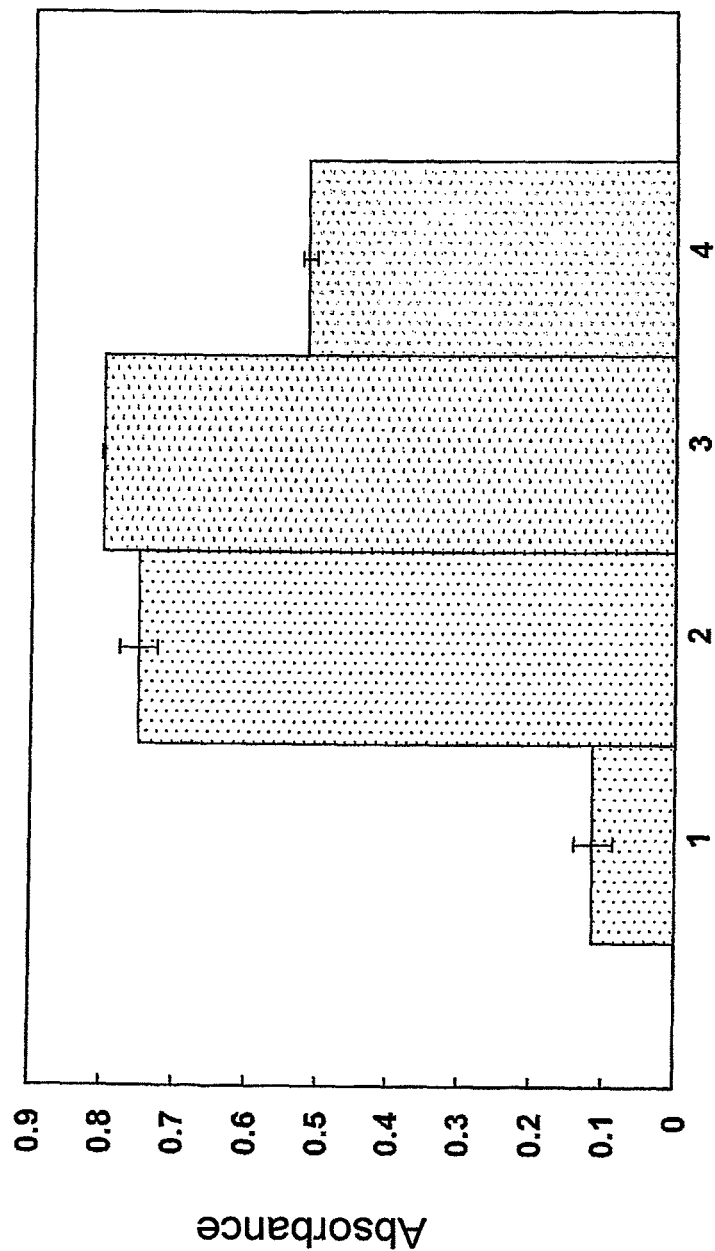
FIG. 6 is a graph showing binding activity of a Cys residue-substituted anti-Her2 Fab-Biotin modified product for streptoavidin (SA). The ordinate represents the absorbance at 450 nm. Lane 1 shows a result of the wild type, lane 2 shows a result of the A140C-Biotin modified product, lane 3 shows a result of the Q124C-Biotin modified product and lane 4 shows a result of the L201C-Biotin modified product.

As shown in FIG. 6, it was confirmed that the light chain Q124C, light chain L201C and heavy chain A140C, which showed high PEGylation efficiency in Example 3, were found to have strong SA binding activity in comparison with that of the wild type.

Example 14

Construction of Anti-Her2 Humanized Antibody and Anti-EGFR Chimeric Antibody Expression Vectors for Animal Cells 1. Construction of Wild Type Expression Vector The expression vector of anti-Her2 humanized antibody for animal cells was constructed by the following procedure. As the basic skeletal structure of the expression vector for animal cells, N5KG1-Val Lark vector [*IDEC Pharmaceuticals*, a modified vector of N5KG1 (U.S. Pat. No. 6,001,358)] was used.

In designing nucleotide sequence of the anti-Her2 humanized antibody, the design was carried out based on the sequence of the Fab light chain region amino acid (SEQ ID NO:1) and the amino acid sequence of the Fab heavy chain region (SEQ ID NO:2) of Trastuzumab (Herceptin®) [*Proc Natl. Acad. Sci. U.S.A.*, 89, 4285 (1992)].

In the design of a nucleotide sequence of the anti-EGFR chimeric antibody, the sequence was designed based on the amino acid sequence of the Fab light chain variable region (SEQ ID NO:25) and the amino acid sequence of the Fab heavy chain variable region (SEQ ID NO:26) of Cetuximab (Erbitux®) [U.S. Pat. No. 7,060,808].

Regarding the light chains, a nucleotide sequence in which a SalI restriction enzyme recognition sequence, the BglII restriction enzyme recognition sequence and a signal sequence are added to the 5' end, and an EcoRI restriction enzyme recognition sequence and the BsiWI restriction enzyme recognition sequence are added to the 3' end, was designed on the anti-Her2 humanized antibody (SEQ ID NO:27) and anti-EGFR chimeric antibody (SEQ ID NO:28).

Regarding the heavy chains, a nucleotide sequence in which the SalI restriction enzyme recognition sequence and a signal sequence are added to the 5' end, and the EcoRI restriction enzyme recognition sequence and the NheI restriction enzyme recognition sequence was added to the 3' end, was designed on the anti-Her2 humanized antibody (SEQ ID NO:29) and anti-EGFR chimeric antibody (SEQ ID NO:30).

Sequences of the light chain and heavy chain were prepared by designing synthetic DNA sequences in such a manner that 20 to 30 bp of nucleotide sequences were overlapped and connecting the synthetic DNA sequences by a PCR reaction. Regarding the light chains, these DNA sequences were introduced into pFLAG-CTS by using SalI and EcoRI sites to obtain pFLAG-TraLV and pFLAG-CetLV, respectively.

Regarding the heavy chains, their introduction into pFLAG-CTS was carried out using EcoRI and SalI sites to obtain pFLAG-TraHV and pFLAG-CetHV, respectively. Light chain variable fragments were obtained by treating the pFLAG-TraLV and pFLAG-CetLV with BglII and BsiWI, respectively, and heavy chain variable fragments were obtained by treating the pFLAG-TraHV and pFLAG-CetHV with SalI and NheI, respectively.

The light chain variable fragment and heavy chain variable fragment were connected one by one to N5KG1-Val Lark by using the Ligation High solution (manufactured by Toyobo Co., Ltd.). *Escherichia coli* strain DH5α was transformed by using the reaction liquid, and respective plasmid DNA samples were prepared from clones of the thus obtained transformants.

Each plasmid DNA reacted with Big Dye Terminator Cycle Sequencing Kit v 3.1 (manufactured by Applied Biosystems) and in accordance with the instructions attached thereto, and then insertion of the light chain fragment and heavy chain fragment was confirmed by a DNA sequencer ABI PRISM 3700 DNA Analyzer (manufactured by Applied Biosystems). The thus obtained vectors expressing wild type Trastuzumab and Cetuximab were named as N5KG1-Tra and N5KG1-Cet, respectively.

2. Introduction of Cys Point Mutation

Primers were designed based on the instructions attached to QuickChange II XL Site-Directed Mutagenesis Kit (manufactured by Stratagene). The Q124C01 (SEQ ID NO:7) and Q124C02 (SEQ ID NO:8) were used for introduction of the light chain Q124, L201C01 (SEQ ID NO:11) and L201C02 (SEQ ID NO:12) were used for introduction of the light chain L201C; and A140C01 (SEQ ID NO:13) and A140C02 (SEQ ID NO:14) were used for introduction of the heavy chain A140C.

The reaction liquid for introducing point mutation was prepared and used by adding 1 µl of dNTPmix, 3 µl of Quick Solution reagent, 5 µl of 10× reaction buffer and 1 µl of PfuUltra HF DNA polymerase which were attached to the kit to 10 ng of N5KG1-Val Lark and 125 ng of each primer and adjusting to 50 µl with sterile water to use.

After heating at 95° C. for 1 minute, the amplification reaction was carried out under conditions of 18 cycles, each cycle consisting of reactions at 95° C. for 50 seconds, 60° C. for 50 seconds and 68° C. for 9 minutes, and an elongation reaction was finally carried out at 68° C. for 7 minutes.

By adding 1 µl of DpnI to the thus obtained reaction liquid, the digestion reaction was carried out at 37° C. for 1 hour. By subjecting the thus obtained reaction liquid to agarose gel electrophoresis, amplification of about 9 kbp of the fragment of interest was confirmed, and then the XL10-Gold attached to the kit was transformed by using 2 µl of the reaction liquid.

Each plasmid DNA was prepared from clones of the thus obtained transformant and reacted with Big Dye Terminator Cycle Sequencing Kit v 3.1 (manufactured by Applied Biosystems) in accordance with the instructions attached thereto, and then Cys point mutation introduction was confirmed by a DNA sequencer ABI PRISM 3700 DNA Analyzer (manufactured by Applied Biosystems). The thus obtained Cys point mutation-introduced vectors were named as N5KG1-Q124C, N5KG1-L201C and N5KG1-A140C, respectively.

3. Construction of Expression Vectors for Cys Residue-Substituted Anti-Her2 Humanized Antibody and Cys Residue-Substituted Anti-EGFR Chimeric Antibody Regarding A140C, the expression vectors were prepared by using N5KG1-A140C, N5KG1-Tra and N5KG1-Cet. A heavy chain constant region fragment having a mutation of A140C was obtained by treating the N5KG1-A140C with NfeI and BamHI, and each fragment from which the heavy chain constant region was removed was obtained by treating N5KG1-Tra and N5KG1-Cet with NfeI and BamHI, respectively.

The thus obtained fragments were ligated by Ligation High solution (manufactured by Toyobo Co., Ltd.). *Escherichia coli* strain DH5α was transformed by using the reaction liquid, and each plasmid DNA was prepared from clones of the thus obtained transformant.

After each plasmid DNA reacted with Big Dye Terminator Cycle Sequencing Kit v 3.1 (manufactured by Applied Biosystems), in accordance with the instructions attached thereto, and then insertion of the complete length Trastuzumab nucleotide sequence or complete length Cetuximab nucleotide sequence, having a mutation of A140C, was confirmed by a DNA sequencer ABI PRISM 3700 DNA Analyzer (manufactured by Applied Biosystems). The thus obtained expression vectors of each Cys residue-substituted antibody were named as N5KG1-Tra-A140C and N5KG1-Cet-A140C, respectively.

Regarding Q124C, the expression vectors were prepared by using N5KG1-Q124C and N5KG1-Tra and N5KG1-Cet, respectively. A light chain constant region fragment having a mutation of Q124C was obtained by treating the N5KG1-Q124C with BsiWI and EcoRI, and each fragment from which the light chain constant region was removed was obtained by treating N5KG1-Tra and N5KG1-Cet with BsiWI and EcoRI, respectively.

The thus obtained fragments were ligated by Ligation High solution (manufactured by Toyobo Co., Ltd.). *Escherichia coli* strain DH5α was transformed by using the reaction liquid, and each plasmid DNA was prepared from clones of the thus obtained transformant and reacted with Big Dye Terminator Cycle Sequencing Kit v 3.1 (manufactured by Applied Biosystems) in accordance with the instructions attached thereto.

Thereafter, insertion of the complete length Trastuzumab nucleotide sequence and complete length Cetuximab nucleotide sequence, having a mutation of Q124C, was confirmed by a DNA sequencer ABI PRISM 3700 DNA Analyzer (manufactured by Applied Biosystems). The thus obtained Cys residue-substituted antibody expression vectors were named as N5KG1-Tra-Q124C and N5KG1-Cet-Q124C, respectively.

Regarding L201C, expression vectors were prepared in the same manner as the case of Q124C, except that N5KG1-L201C was used instead of N5KG1-Q124C. The thus obtained Cys residue-substituted antibody expression vectors were named as N5KG1-Tra-L201C and N5KG1-Cet-L201C, respectively.

Example 15

Preparation of WT and Cys Residue-Substituted Antibodies of Anti-Her2 Humanized Antibody and Anti-EGFR Chimeric Antibody Gene introduction of the antibody expression vector for animal cells constructed in Example 14 was carried out by using CHO-K1 or FreeStyle™ 293-F Cells (manufactured by Invitrogen) as the host cell.

In the case of using CHO-K1 as a host cell, steps from gene introduction to antibody expression were carried out based on the instructions attached to FreeStyle™ MAX CHO Expression System (manufactured by Invitrogen). With OptiPro™ SFM (manufactured by Invitrogen), 312.5 µg of the expression vector plasmid was mixed and adjusted to a total volume of 5 ml.

With OptiPro™ SFM, 312.5 µl of FreeStyle™ MAX Transfection Reagent (manufactured by Invitrogen) was mixed and adjusted to give a volume of 5 ml. The expression plasmid solution and FreeStyle™ MAX Transfection Reagent solution were mixed and allowed to stand still at room temperature for 10 minutes. After total volume of the obtained solution was added to 250 ml of CHO-K1 which had been cultured to a density of $1.0 \times 10^6$ cells/ml by using FreeStyle™ CHO Expression Medium (manufactured by Invitrogen), the cells were cultured for 1 to 5 days under condition of 37° C., 8% $CO_2$ and 135 rpm.

In the case of using FreeStyle™ 293-F Cells as a host cell, steps from gene transfer to antibody expression were carried out based on the instructions attached to FreeStyle™ MAX 293 Expression System (manufactured by Invitrogen). With Opti-MEM (registered trademark) (manufactured by Invitrogen), 250 µg of the expression vector plasmid was mixed and adjusted to give a total volume of 8.3 ml. With Opti-MEM (registered trademark), 500 µl of 293Fectin™ (manufactured by Invitrogen) was mixed, adjusted to a total volume of 8.3 ml and allowed to stand still for 5 minutes.

The expression vector plasmid solution and the 293Fectin™ solution were mixed and allowed to stand still for 20 minutes. After total volume of the obtained solution was added to 250 ml of FreeStyle™ 293-F Cells which had been cultured to a density of $1.0 \times 10^6$ cells/ml by using FreeStyle™ 293 Expression Medium (manufactured by Invitrogen), the cells were cultured for 1 to 5 days under condition of 37° C., 8% $CO_2$ and 125 rpm.

The cell culture was centrifuged [CR21E (manufactured by Hitachi, Ltd.), 2600 rpm, room temperature, 30 minutes], and the supernatant was recovered, passed through a 0.22 µl membrane filter (manufactured by IWAKI), and used for purification. In Poly-Prep column (manufactured by BIO-RAD), 1 ml of MabSelect Resin (manufactured by GE Healthcare) was packed and washed with 20 ml of DPBS (manufactured by Invitrogen).

The supernatant containing the expressed Cys residue-substituted antibody prepared in the above was applied to the column and washed with 20 ml of DPBS (manufactured by Invitrogen). Elution was carried out by using 3 ml of mixture of 20 mmol/l of a citrate buffer (pH 3.0) and 50 mmol/l of NaCl, and all fractions were recovered.

Using Vivaspin 20 30K (manufactured by GE Healthcare), buffer exchange to mixture of 20 mmol/l of a citrate buffer (pH 6.0), 150 mmol/l of NaCl and 2 mmol/l of EDTA was carried out. The buffer exchange was carried out by centrifugal concentration [Centrifuge 5810R (manufactured by Eppendorf), 3,600 rpm, 4° C., 20 minutes] twice while supplementing an appropriate volume of the buffer. The final sample was subjected to centrifugation [CF15R (manufactured by Hitachi, Ltd.), 15,000 rpm, 4° C., 5 minutes], and the supernatant was recovered and used in the subsequent tests.

Example 16

Examination of Reactivity of Cys Residues in Cys Residue-Substituted Anti-Her2 Humanized Antibody and Anti-EGFR Chimeric Antibody Regarding the methods, these experiments were carried out in accordance with Example 4. The number of Cys residues having reactivity, contained in one molecule of each Cys residue-substituted antibody, is shown in Table 6.

TABLE 6

| | Antibody | | | |
|---|---|---|---|---|
| | Anti-Her2 humanized antibody | | Anti-EGFR chimeric antibody | |
| Cys substitution site | WT | Q124C (light chain) | L201C (light chain) | A140C (heavy chain) | Q124C (light chain) |
| Cys reactivity | 0 | 1.67 | 1.61 | 1.61 | 1.94 |

As shown in Table 6, the reactivity of Cys residue in each Cys residue-substituted antibody was from 1.6 to 1.9. In addition, it was found that the result in Table 6 was correlative to the data which showed a PEGylation efficiency of 80% or more was confirmed.

Example 17

Examination on PEGylation Efficiency of Cys Residue-Substituted Anti-EGFR Chimeric Antibody Each of the Cys residue-substituted anti-EGFR chimeric antibodies obtained in Example 15 was adjusted to a concentration of 0.5 to 1 mg/l. 20 equivalents of a maleimide type PEG reagent (average molecular weight: 20 kDa, SUNBRIGHT ME-200MAOB, manufactured by NIPPON OIL & FATS CO., LTD.) per the Cys residue-substituted anti-EGFR chimeric antibody was added thereto and allowed to react at room temperature for 2 hours.

The thus obtained reaction liquid was reduced under conditions of 100 μmol/l of DTT and then developed by using 10% PAGEL (manufactured by Atto Corp.), and progress in the PEGylation was confirmed by detecting shift of the band of interest. It was shown that the Cys residue-substituted antibody of the present invention can be applied to a conjugate with PEG molecule.

Example 18

Preparation of Anti-EGFR Chimeric Antibody-Alexa Fluor 488 Conjugate

The Cys residue-substituted anti-EGFR chimeric antibody (Q124C) obtained in Example 15 was adjusted to a concentration of 3 mg/l. 20 equivalents of Alexa Fluor 488 C5-maleimide (manufactured by Invitrogen) per the Q124C was added thereto and the reaction was carried out overnight at 4° C. By using NAPS (manufactured by GE Healthcare) with mixture of 20 mmol/l of a citrate buffer (pH 6.0), 150 mmol/l of NaCl and 2 mmol/l of EDTA as eluent, unreacted Alexa Fluor 488 C5-maleimide was removed from the reaction liquid.

By using UV-VISIBLE SPECTROPHOTOMETER UV-1700 (manufactured by Shimadzu Corp.), the absorbances at 280 nm and 494 nm of the purified L201C-Alexa Fluor 488 was measured and the modification efficiency was calculated in accordance with the manual provided by Invitrogen.

As a result, binding of 2.2 molecules of Alexa Fluor 488 to 1 molecule of Q124C was verified, and it was confirmed that modification efficiency was equivalent to the theoretical value (2.0). It was shown that the Cys residue-substituted antibody of the present invention can be applied to a conjugate with a fluorescent reagent.

Example 19

Preparation of Cys Residue-Substituted Anti-EGFR Chimeric Antibody-PEG-Val-Cit-ADM Modified Product (Ab-ADM)

The preparation of Maleimide-PEG-Val-Cit-ADM was carried out in accordance with Example 6. The thus obtained Maleimide-PEG-Val-Cit-ADM was dissolved in DMSO (manufactured by Wako Pure Chemical Industries, Ltd.) and then mixed with the Cys residue-substituted anti-EGFR chimeric antibody (Q124C) obtained in Example 15 in an amount of 20 equivalents per Q124C, and allowed to react at room temperature for 2 hours.

After completion of the reaction, using Mono S (registered trademark) 5/50GL (manufactured by GE Healthcare) as the column and A buffer; 20 mmol/l of an acetate buffer (pH 5.0) and B buffer; mixture of 20 mmol/l of an acetate buffer (pH 5.0) and 1.0 mol/l of NaCl, as the eluents, a cation exchange purification was carried out with an NaCl gradient of 0 to 1.0 mol/l, thereby removing the unreacted reaction reagent.

Regarding the aforementioned eluents, these eluents were prepared by the following procedure. By diluting 22.9 ml of acetic acid (manufactured by Wako Pure Chemical Industries, Ltd.) with 1 liter of ultrapure water, 0.4 mol/l of an acetic acid solution was prepared. By diluting 32.8 g of sodium acetate (manufactured by Wako Pure Chemical Industries, Ltd.) with 1 liter of ultrapure water, 0.4 mol/l of a sodium acetate solution was prepared.

By dissolving 233.8 g of NaCl (manufactured by Wako Pure Chemical Industries, Ltd.) in 1 liter of ultrapure water, 4.0 mol/l of an NaCl solution was prepared. By mixing 296 ml of the acetic acid solution and 704 ml of the sodium acetate solution, 0.4 mol/l of an acetate buffer (pH 5.0) was prepared. By filing up 50 ml of the acetate buffer to 1 liter with ultrapure water, the A buffer was obtained.

By mixing 50 ml of the aforementioned acetate buffer and 250 ml of the NaCl solution and filing the mixture to 1 liter with ultrapure water, the B buffer was obtained. A fraction containing the Cys residue-substituted anti-EGFR chimeric antibody (Q124C)-PEG-Val-Cit-ADM modified product (Q124C-ADM) having an ADM-derived characteristic absorbance (495 nm) was recovered and then concentrated by using Amicon Ultra-4 30K (manufactured by Millipore Corp.), thereby obtaining purified Q124C-ADM.

While the present invention has been described in detail and with reference to specific embodiments thereof, it will be apparent to one skill in the art that various changes and modifications can be made therein without departing from the spirit and scope thereof.

This application is based on U.S. provisional application No. 61/317,935, filed on Mar. 26, 2010 and U.S. provisional application No. 61/389,887, filed on Oct. 5, 2010, the entire contents of which are incorporated hereinto by reference. All references cited herein are incorporated in their entirety.

[Free Text of Sequence Listing]

SEQ ID NO:1—Description of artificial sequence: Amino acid sequence of light chain of anti-Her2 humanized Fab SEQ ID NO:2—Description of artificial sequence: Amino acid sequence of heavy chain of anti-Her2 humanized Fab SEQ ID NO:3—Description of artificial sequence: Nucleotide sequence of nucleic acid comprising Tac promoter and Shine-Dalgarno sequence SEQ ID NO:4—Description of artificial sequence: Amino acid sequence of PelB secretory signal SEQ ID NO:5—Description of artificial sequence: Nucleotide sequence of light chain in anti-Her2 humanized Fab expression vector SEQ ID NO:6—Description of artificial sequence: Nucleotide sequence of heavy chain in anti-Her2 humanized Fab expression vector SEQ ID NO:7—Description of artificial sequence: Nucleotide sequence of light chain Q124C primer (Q124C01)

SEQ ID NO:8—Description of artificial sequence: Nucleotide sequence of light chain Q124C primer (Q124C02)

SEQ ID NO:9—Description of artificial sequence: Nucleotide sequence of light chain H198C primer (H198C01)

SEQ ID NO:10—Description of artificial sequence: Nucleotide sequence of light chain H198C primer (H198C02)

SEQ ID NO:11—Description of artificial sequence: Nucleotide sequence of light chain L201C primer (L201C01)

SEQ ID NO:12—Description of artificial sequence: Nucleotide sequence of light chain L201C primer (L201C02)

SEQ ID NO:13—Description of artificial sequence: Nucleotide sequence of heavy chain A140C primer (A140C01)

SEQ ID NO:14—Description of artificial sequence: Nucleotide sequence of heavy chain A140C primer (A140C02)

SEQ ID NO:15—Description of artificial sequence: Nucleotide sequence of heavy chain K147C primer (K147C01)

SEQ ID NO:16—Description of artificial sequence: Nucleotide sequence of heavy chain K147C primer (K147C02)

SEQ ID NO:17—Description of artificial sequence: Nucleotide sequence of heavy chain S183C primer (S183C01)

SEQ ID NO:18—Description of artificial sequence: Nucleotide sequence of heavy chain S183C primer (S183C02)

SEQ ID NO:19—Description of artificial sequence: Amino acid sequence of light chain of anti-CD20 chimeric Fab light chain SEQ ID NO:20—Description of artificial sequence: Amino acid sequence of heavy chain of anti-CD20 chimeric Fab SEQ ID NO:21—Description of artificial sequence: Nucleotide sequence of light chain of anti-CD20 chimeric Fab expression vector SEQ ID NO:22—Description of artificial sequence: Nucleotide sequence of heavy chain of anti-CD20 chimeric Fab expression vector SEQ ID NO:23—Description of artificial sequence: Nucleotide sequence for verifying conjugate (5' S-modification)

SEQ ID NO:24—Description of artificial sequence: Nucleotide sequence for verifying conjugate (5' FITC label)

SEQ ID NO:25—Description of artificial sequence: Amino acid sequence of light chain variable region of anti-EGFR chimeric antibody SEQ ID NO:26—Description of artificial sequence: Amino acid sequence of heavy chain variable region of anti-EGFR chimeric antibody SEQ ID NO:27—Description of artificial sequence: Nucleotide sequence of light chain variable region in anti-Her2 humanized antibody expression vector SEQ ID NO:28—Description of artificial sequence: Nucleotide sequence of light chain variable region in anti-EGFR chimeric antibody expression vector SEQ ID NO:29—Description of artificial sequence: Nucleotide sequence of heavy chain variable region in anti-Her2 humanized antibody expression vector SEQ ID NO:30—Description of artificial sequence: Nucleotide sequence of heavy chain variable region in anti-EGFR chimeric antibody expression vector

What is claimed is:

1. A monoclonal IgG antibody or antigen-binding fragment thereof, wherein said monoclonal IgG antibody or antigen-binding fragment thereof comprises a human constant region in which one or more amino acids having a solvent accessible surface area ratio of 20% or less are substituted with a cysteine residue, wherein said one or more amino acids that are substituted are selected from the group consisting of (1) to (5):
   (1) the amino acid at position 124 of human IgG light chain region in Kabat numbering,
   (2) the amino acid at position 198 of human IgG light chain region in Kabat numbering,
   (3) the amino acid at position 201 of human IgG light chain region in Kabat numbering,
   (4) the amino acid at position 147 of human IgG heavy chain region in EU numbering, and
   (5) the amino acid at position 183 of human IgG heavy chain region in EU numbering.

2. A monoclonal IgG antibody or antigen-binding fragment thereof, wherein said monoclonal IgG antibody or antigen-binding fragment thereof comprises a human constant region in which an amino acid having a solvent accessible surface area ratio of 20% or less is substituted with a cysteine residue, wherein said amino acid having a solvent accessible surface area ratio of 20% or less is position 140 of human IgG heavy chain region in EU numbering, and wherein said substituted cysteine residue is chemically modified.

3. The monoclonal IgG antibody or antigen-binding fragment thereof according to claim 1, wherein the amino acid at position 124 of human IgG light chain region in Kabat numbering is substituted with a cysteine residue.

4. The monoclonal IgG antibody or antigen-binding fragment thereof according to claim 1 or 2, wherein one or more amino acids in a CH1 region and/or a light chain constant region of said monoclonal IgG antibody or antigen-binding fragment are substituted with a cysteine residue.

5. The monoclonal IgG antibody or antigen-binding fragment thereof according to claim 1, wherein at least one of said substituted cysteine residues is chemically modified.

6. The monoclonal IgG antibody or antigen-binding fragment thereof according to claim 2 or 5, (A) wherein the substituted cysteine residue is chemically modified by a chemical modification reaction under non-reducing conditions;

(B) wherein 40% or more of said substituted cysteine residues are chemically modified;

(C) wherein the chemical modification is binding of a thiol group of the cysteine residue with a modification group comprising a hydrophilic macromolecule or amphipathic macromolecule, wherein the hydrophilic macromolecule or amphipathic macromolecule is a polyoxyalkylene, polyol or polysaccharide; and/or (D) wherein said chemical modification is binding of a thiol group of the cysteine residue with a modification group comprising a functional molecule, wherein the functional molecule is a drug, a biologically active peptide, a biologically active protein, a nucleic acid, a radiolabeled compound, a sugar chain, a lipid or a fluorescent compound.

7. The monoclonal IgG antibody or antigen-binding fragment thereof according to claim 6, wherein the functional molecule is a nucleic acid.

8. The monoclonal IgG antibody or antigen-binding fragment thereof according to claim 6, wherein the drug is an antitumor agent, an antibiotic or an antiviral agent.

9. The monoclonal IgG antibody or antigen-binding fragment thereof according to claim 6, wherein said modification group has a molecular weight of 500 Da to 100 kDa.

10. The monoclonal IgG antibody or antigen-binding fragment thereof according to claim 1 or 2, which has a cytotoxicity.

11. The monoclonal IgG antibody or antigen-binding fragment thereof according to claim 10, wherein the cytotoxicity is an antibody-dependent cellular cytotoxicity or a complement-dependent cytotoxicity.

12. The monoclonal IgG antibody or antigen-binding fragment thereof according to claim 1 or 2, wherein the antigen-binding fragment thereof is an antibody fragment selected from the group consisting of a Fab, a Fab' and a F(ab')$_2$.

13. The monoclonal IgG antibody or antigen-binding fragment thereof according to claim 1 or 2, wherein the monoclonal IgG antibody is a recombinant antibody.

14. The monoclonal IgG antibody or antigen-binding fragment thereof according to claim 13, wherein the recombinant antibody is a chimeric antibody, a humanized antibody or a human antibody.

* * * * *

SEQUENCE LISTING

```
<160> NUMBER OF SEQ ID NOS: 42

<210> SEQ ID NO 1
<211> LENGTH: 214
<212> TYPE: PRT
<213> ORGANISM: Artificial Sequence
<220> FEATURE:
<223> OTHER INFORMATION: Synthetic construct of Anti-Her2 humanized Fab
      (light chain)

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
                    85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 2
<211> LENGTH: 226
<212> TYPE: PRT
<213> ORGANISM: Artificial Sequence
<220> FEATURE:
<223> OTHER INFORMATION: Synthetic construct of Anti-Her2 humanized Fab
      (heavy chain)

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220
```

Lys Thr
225

<210> SEQ ID NO 3
<211> LENGTH: 72
<212> TYPE: DNA
<213> ORGANISM: Artificial Sequence
<220> FEATURE:
<223> OTHER INFORMATION: Synthetic construct of Tac promoter and
      Shine-Dalgarno sequence

<400> SEQUENCE: 3
gagctgttga caattaatca tcggctcgta taatgtgtgg aattgtgagc ggataacaat    60
ttcacacagg ag                                                       72

<210> SEQ ID NO 4
<211> LENGTH: 22
<212> TYPE: PRT
<213> ORGANISM: Artificial Sequence
<220> FEATURE:
<223> OTHER INFORMATION: Synthetic construct of PelB secretory signal

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 5
<211> LENGTH: 727
<212> TYPE: DNA
<213> ORGANISM: Artificial Sequence
<220> FEATURE:
<223> OTHER INFORMATION: Synthetic construct of Anti-Her2 humanized Fab
      (light chain)

<400> SEQUENCE: 5
catatgaaat acctgctgcc gaccgctgct gctggtctgc tgctcctcgc tgcccagccg    60
gcgatggccg atatccagat gacccagtcc ccgagctccc tgtccgcctc tgtgggcgat   120
agggtcacca tcacctgccg tgccagtcag gatgtgaata ctgctgtagc ctggtatcaa   180
cagaaaccag gaaaagctcc gaaactactg atttactcgg catccttcct ctactctgga   240
gtcccttctc gcttctctgg atccagatct gggacggatt tcactctgac catcagcagt   300
ctgcagccgg aagacttcgc aacttattac tgtcagcaac attatactac tcctcccacg   360
ttcggacagg gtaccaaggt ggagatcaaa cgtacggtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttaggttgcg   720
caagctt                                                            727

<210> SEQ ID NO 6
<211> LENGTH: 862
<212> TYPE: DNA
<213> ORGANISM: Artificial Sequence
<220> FEATURE:
<223> OTHER INFORMATION: Synthetic construct of Anti-Her2 humanized Fab
      (heavy chain)

<400> SEQUENCE: 6

```
gaattctgaa atgagctgtt gacaattaat catcggctcg tataatgtgt ggaattgtga      60
gcggataaca atttcacaca ggagatatca tatgaaatac ctgctgccga ccgctgctgc     120
tggtctgctg ctcctcgctg cccagccggc gatggccgag gttcagctgg tggagtctgg     180
cggtggcctg gtgcagccag ggggctcact ccgtttgtcc tgtgcagctt ctggcttcaa     240
cattaaagac acctatatac actgggtgcg tcaggcccg ggtaagggcc tggaatgggt     300
tgcaaggatt tatcctacga atggttatac tagatatgcc gatagcgtca agggccgttt     360
cactataagc gcagacacat ccaaaaacac agcctacctg cagatgaaca gcctgcgtgc     420
tgaggacact gccgtctatt attgttctag atggggaggg gacggcttct atgctatgga     480
ctactggggt caaggaaccc tggtcaccgt ctcctcggcc tccaccaagg gcccatcggt     540
cttccccctg gcaccctcct ccaagagcac ctctgggggc acagcggccc tgggctgcct     600
ggtcaaggac tacttccccg aaccggtgac ggtgtcgtgg aactcaggcg ccctgaccag     660
cggcgtgcac accttcccgg ctgtcctaca gtcctcagga ctctactccc tcagcagcgt     720
ggtgaccgtg ccctccagca gcttgggcac ccagacctac atctgcaacg tgaatcacaa     780
gcccagcaac accaaggtgg acaagaaagt tgagcccaaa tcttgtgaca aaactcatca     840
tcaccatcat cattgagtcg ac                                              862
```

<210> SEQ ID NO 7
<211> LENGTH: 34
<212> TYPE: DNA
<213> ORGANISM: Artificial Sequence
<220> FEATURE:
<223> OTHER INFORMATION: Light chain Q124C primer (Q124C01)

<400> SEQUENCE: 7

```
ccgccatctg atgagtgctt gaaatctgga actg                                  34
```

<210> SEQ ID NO 8
<211> LENGTH: 34
<212> TYPE: DNA
<213> ORGANISM: Artificial Sequence
<220> FEATURE:
<223> OTHER INFORMATION: Light chain Q124C primer (Q124C02)

<400> SEQUENCE: 8

```
cagttccaga tttcaagcac tcatcagatg gcgg                                  34
```

<210> SEQ ID NO 9
<211> LENGTH: 35
<212> TYPE: DNA
<213> ORGANISM: Artificial Sequence
<220> FEATURE:
<223> OTHER INFORMATION: Light chain H198C primer (H198C01)

<400> SEQUENCE: 9

```
cgcctgcgaa gtcacctgcc agggcctgag ctcgc                                 35
```

<210> SEQ ID NO 10
<211> LENGTH: 35
<212> TYPE: DNA
<213> ORGANISM: Artificial Sequence
<220> FEATURE:
<223> OTHER INFORMATION: Light chain H198C primer (H198C02)

<400> SEQUENCE: 10
```

-continued gcgagctcag gccctggcag gtgacttcgc aggcg        35

<210> SEQ ID NO 11
<211> LENGTH: 36
<212> TYPE: DNA
<213> ORGANISM: Artificial Sequence
<220> FEATURE:
<223> OTHER INFORMATION: Light chain L201C primer (L201C01)

<400> SEQUENCE: 11
gtcacccatc agggctgcag ctcgcccgtc acaaag        36

<210> SEQ ID NO 12
<211> LENGTH: 36
<212> TYPE: DNA
<213> ORGANISM: Artificial Sequence
<220> FEATURE:
<223> OTHER INFORMATION: Synthetic construct of Light chain L201C primer
    (L201C02)

<400> SEQUENCE: 12
ctttgtgacg ggcgagctgc agccctgatg ggtgac        36

<210> SEQ ID NO 13
<211> LENGTH: 34
<212> TYPE: DNA
<213> ORGANISM: Artificial Sequence
<220> FEATURE:
<223> OTHER INFORMATION: Heavy chain A140C primer (A140C01)

<400> SEQUENCE: 13
cacctctggg ggcacatgcg ccctgggctg cctg        34

<210> SEQ ID NO 14
<211> LENGTH: 34
<212> TYPE: DNA
<213> ORGANISM: Artificial Sequence
<220> FEATURE:
<223> OTHER INFORMATION: Heavy chain A140C primer (A140C02)

<400> SEQUENCE: 14
caggcagccc agggcgcatg tgcccccaga ggtg        34

<210> SEQ ID NO 15
<211> LENGTH: 34
<212> TYPE: DNA
<213> ORGANISM: Artificial Sequence
<220> FEATURE:
<223> OTHER INFORMATION: Heavy chain K147C primer (K147C01)

<400> SEQUENCE: 15
ctgggctgcc tggtctgcga ctacttcccc gaac        34

<210> SEQ ID NO 16
<211> LENGTH: 34
<212> TYPE: DNA
<213> ORGANISM: Artificial Sequence
<220> FEATURE:
<223> OTHER INFORMATION: Heavy chain K147C primer (K147C02)

<400> SEQUENCE: 16
gttcggggaa gtagtcgcag accaggcagc ccag        34

<210> SEQ ID NO 17
<211> LENGTH: 33
<212> TYPE: DNA

```
<213> ORGANISM: Artificial Sequence
<220> FEATURE:
<223> OTHER INFORMATION: Heavy chain S183C primer (S183C01)

<400> SEQUENCE: 17
ggactctact ccctctgcag cgtggtgacc gtg                              33

<210> SEQ ID NO 18
<211> LENGTH: 33
<212> TYPE: DNA
<213> ORGANISM: Artificial Sequence
<220> FEATURE:
<223> OTHER INFORMATION: Heavy chain S183C primer (S183C02)

<400> SEQUENCE: 18
cacggtcacc acgctgcaga gggagtagag tcc                              33

<210> SEQ ID NO 19
<211> LENGTH: 213
<212> TYPE: PRT
<213> ORGANISM: Artificial Sequence
<220> FEATURE:
<223> OTHER INFORMATION: Synthetic construct of Anti-CD20 chimeric Fab
      (light chain)

<400> SEQUENCE: 19

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 20
<211> LENGTH: 227
<212> TYPE: PRT
<213> ORGANISM: Artificial Sequence
<220> FEATURE:
```

<223> OTHER INFORMATION: Synthetic construct of Anti-CD20 chimeric Fab
      (heavy chain)

<400> SEQUENCE: 20

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr
225

<210> SEQ ID NO 21
<211> LENGTH: 724
<212> TYPE: DNA
<213> ORGANISM: Artificial Sequence
<220> FEATURE:
<223> OTHER INFORMATION: Synthetic construct of Anti-CD20 chimeric Fab
      (light chain)

<400> SEQUENCE: 21
catatgaaat acctgctgcc gaccgctgct gctggtctgc tgctcctcgc tgcccagccg      60
gcgatggccc aaattgttct ctcccagtct ccagcaatcc tgtctgcatc tccaggggag     120
aaggtcacaa tgacttgcag ggccagctca agtgtaagtt acatccactg gttccagcag     180
aagccaggat cctcccccaa acctggatt tatgccacat ccaacctggc ttctggagtc      240
cctgttcgct tcagtggcag tgggtctggg acttcttact ctctcaccat cagcagagtg     300
gaggctgaag atgctgccac ttattactgc cagcagtgga ctagtaaccc acccacgttc     360
ggagggggga ccaagctgga aatcaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac     540

```
tcccaggaga gtgtcacaga gcaggacagc aaggacagca cctacagcct cagcagcacc        600
ctgacgctga gcaaagcaga ctacgagaaa cacaaagtct acgcctgcga agtcacccat        660
cagggcctga gctcgcccgt cacaaagagc ttcaacaggg gagagtgtta ggttgcgcaa        720
gctt                                                                     724
```

```
<210> SEQ ID NO 22
<211> LENGTH: 865
<212> TYPE: DNA
<213> ORGANISM: Artificial Sequence
<220> FEATURE:
<223> OTHER INFORMATION: Synthetic construct of Anti-CD20 chimeric Fab
      (heavy chain)

<400> SEQUENCE: 22
gaattctgaa atgagctgtt gacaattaat catcggctcg tataatgtgt ggaattgtga         60
gcggataaca atttcacaca ggagatatca tatgaaatac ctgctgccga ccgctgctgc        120
tggtctgctg ctcctcgctg cccagccggc gatggcccag gtacaactgc agcagcctgg        180
ggctgagctg gtgaagcctg ggcctcagt gaagatgtcc tgcaaggctt ctggctacac        240
atttaccagt tacaatatgc actgggtaaa acagacacct ggtcggggcc tggaatggat        300
tggagctatt tatcccggaa atggtgatac ttcctacaat cagaagttca aaggcaaggc        360
cacattgact gcagacaaat cctccagcac agcctacatg cagctcagca gcctgacatc        420
tgaggactct gcggtctatt actgtgcaag atcgacttac tacggcggtg actggtactt        480
caatgtctgg ggcgcaggga ccacggtcac cgtctctgca gcctccacca agggcccatc        540
ggtcttcccc ctggcaccct cctccaagag cacctctggg ggcacagcgg ccctgggctg        600
cctggtcaag gactacttcc ccgaaccggt gacggtgtcg tggaactcag gcgccctgac        660
cagcggcgtg cacaccttcc cggctgtcct acagtcctca ggactctact ccctcagcag        720
cgtggtgacc gtgccctcca gcagcttggg cacccagacc tacatctgca acgtgaatca        780
caagcccagc aacaccaagg tggacaagaa agttgagccc aaatcttgtg acaaaactca        840
tcatcaccat catcattgag tcgac                                              865
```

```
<210> SEQ ID NO 23
<211> LENGTH: 32
<212> TYPE: DNA
<213> ORGANISM: Artificial Sequence
<220> FEATURE:
<223> OTHER INFORMATION: Synthetic construct of nucleotide for
      verification (5' S)

<400> SEQUENCE: 23
gttttaattg aacttgggcc atcgccggct gg                                       32
```

```
<210> SEQ ID NO 24
<211> LENGTH: 32
<212> TYPE: DNA
<213> ORGANISM: Artificial Sequence
<220> FEATURE:
<223> OTHER INFORMATION: Synthetic construct of nucleotide for
      verification (5' FITC)

<400> SEQUENCE: 24
ccagccggcg atggcccaag ttcaattaaa ac                                       32
```

```
<210> SEQ ID NO 25
<211> LENGTH: 108
<212> TYPE: PRT
```

<213> ORGANISM: Artificial Sequence
<220> FEATURE:
<223> OTHER INFORMATION: Synthetic construct of Anti-EGFRF chimeric Fab
      (right chain variable region)

<400> SEQUENCE: 25

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg
            100                 105

<210> SEQ ID NO 26
<211> LENGTH: 119
<212> TYPE: PRT
<213> ORGANISM: Artificial Sequence
<220> FEATURE:
<223> OTHER INFORMATION: Synthetic construct of Anti-EGFRF chimeric Fab
      (heavy chain variable region)

<400> SEQUENCE: 26

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 27
<211> LENGTH: 417
<212> TYPE: DNA
<213> ORGANISM: Artificial Sequence
<220> FEATURE:
<223> OTHER INFORMATION: Synthetic construct of Anti-Her2 humanized
      antibody (right chain variable region)

<400> SEQUENCE: 27
gtcgacagat ctctcaccat ggacatgagg gtcctcgctc agctcctggg gctcctgctg      60
ctctgtttcc caggtgccag atgtgacatc cagatgaccc agtctccatc ctcactgtct     120
gcatctgtag gagacagagt caccatcact tgtcgggcga gtcaggacgt gaacaccgcc     180

```
gtggcctggt atcagcagaa accaggcaaa gcccctaagc tgctgatcta ttccgcatcc    240
ttcttgtaca gtgggtccc  atcaaggttc agcggcagtc gatctgggac agatttcact   300
ctcaccatca gcagcctgca gcctgaagat tttgcaactt attactgcca acagcactac   360
accaccccgc ccactttggg ccaggggacc aaggtggaga tcaaacgtac ggaattc      417
```

<210> SEQ ID NO 28
<211> LENGTH: 407
<212> TYPE: DNA
<213> ORGANISM: Artificial Sequence
<220> FEATURE:
<223> OTHER INFORMATION: Synthetic construct of Anti-EGFR chimeric antibody (right chain variable region)

<400> SEQUENCE: 28

```
gtcgacagat ctccaccatg aagctgcccg tgcggctgct ggtgctgatg ttctggattc    60
ccgccagcag cagcgacatc ctgctgaccc agagccccgt gatcctgagc gtgtcccctg   120
gcgagcgggt gtccttcagc tgcagagcca gccagagcat cggcaccaac atccactggt   180
atcagcagcg gaccaacggc agccccagac tgctgattaa gtacgccagc gagtccatca   240
gcggcatccc cagccggttt agcggcagcg gctccggcac cgacttcacc ctgagcatca   300
acagcgtgga aagcgaggat atcgccgact actactgcca gcagaacaac aactggccca   360
ccaccttcgg agccggcacc aagctggaac tgaagcgtac ggaattc                 407
```

<210> SEQ ID NO 29
<211> LENGTH: 441
<212> TYPE: DNA
<213> ORGANISM: Artificial Sequence
<220> FEATURE:
<223> OTHER INFORMATION: Synthetic construct of Anti-Her2 humanized antibody (heavy chain variable region)

<400> SEQUENCE: 29

```
gtcgacacca ccatggagtt tgggctgagc tgggttttcc tcgttgctct tttaagaggt    60
gtccagtgtg aggtgcagtt ggtggagtct gggggaggcc tggtccagcc tgggggctcc   120
ctgagactct cctgtgcagc gtctggattc aacatcaagg acacctacat ccactgggtc   180
cgccaggctc caggcaaggg gctggagtgg gtggcacgta tatacccac  caacggctac   240 accagatatg cagactccgt gaagggccga ttcaccatct ccgccgacac ctccaagaac   300
acggcctatc tgcaaatgaa cagcctgaga gccgaggaca cggctgtgta ttactgttcc   360
agatggggcg gggacggctt ctacgccatg gactactggg gccagggaac cctggtcacc   420
gtctcctcag ctagcgaatt c                                             441
```

<210> SEQ ID NO 30
<211> LENGTH: 437
<212> TYPE: DNA
<213> ORGANISM: Artificial Sequence
<220> FEATURE:
<223> OTHER INFORMATION: Synthetic construct of Anti-EGFR chimeric antibody (heavy chain variable region)

<400> SEQUENCE: 30

```
gtcgacccac catgaacctg ggcctgagcc tgatcttcct ggccctgatc ctgaagggcg    60
tgcagtgcca ggtgcagctg aagcagagcg gccctggcct ggtgcagcct agccagagcc   120
tgagcatcac ctgtaccgtg tccggcttca gcctgaccaa ctacggcgtg cactgggtcc   180
gacagagccc tggcaagggc ctggaatggc tgggagtgat ttggagcggc ggcaacaccg   240
```

```
actacaacac cccgttcacc agccggctga gcatcaacaa ggacaacagc aagagccagg    300
tgttcttcaa gatgaacagc ctgcagagca acgacaccgc catctactac tgcgccgaga    360
ccctgaccta ctacgactac gagttcgcct actggggcca gggcaccctg gtcacagtgt    420
ctgccgctag cgaattc                                                   437
```

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide

<400> SEQUENCE: 31

Arg Gln Ile Lys Ile Trp Phe Gln Asn Arg Arg Met Lys Trp Lys Lys
1               5                   10                  15

<210> SEQ ID NO 32
<211> LENGTH: 14
<212> TYPE: PRT
<213> ORGANISM: Artificial Sequence
<220> FEATURE:
<223> OTHER INFORMATION: Synthetic peptide

<400> SEQUENCE: 32

Gly Arg Lys Lys Arg Arg Gln Arg Arg Arg Pro Pro Gln Cys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic peptide

<400> SEQUENCE: 33

Gly Trp Thr Leu Asn Ser Ala Gly Tyr Leu Leu Lys Ile Asn
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Arg Arg Arg Arg Arg Arg Arg Arg Arg
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic peptide

<400> SEQUENCE: 35

Thr Arg Gln Ala Arg Arg Asn Arg Arg Arg Trp Arg Glu Arg Gln
1               5                   10                  15

Arg

<210> SEQ ID NO 36
<211> LENGTH: 17

```
<212> TYPE: PRT
<213> ORGANISM: Artificial Sequence
<220> FEATURE:
<223> OTHER INFORMATION: Synthetic peptide

<400> SEQUENCE: 36

Cys Ser Ile Pro Pro Glu Val Lys Phe Asn Lys Pro Phe Val Tyr Leu
1               5                   10                  15

Ile

<210> SEQ ID NO 37
<211> LENGTH: 17
<212> TYPE: PRT
<213> ORGANISM: Artificial Sequence
<220> FEATURE:
<223> OTHER INFORMATION: Synthetic peptide

<400> SEQUENCE: 37

Lys Gly Glu Gly Ala Ala Val Leu Leu Pro Val Leu Leu Ala Ala Pro
1               5                   10                  15

Gly

<210> SEQ ID NO 38
<211> LENGTH: 29
<212> TYPE: PRT
<213> ORGANISM: Artificial Sequence
<220> FEATURE:
<223> OTHER INFORMATION: Synthetic peptide

<400> SEQUENCE: 38

Ala Ala Leu Glu Ala Leu Ala Glu Ala Leu Glu Ala Leu Ala Glu Ala
1               5                   10                  15

Leu Glu Ala Leu Ala Glu Ala Ala Ala Gly Gly Cys
            20                  25

<210> SEQ ID NO 39
<211> LENGTH: 23
<212> TYPE: PRT
<213> ORGANISM: Artificial Sequence
<220> FEATURE:
<223> OTHER INFORMATION: Synthetic peptide

<400> SEQUENCE: 39

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 40
<211> LENGTH: 30
<212> TYPE: PRT
<213> ORGANISM: Artificial Sequence
<220> FEATURE:
<223> OTHER INFORMATION: Synthetic peptide

<400> SEQUENCE: 40

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 41
<211> LENGTH: 21
<212> TYPE: PRT
```

```
<213> ORGANISM: Artificial Sequence
<220> FEATURE:
<223> OTHER INFORMATION: Synthetic peptide

<400> SEQUENCE: 41

Gly Leu Phe Glu Ala Leu Leu Glu Leu Leu Glu Ser Leu Trp Glu Leu
1               5                   10                  15

Leu Leu Leu Glu Ala
            20

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

<400> SEQUENCE: 42

Cys His Lys Lys Lys Lys Lys Lys His Cys
1               5                   10
```